United States Patent
Matsukura et al.

(10) Patent No.: US 8,183,264 B2
(45) Date of Patent: May 22, 2012

(54) PYRIDINE DERIVATIVE SUBSTITUTED BY HETEROARYL RING, AND ANTIFUNGAL AGENT COMPRISING THE SAME

(75) Inventors: Masayuki Matsukura, Tsukuba (JP); Satoshi Inoue, Tsukuba (JP); Keigo Tanaka, Tsukuba (JP); Norio Murai, Tsukuba (JP); Shuji Shirotori, Tsukuba (JP)

(73) Assignee: Eisai R&D Managment Co., Ltd., Tokyo (JP)

( * ) Notice: Subject to any disclaimer, the term of this patent is extended or adjusted under 35 U.S.C. 154(b) by 291 days.

(21) Appl. No.: 12/442,293

(22) PCT Filed: Sep. 20, 2007

(86) PCT No.: PCT/JP2007/068230
§ 371 (c)(1),
(2), (4) Date: Mar. 20, 2009

(87) PCT Pub. No.: WO2008/035726
PCT Pub. Date: Mar. 27, 2008

(65) Prior Publication Data
US 2010/0099718 A1    Apr. 22, 2010

Related U.S. Application Data

(60) Provisional application No. 60/848,359, filed on Oct. 2, 2006.

(30) Foreign Application Priority Data

Sep. 21, 2006    (JP) ................ 2006-256094

(51) Int. Cl.
*A61K 31/4439*    (2006.01)
*C07D 401/04*    (2006.01)
(52) U.S. Cl. ................... 514/340; 546/268.4
(58) Field of Classification Search ............ 546/268.4; 514/340
See application file for complete search history.

(56) References Cited

U.S. PATENT DOCUMENTS

| | | | |
|---|---|---|---|
| 4,576,956 A | 3/1986 | Makisumi et al. |
| 4,720,493 A | 1/1988 | Kawakita et al. |
| 4,785,010 A | 11/1988 | Zoller et al. |
| 5,034,393 A | 7/1991 | Hackler et al. |
| 5,070,082 A | 12/1991 | Murdock et al. |
| 5,208,247 A | 5/1993 | Trova et al. |
| 5,296,484 A | 3/1994 | Coghlan et al. |
| 5,328,921 A | 7/1994 | Trova et al. |
| 5,350,749 A | 9/1994 | Hackler et al. |
| 5,371,086 A | 12/1994 | Takemoto et al. |
| 5,691,136 A | 11/1997 | Lukski et al. |
| 5,691,336 A | 11/1997 | Dorn et al. |
| 5,710,171 A | 1/1998 | Dinsmore et al. |
| 5,747,518 A | 5/1998 | Yoshikawa et al. |
| 5,852,042 A | 12/1998 | Jakobi et al. |
| 5,945,431 A | 8/1999 | Jin et al. |
| 6,022,884 A | 2/2000 | Mantlo et al. |
| 6,080,767 A | 6/2000 | Klein et al. |
| 6,140,131 A | 10/2000 | Sunakawa et al. |
| 6,174,905 B1 | 1/2001 | Suzuki et al. |
| 6,200,975 B1 | 3/2001 | Carling et al. |
| 6,235,728 B1 | 5/2001 | Golik et al. |
| 6,255,318 B1 | 7/2001 | Bedard et al. |
| 6,310,203 B1 | 10/2001 | Carling et al. |
| 6,313,127 B1 | 11/2001 | Waterson et al. |
| 6,319,944 B1 | 11/2001 | Claiborne et al. |
| 6,340,690 B1 | 1/2002 | Bachand et al. |
| 6,380,218 B1 | 4/2002 | Marfat et al. |
| 6,407,116 B1 | 6/2002 | Kajino et al. |

(Continued)

FOREIGN PATENT DOCUMENTS

DE    19727117 A1    1/1999
(Continued)

OTHER PUBLICATIONS

Ex parte Quayle Action issued Mar. 31, 2011, in copending U.S. Appl. No. 11/658,901.

(Continued)

*Primary Examiner* — Patricia Morris
(74) *Attorney, Agent, or Firm* — Birch, Stewart, Kolasch & Birch, LLP

(57) ABSTRACT

The present invention provides an antifungal agent that has excellent antifungal action, and is also excellent in terms of its properties, safety, and metabolic stability. The present invention discloses a compound represented by the following formula I or a salt thereof, and an antifungal agent comprising the compound or the salt:

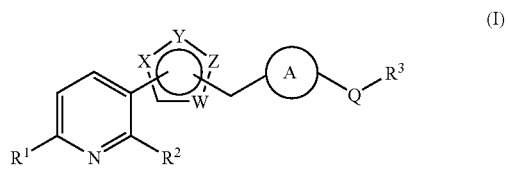

(I)

wherein $R^1$ represents a hydrogen atom, a halogen atom, an amino group, a $C_{1-6}$ alkyl group, a $C_{1-6}$ alkoxy group, or a $C_{1-6}$-alkoxy-$C_{1-6}$-alkyl group; $R^2$ represents a hydrogen atom or an amino group; X, Y, Z, and W independently represent a nitrogen atom, an oxygen atom, a sulfur atom, or —CH—, provided that at least two among X, Y, and W are nitrogen atoms; the ring A represents a 5- or 6-membered heteroaryl ring or a benzene ring; Q represents a methylene group, an oxygen atom, —$CH_2O$—, —$OCH_2$—, —NH—, —$NHCH_2$—, or —$CH_2NH$—; and $R^3$ represents a $C_{1-6}$ alkyl group, a $C_{3-8}$ cycloalkyl group, a $C_{6-10}$ aryl group, or a 5- or 6-membered heteroaryl group, each of which may have one or two substituents.

12 Claims, No Drawings

U.S. PATENT DOCUMENTS

| | | |
|---|---|---|
| 6,414,013 B1 | 7/2002 | Fancelli et al. |
| 6,596,718 B1 | 7/2003 | Flohr et al. |
| 6,630,495 B1 | 10/2003 | Cooke et al. |
| 7,179,804 B2 | 2/2007 | Amegadzie et al. |
| 7,179,822 B2 | 2/2007 | Bunker et al. |
| 7,687,525 B2 | 3/2010 | Suzuki et al. |
| 7,691,882 B2 | 4/2010 | Tanaka et al. |
| 7,754,726 B2 | 7/2010 | Lang et al. |
| 7,829,585 B2 | 11/2010 | Nakamoto et al. |
| 7,932,272 B2 | 4/2011 | Nakamoto et al. |
| 2002/0011495 A1 | 1/2002 | Clemmons |
| 2003/0045554 A1 | 3/2003 | Sankaranarayanan |
| 2003/0114491 A1 | 6/2003 | Kim et al. |
| 2003/0191158 A1 | 10/2003 | Magee |
| 2004/0038239 A1 | 2/2004 | Tsukahara et al. |
| 2004/0044040 A1 | 3/2004 | Neubert et al. |
| 2004/0152730 A1 | 8/2004 | Farina et al. |
| 2004/0198773 A1 | 10/2004 | Hart et al. |
| 2005/0119229 A1 | 6/2005 | Ammermann et al. |
| 2006/0264419 A1 | 11/2006 | Schiemann et al. |
| 2006/0270637 A1 | 11/2006 | Gravestock et al. |
| 2007/0060619 A1 | 3/2007 | Burns et al. |
| 2007/0105904 A1 | 5/2007 | Tanaka et al. |
| 2007/0105943 A1 | 5/2007 | Nakamoto et al. |
| 2007/0167493 A1 | 7/2007 | Sankaranarayanan |
| 2008/0090846 A1 | 4/2008 | Bridger et al. |
| 2008/0275244 A1 | 11/2008 | Niijima et al. |
| 2009/0062348 A1 | 3/2009 | Nakamoto et al. |
| 2009/0082403 A1 | 3/2009 | Tanaka et al. |
| 2009/0227799 A1 | 9/2009 | Nakamoto et al. |
| 2009/0233883 A1 | 9/2009 | Matsukura |
| 2010/0105737 A1 | 4/2010 | Tanaka |
| 2010/0160379 A1 | 6/2010 | Tanaka et al. |
| 2010/0168173 A1 | 7/2010 | Tanaka et al. |
| 2010/0331282 A1 | 12/2010 | Matsukura |
| 2011/0195999 A1 | 8/2011 | Nakamoto et al. |

FOREIGN PATENT DOCUMENTS

| | | |
|---|---|---|
| EP | 0 124 067 A1 | 11/1984 |
| EP | 0 124 154 A2 | 11/1984 |
| EP | 0274867 A2 | 7/1988 |
| EP | 0 326 328 A2 | 8/1989 |
| EP | 0 414 386 A1 | 2/1991 |
| EP | 0533130 A1 | 3/1993 |
| EP | 0976744 A1 | 2/2000 |
| EP | 1 216 980 A1 | 6/2002 |
| EP | 1217000 A1 | 6/2002 |
| EP | 1 229 034 A1 | 8/2002 |
| EP | 1275301 A1 | 1/2003 |
| EP | 1275653 A1 | 1/2003 |
| EP | 1 369 420 A1 | 12/2003 |
| EP | 1 669 348 A1 | 6/2006 |
| EP | 1 782 811 | 5/2007 |
| EP | 1 944 303 A1 | 7/2008 |
| GB | 919073 | 2/1963 |
| JP | 54-2325 A | 1/1979 |
| JP | 59-073575 A | 4/1984 |
| JP | 59-206353 A | 11/1984 |
| JP | 61-148178 A | 7/1986 |
| JP | 64-3162 A | 1/1989 |
| JP | 1-246264 A | 10/1989 |
| JP | 3-66689 A | 3/1991 |
| JP | 3-161470 A | 7/1991 |
| JP | 5-213877 A | 8/1993 |
| JP | 5-294935 A | 11/1993 |
| JP | 7-25853 A | 1/1995 |
| JP | 8-12579 A | 1/1996 |
| JP | 8-175993 A | 7/1996 |
| JP | 9-507245 A | 7/1997 |
| JP | 10-505600 A | 6/1998 |
| JP | 11-152275 A | 6/1999 |
| JP | 2000-504336 A | 4/2000 |
| JP | 2000-178243 A | 6/2000 |
| JP | 2001-515464 A | 9/2001 |
| JP | 2001-522834 A | 11/2001 |
| JP | 2001-525365 A | 12/2001 |
| JP | 2001-525802 A | 12/2001 |
| JP | 2001-527083 A | 12/2001 |
| JP | 2002-275159 A | 9/2002 |
| JP | 2002-284766 A | 10/2002 |
| JP | 2002-537396 A | 11/2002 |
| JP | 2002-544162 A | 12/2002 |
| JP | 2003-506466 A | 2/2003 |
| JP | 2004-529154 A | 9/2004 |
| JP | 2005-033079 A | 2/2005 |
| JP | 2005-526751 A | 9/2005 |
| JP | 2006-519247 A | 8/2006 |
| WO | WO-86/03203 A1 | 6/1986 |
| WO | WO-93/12084 A1 | 6/1993 |
| WO | WO 95/09159 A1 | 4/1995 |
| WO | WO 95/18795 A1 | 7/1995 |
| WO | WO-96/09294 A1 | 3/1996 |
| WO | WO-97-27852 A1 | 8/1997 |
| WO | WO-97/28128 A1 | 8/1997 |
| WO | WO-98/25883 A1 | 6/1998 |
| WO | WO-98/50029 A1 | 11/1998 |
| WO | WO-99/24404 A1 | 5/1999 |
| WO | WO-99/48492 A1 | 9/1999 |
| WO | WO-99/50247 A1 | 10/1999 |
| WO | WO-00/07991 A1 | 2/2000 |
| WO | WO-00/51998 A1 | 9/2000 |
| WO | WO-00/62778 A1 | 10/2000 |
| WO | WO-00/73283 A1 | 12/2000 |
| WO | WO-01/11966 A1 | 2/2001 |
| WO | WO-01/21584 A1 | 3/2001 |
| WO | WO-01/25181 A1 | 4/2001 |
| WO | WO 01/26652 A1 | 4/2001 |
| WO | WO-01/27096 A1 | 4/2001 |
| WO | WO-01/51456 A2 | 7/2001 |
| WO | WO-01/53274 A1 | 7/2001 |
| WO | WO-01/74779 A1 | 10/2001 |
| WO | WO-02/00651 A2 | 1/2002 |
| WO | WO-02/04626 A1 | 1/2002 |
| WO | WO-02/06275 A1 | 1/2002 |
| WO | WO-02/22583 A2 | 3/2002 |
| WO | WO-02/060875 A1 | 8/2002 |
| WO | WO-02/060896 A1 | 8/2002 |
| WO | WO-02-060898 A1 | 8/2002 |
| WO | WO-02/083645 A1 | 10/2002 |
| WO | WO-02/085897 A1 | 10/2002 |
| WO | WO 03/006628 A2 | 1/2003 |
| WO | WO-03/027095 A1 | 4/2003 |
| WO | WO-03/031435 A1 | 4/2003 |
| WO | WO 03/037860 A2 | 5/2003 |
| WO | WO-03/045385 A1 | 6/2003 |
| WO | WO 03/045920 A1 | 6/2003 |
| WO | WO-03/059903 A2 | 7/2003 |
| WO | WO-03/068232 A1 | 8/2003 |
| WO | WO-03/068235 A1 | 8/2003 |
| WO | WO 03/068747 A1 | 8/2003 |
| WO | WO-03/091226 A1 | 11/2003 |
| WO | WO-03/091227 A1 | 11/2003 |
| WO | WO-2004/000813 A1 | 12/2003 |
| WO | WO-2004/014366 A1 | 2/2004 |
| WO | WO-2004/014370 A2 | 2/2004 |
| WO | WO-2004/029027 A1 | 4/2004 |
| WO | WO-2004/033432 A1 | 4/2004 |
| WO | WO-2004/048567 A2 | 6/2004 |
| WO | WO-2004/052280 A2 | 6/2004 |
| WO | WO-2004/089931 A1 | 10/2004 |
| WO | WO-2005/033079 A1 | 4/2005 |
| WO | WO-2006/016548 A1 | 2/2006 |
| WO | WO-2006/106711 A1 | 10/2006 |
| WO | WO-2007/052615 A1 | 5/2007 |
| WO | WO 2007/056215 A2 | 5/2007 |
| WO | WO-2009/084621 A1 | 7/2009 |
| WO | WO-2009081970 A1 | 7/2009 |

OTHER PUBLICATIONS

Extended European Search Report issued Apr. 18, 2011, in European Patent Application No. 08740624.5.

Chandran et al., "Synthesis of 8-Aminoquinolines: Part II—8-Guidance Derivatives," Journal of Scientific & Industrial Reserarch (1952), 11B, pp. 129-132.

U.S. Office Action issued May 14, 2010 for copending U.S. Appl. No. 11/887,249.

U.S. Office Action issued May 4, 2010 for copending U.S. Appl. No. 11/658,901.

2021278791 Chemcats, Akos Screening Library, Feb. 7, 2006, AKL-P-1720927, Pyridine, 3-[5-[(2-methoxyphenyl)methyl]-1,2,4-oxadiazol-3-yl]-434304-24-2.

Ikizler et al., "Antimicrobial Activities of some 4H-1,2,4-triazoles", Indian Journal of Pharmaceutical Science, 1999, vol. 61, No. 5, pp. 271-274.

Satyanarayana et al., "Studies on the synthesis and biological activity of 3-arylaminomethyl-5-(3-pyridyl)-1,3,4-oxadiazole-2-thione derivatives", Boll. Chim. Farmac., 2001, vol. 140. No. 4, pp. 228-232.

2025887145 Chemcats, Aurora Screening Library, Jan. 1, 2007, kbsa-0118093, Pyridine, 3-[5-[(4-methoxyphenyl)methyl]-1,2,4-oxadiazol-3-yl]-, 431922-54-2.

2020895193 Chemcats, Interchim Intermediates, Jul. 9, 2007, STK030913, Pyridine, 3-[3-[(4-methoxyphenyl)methyl]-1,2,4-oxadiazol-5-yl]-, 438574-99-3.

2036647688 Chemcats, Ambinter Stock Screening Collection, Jun. 1, 2007, STK143803, Pyridine, 3-[5-[(4-methoxyphenyl)methyl]-1,2,4-thiadiazol-2-yl]-, 794713-41-9.

AU 2003293376-A1 (Abstract Only).

Database Chemcats [Online] Chemical Abstracts Service, Columbus, Ohio, US; XP002600785 Database accession No. 2059288788 *Order No. 6700755* & Chembridge Corporation: "ChemBridge Screening Library" Jun. 9, 2010, ChemBridge Corporation, San Diego (USA).

Database Chemcats [Online] Chemical Abstracts Service, Columbus, Ohio, US; XP002600787 Database accession No. 2084604173 *Order No. STK143803* & Vitas-M: "Vitas-M Screening Collection" Jul. 13, 2010, Vitas-M, Hodynski Blv. 15, Moskow, (RU).

Database Registry [Online] Chemical Abstracts Service, Columbus, Ohio, US; Jul. 16, 2002, XP002600783 Database accession No. 43857-99-3(RN).

Database Registry [Online] Chemical Abstracts Service, Columbus, Ohio, US; Jun. 18, 2002, XP002600784 Database accession No. 431922-54-2(RN) *abstract*.

Database Registry [Online] Chemical Abstracts Service, Columbus, Ohio, US; Oct. 18, 2004, XP002600786 Database accession No. 764713-41-9(RN) *abstract*.

Extended European Search Report dated Oct. 11, 2010, issued in corresponding European Patent Application No. 07828273.8.

Guillory, "Generation of Polymorphs, Hydrates, Solvates, and Amorphous Solids", *Polymorphism in Pharmaceutical Solids*, ed. Harry G. Brittain, Marcel Dekker, Inc., New York, 1999, pp. 183-226.

Vippagunta et al., "Crystalline Solids", *Advanced Drug Delivery Reviews*, vol. 48, 2001, pp. 3-26.

Office Action from U.S. Appl. No. 10/573,890 dated Jul. 29, 2009.

Hata, "New Approaches to Antifungal Drugs for the Treatment of Fungal and Protozoal Infections, Ravuconazole and Beyond: New Targets and Pre-clinical Strategies," The SMI's 12th Annual Conference, Superbugs and Superdrugs, Mar. 18, 2010, Crowne Plaza London—St. James, 44 pages.

Lo et al., "Development of highly selective and sensitive probes for hydrogen peroxide," Communication Chem Comm, The Royal Society of Chemistry, 2003, pp. 2728-2729.

European Search Report issued Jul. 29, 2010, in corresponding European Patent Application No. 05768893.9.

Okawa et al., "Pyrido[2,3-d]pyrimidine Derivatives: Synthesis via the Intermolecular Aza-Wittig Reaction/Heterocyclization and the Crystal Structure," Synthesis, Database CA [Online] Chemical Abstract Service, XP002512524, Database accession No. 677971 (1998), pp. 1467-1475 (1998).

Gardner et al., "Genome sequence of the human malaria parasite Plasmodium falciparum," Nature, vol. 419, pp. 498-511, (2002).

Naik et al., "Glucosamine Inhibits Inositol Acylation of the Glycosylphosphatidylinositol Anchors in Intraerythrocytic Plasmodium falciparuml," The Journal of Biological Chemistry, vol. 278, No. 3, pp. 2036-2042, (2003).

Shinkai et al., "N-Acylphenylalanines and Related Compounds. A New Class of Oral Hypoglycemic Agents," J. Med. Chem., vol. 31, pp. 2092-2097, (1988).

Ohshima et al., "Non-Prostanoid Thromboxane A2 Receptor Antagonists with a Dibenzoxepin Ring System. 2," J. Med. Chem., vol. 35, pp. 3402-3413, (1992).

An Office Action from co-pending U.S. Appl. No. 11/589,128, mailed May 7, 2009.

Chan et al., Database Accession No. 8422493, Abstract, Bioorganic & Medicinal Chemistry Letters, 1999, pp. 2583-2586., vol. 9, No. 17, Database Crossfire Bellstein, Bellstein Institut Zur Foerderung Der Chemischen Wissenschaften, Frankfurt Am Main, DE, XP-002512523.

Kajino et al., "Preparation and formulation of quinazoline derivatives as allergy inhibitors", Database CA [Online], Chemical Abstract Service; XP002512525, Database Accession No. 216905, 1999.

Piechaczak et al., "Monoamine oxidase inhibitors VII. Derivatives of quinolinecarboxylic acids," Database Accession No. 1996:75701, Abstract, Acta Poloniae Pharmaceutica, vol. 23, No. 1, pp. 7-13, 1966, XP002512526.

Modena et al.: "Plant growth regulating activities of 2-[2-(arylamino)-2-oxoethyl]benzoic acids", Database Accession No. 1993:597690, Abstract, Farmaco, vol. 48, No. 4, pp. 567-572, 1993, XP002512527.

Ishikawa et al., "TAK-599, a Novel N-Phosphono Type Prodrug of Anti-MRSA Cephalosporin T-91825: Synthesis, Physicochemical and Pharmacological Properties," Bioorganic & Medicinal Chemistry, vol. 11, pp. 2427-2437, (2003).

Supplementary European Search Report dated Feb. 6, 2009 for corresponding European Application No. 04788159.4.

International Search Report date May 20, 2008 for corresponding International Application No. PCT/JP2008/057851.

Connors et al., "Prodrugs in medicine," Overview Biologicals & Immunologicals, Exp. Opin. Ther. Patents, vol. 5, No. 9, 1995, pp. 873-885.

Chang, K. Y. et al., "Synthesis and Structure-Activity Relationships of Quaternary Ammonium Cephalosporins with 3-Pyrazolylpyridinium Derivatives," Bioorganic & Medicinal Chemistry Letters (2000) vol. 10, No. 11, pp. 1211-1214.

Plate, R. et al., "Synthesis and Muscarinic Activities of 3-(Pyrazolyl)-1,2,5,6-tetrahydropyridine Derivatives," Bioorganic & Medicinal Chemistry Letters (1996) vol. 10, No. 2, pp. 227-237.

Vrzheschch, P. V. et al., "Supercooperativity in platelet aggregation: Substituted pyridyl isoxazoles, a new class of supercooperative platelet aggregation inhibitors," FEBS Letters (1994) vol. 351, No. 2, pp. 168-180.

Lukevics, E. et al., "Synthesis and cytotoxicity of silyl- and carbonyl-substituted isoxazoles," Chemistry of Heterocyclic Compounds (2000) vol. 36, No. 10, pp. 1226-1231.

Freshney et al., Culture of Animal Cells, A Manual of Basic Technique, 1983, Wiley & Sons, Inc., New York pp. 7-9.

Office Action issued Jun. 17, 2011, in related U.S. Appl. No. 12/109,834.

English language machine generated translation for JP-7-25853-A, dated Jan. 27, 1995.

Japanese Office Action, dated Aug. 6, 2010, for Japanese Patent Application No. 2005-514417.

US Office Action, dated Oct. 13, 2010, for U.S. Appl. No. 11/658,901.

Chan et al., "Discovery of 1,6-Naphthylridines as a Novel Class of Potent and Selective Human Cytomegalovirus Inhibitors," Journal of Medicinal Chemistry (1999), vol. 42, No. 16, pp. 3023-3025.

Kushner et al., "Experimental Chemotherapy of Tuberculosis. II. The Synthesis of Pyrazinamides and Related Compounds," Journal of the American Chemical Society (1952), vol. 74, pp. 3617-3621.

Lucas et al., "Facile Synthesis of a Library of 9-Alkyl-8-benzyl-9H-purin-6-ylamine Derivatives," Journal of Combinatorial Chemistry (2001), vol. 3, No. 6, pp. 518-520.

Tanaka et al., "An Effective Synthesis of a (Pyridin-3-yl)isoxazole via 1,3-Dipolar Cycloaddition Using ZnCl2: Synthesis of a (2-Aminopyridin-3-yl)isoxazole Derivative and its Antifungal Activity," Chemistry Letters, vol. 39, No. 10, pp. 1033-1035, The Chemical Society of Japan, Oct. 5, 2010.

European Search Report issued Jul. 19, 2010, in corresponding European Patent Application No. 06730370.1.

Pernak, J. et al., "Synthesis and antimicrobial activities of new pyridinium and benzimidazolium chlorides," Eur. J. Med. Chem., vol. 36 (2001) pp. 313-320.

Pregnolato, M. et al., "3H-[1,2]Dithiolo[3,4-b]pyridine-3-thione and its derivatives Synthesis and antimicrobial activity," IL FARMACO, vol. 55, (2000) pp. 669-679.

International Search Report issued Nov. 13, 2007, PCT International Application No. PCT/JP2007/068230.

Response filed Apr. 8, 2011, in response to Communication Pursuant to Rule 70(2) and 70a(2) and Extended European Search Report in European Patent Application No. 07 828 273.8.

English translation of International Preliminary Report on Patentability issued Mar. 24, 2009, in PCT International Application No. PCT/JP2007/068230.

English translation of International Search Report issued Nov. 13, 2007, in PCT International Application No. PCT/JP2007/068230.

International Preliminary Report on Patentability issued Mar. 24, 2009, in PCT International Application No. PCT/JP2007/068230.

International Search Report issued Nov. 13, 2007, in PCT International Application No. PCT/JP2007/068230.

Nakamoto et al., "Synthesis and Evaluation of New Nicotinamide Derivative Antifungals Acting via Glycosylphosphatidylinositol (GPI) . . . ," 8th AFMC International Medicinal Chemistry Symposium Nov. 29-Dec. 2, 2011, Tokyo.

Office Action issued Oct. 20, 2011, Indian Patent Application No. 3678/DELNP/2008.

PYRIDINE DERIVATIVE SUBSTITUTED BY HETEROARYL RING, AND ANTIFUNGAL AGENT COMPRISING THE SAME

This application is the National Phase of PCT/JP2007/068230 filed on Sep. 20, 2007, which claims priority under 35 U.S.C. 119(e) to U.S. Provisional Application No. 60/848,359 filed on Oct. 2, 2006, and under 35 U.S.C. 119(a) to Patent Application No. 2006-256094 filed in JAPAN on Sep. 21, 2006, respectively, all of which are hereby expressly incorporated by reference into the present application.

TECHNICAL FIELD

The present invention relates to novel pyridine derivatives substituted by heteroaryl ring, and to antifungal agents comprising these derivatives.

BACKGROUND ART

Recent years have witnessed an increase in the number of patients, and their age, with diminished immune function due to advanced chemotherapy and the sort, so there has been increasing importance placed on how to deal with opportunistic infection. As indicated by the fact that opportunistic infections are increasingly being caused by different attenuated viruses, the problem of infection will not go away as long as there is a basic disease that lowers the resistance of a patient. Therefore, a new way of dealing with infection that includes the problem of drug resistance is being viewed as one of the most important issues facing our aging society that looms near on the horizon.

In the field of antifungal agents, in the past, for example, polyene-based amphotericin B, azole-based fluconazole, itraconazole, voriconazole, and the like have been developed for treatment of latent fungal infections. Most of the existing drugs already on the market have a similar mechanism, and the appearance of azole-resistant fungi and so forth is currently becoming a problem.

Cyclic hexapeptide-based caspofungin, micafungin, and the like based on natural substances have been developed in recent years as 1,3-β-glucan synthetase enzyme inhibitors with a novel mechanism, but these pharmaceuticals can only be administered by injection, so they are still not satisfactory as an antifungal agent.

Under these situations, in which existing antifungal agents are inadequate, there is a need for the development of a safe pharmaceutical based on a novel mechanism. Related art relating to antifungal agents based on such a novel mechanism include Patent Documents 1 and 2. Patent Documents 1 and 2 describe pyridine derivatives that exhibit an effect against the onset, progress, and persistence of infection, by inhibiting the process of transport of GPI (glycosylphosphatidyl-inositol) anchor proteins to the cellular wall and thereby inhibiting the onset of cellular wall surface-layer proteins, inhibiting the onset of cellular wall assembly, and inhibiting the adhesion of fungi to cells, so that the pathogen cannot manifest its pathogenicity.

However, the compound groups disclosed in Patent Document 1 have a 2-benzylpyridine as a common structure, and are clearly different structurally from the compounds according to the present invention. Furthermore, a problem with the compound groups disclosed in Patent Document 1 is that, although they exhibit activity in vitro, they are readily metabolized in the body. Also, while the compound groups disclosed in Patent Document 2 exhibit excellent antifungal activity, they have the structure represented by the following formula:

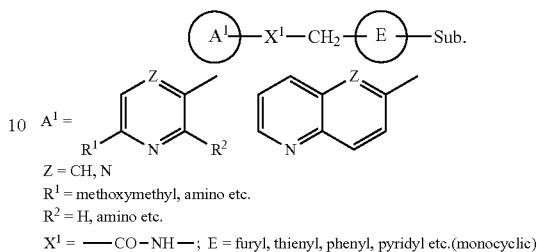

$A^1 =$ $Z = CH, N$
$R^1 = $ methoxymethyl, amino etc.
$R^2 = $ H, amino etc.
$X^1 = $ —CO—NH—; E = furyl, thienyl, phenyl, pyridyl etc.(monocyclic)

and even with compounds having a pyridine ring skeleton, said compound groups are clearly different structurally from the compounds according to the present invention in that their common structure is that they are bonded with a monocycle at the 3-position of the pyridine ring, using an amidomethylene group as a linker.

Patent Documents 3 to 5 are examples of prior art that is structurally similar to the compounds according to the present invention. Patent Document 3 describes a pyridine derivative substituted with a tetrazole ring, which is used as an anticancer agent based on the inhibitory action of a lyase enzyme; Patent Document 4 describes a pyridine derivative substituted with a triazole ring, which is used as an NK-1 receptor antagonist; and Patent Document 5 describes a pyridine derivative substituted with a tetrazole ring, which is used to treat chronic rheumatoid arthritis or degenerative arthritis, based on the inhibitory action of matrix metalloproteinase.

However, Patent Documents 3 to 5 do not describe the compounds according to the present invention, and Patent Documents 3 to 5 disclose nothing whatsoever regarding any antifungal action against *Candida, Aspergillus, Cryptococcus*, or other such fungi that are common in human fungal infection.

Patent Document 1: International Publication Pamphlet 02/04626
Patent Document 2: International Publication Pamphlet 05/033079
Patent Document 3: International Publication Pamphlet 03/027095
Patent Document 4: International Publication Pamphlet 03/091226
Patent Document 5: International Publication Pamphlet 04/014366

DISCLOSURE OF INVENTION

Problems to be Solved by the Invention

It is an object of the present invention to provide an antifungal agent that has excellent antifungal action which is not exist in conventional antifungal agents, and is also excellent in terms of its properties, safety, and metabolic stability.

Means for Solving the Problems

As a result of diligent research conducted in light of the above situations, the inventors succeeded in synthesizing novel pyridine derivatives (hereinafter referred to as "compounds of the present invention") represented by the following formula I:

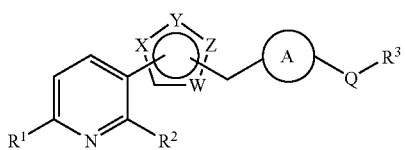

(I)

and characterized by a chemical structure in which a 5- or 6-membered heteroaryl ring or a benzene ring is bonded using a 5-membered heteroaryl ring as a linker, and perfected the present invention upon discovering that these compounds exhibit an outstanding antifungal action.

Specifically, the present invention provides the following.

(1) A compound represented by the following formula I or a salt thereof:

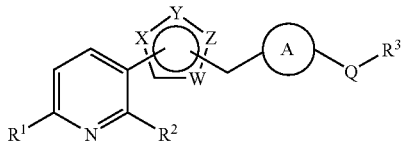

(I)

wherein $R^1$ represents a hydrogen atom, a halogen atom, an amino group, a $C_{1-6}$ alkyl group, a $C_{1-6}$ alkoxy group, or a $C_{1-6}$-alkoxy-$C_{1-6}$-alkyl group;

$R^2$ represents a hydrogen atom or an amino group;

X, Y, Z, and W independently represent a nitrogen atom, an oxygen atom, a sulfur atom, or —CH—, provided that at least two among X, Y, and W are nitrogen atoms;

the ring A represents a 5- or 6-membered heteroaryl ring or a benzene ring;

Q represents a methylene group, an oxygen atom, —CH$_2$O—, —OCH$_2$—, —NH—, —NHCH$_2$—, or —CH$_2$NH—;

$R^3$ represents a $C_{1-6}$ alkyl group, a $C_{3-8}$ cycloalkyl group, a $C_{6-10}$ aryl group, or a 5- or 6-membered heteroaryl group, each of which may have one or two substituent(s) selected from among a substituent group α; and pyrazole rings are excluded from among 5-membered heteroaryl rings including X, Y, Z, and W;

Substituent Group α a halogen atom, a $C_{1-6}$ alkyl group, a $C_{1-6}$ alkoxy group, a $C_{3-8}$ cycloalkyl group, a $C_{2-6}$ alkenyl group, and a $C_{2-6}$ alkynyl group.

(2) The compound or the salt thereof according to (1) above, wherein a partial structure represented by the following formula II:

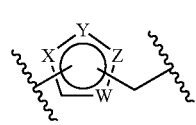

(II)

of the compound represented by the following formula I:

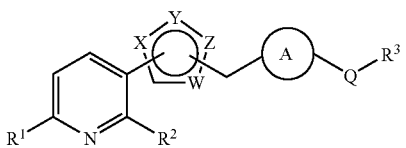

(I)

is a partial structure selected from the following group.

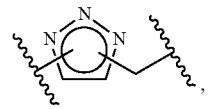

(III)

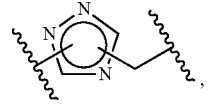

(IV)

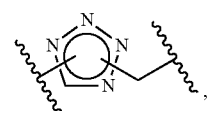

(V)

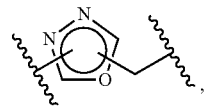

(VI)

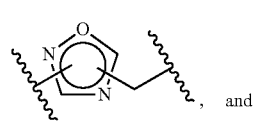

, and (VII)

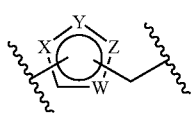

(VIII)

(3) The compound or the salt thereof according to (1) above, wherein the partial structure represented by the following formula II:

(II)

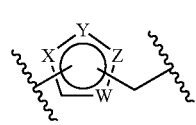

of the compound represented by the following formula I:

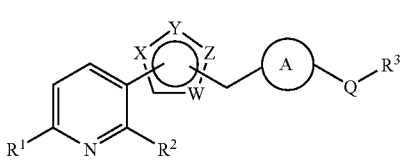

(I)

is a partial structure represented by formula V.

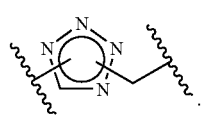
(V)

(4) The compound or the salt thereof according to (3) above, wherein the partial structure represented by the following formula II:

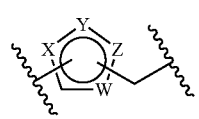
(II)

of the compound represented by the following formula I:

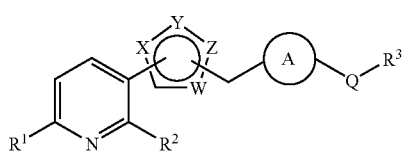
(I)

is a partial structure represented by formula v.

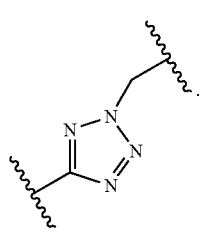
(v)

(5) The compound or the salt thereof according to (1) above, wherein the partial structure represented by the following formula II:

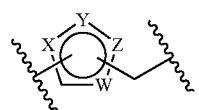
(II)

of the compound represented by the following formula I:

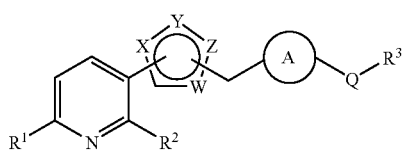
(I)

is a partial structure represented by the following formula III:

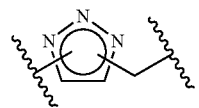
(III)

or is a partial structure represented by the following formula IV:

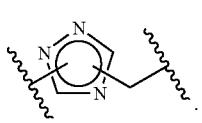
(IV)

(6) The compound or the salt thereof according to (5) above, wherein the partial structure represented by the following formula II:

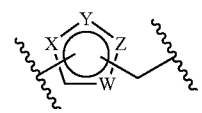
(II)

of the compound represented by the following formula I:

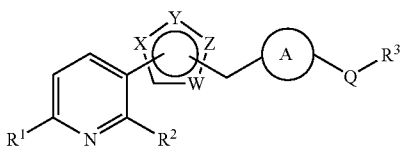
(I)

is a partial structure selected from the following group.

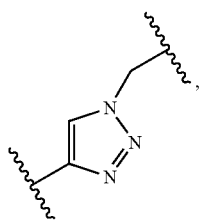
(iii-a)

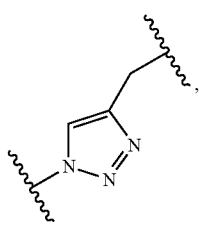
(iii-b)

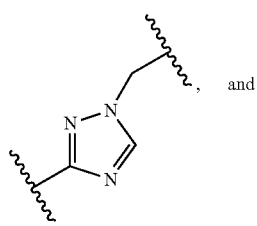 (iv-a)

and

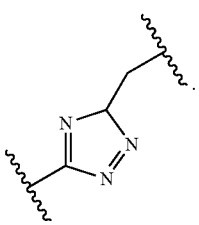 (iv-b)

(7) The compound or the salt thereof according to (1) above, wherein the partial structure represented by the following formula II:

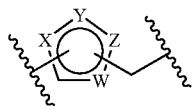 (II)

of the compound represented by the following formula I:

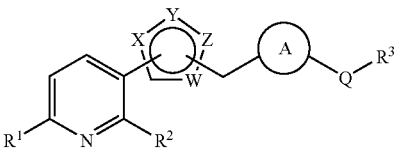 (I)

is a partial structure selected from the following group.

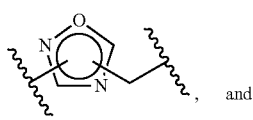 (VI)

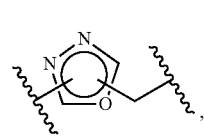 (VII)

and

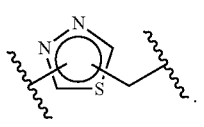 (VIII)

(8) The compound or the salt thereof according to (7) above, wherein the partial structure represented by the following formula II:

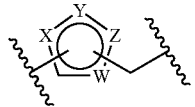 (II)

of the compound represented by the following formula I:

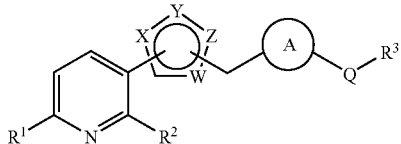 (I)

is a partial structure selected from the following group.

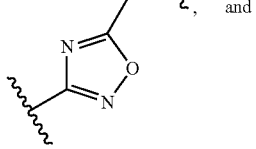 (vi)

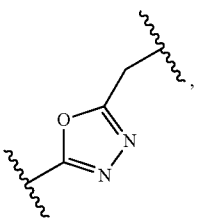 (vii)

and

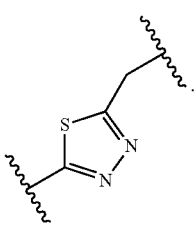 (viii)

(9) The compound or the salt thereof according to any one of (1) to (8) above,
wherein $R^2$ represents an amino group.

(10) The compound or the salt thereof according to (9) above, wherein $R^1$ represents a hydrogen atom, an amino group, or a $C_{1-6}$-alkoxy-$C_{1-6}$-alkyl group.

(11) The compound or the salt thereof according to any one of (1) to (8) above, wherein $R^1$ represents an amino group, and $R^2$ represents a hydrogen atom.

(12) The compound or the salt thereof according to any one of (1) to (11) above, wherein the ring A represents a pyridine ring, a benzene ring, a furan ring, a thiophene ring, or a pyrrole ring.

(13) The compound or the salt thereof according to (12) above, wherein the ring A represents a pyridine ring or a benzene ring.

(14) The compound or the salt thereof according to any one of (1) to (13) above, wherein Q represents an oxygen atom, —CH$_2$O—, or —OCH$_2$—.

(15) A pharmaceutical composition comprising the compound or the salt thereof according to any one of (1) to (14) above.

(16) A medicament comprising the compound or the salt thereof according to any one of (1) to (14) above.

(17) An antifungal agent comprising the compound or the salt thereof according to any one of (1) to (14) above as an active ingredient.

(18) A method for preventing and/or treating fungal infection by administering a pharmaceutically effective amount of the compound or the salt thereof according to any one of (1) to (14) above.

(19) A use of the compound or the salt thereof according to any one of (1) to (14) above to manufacture an antifungal agent.

Advantageous Effects Of The Invention

The compound or a salt thereof of the present invention 1) inhibits the onset of cellular wall surface-layer proteins by inhibition of fungal GPI biosynthesis, inhibits cellular wall assembly, and inhibits the adhesion of fungi to cells, so that the pathogen cannot manifest its pathogenicity, and thereby exhibits an effect against the onset, progress, and persistence of infections, and 2) is excellent in terms of its properties, safety, and metabolic stability, making this compound extremely useful as an agent for preventing or treating fungal infections.

BEST MODE FOR CARRYING OUT THE INVENTION

The present invention will now be described in detail by giving embodiments, etc., of the present invention, as well as definitions of the symbols, terms, etc., used in this Specification.

In this Specification, the structural formulas of compounds only express a specific isomer for the sake of convenience, but the present invention encompasses all geometric isomers that can be produced in the structure of the compound, optical isomers based on asymmetric carbons, stereoisomers, rotary isomers, tautomers, and other such isomers and isomer mixtures, and is not limited by giving formulas for the sake of convenience, and may be any isomer or mixture. Therefore, the compound of the present invention may have asymmetric carbon atoms in its molecule, and optically active isomers and racemic modifications may be present, and all of these are included in the present invention without limitations. Also, there may be crystalline polymorphism, but similarly there are no limitations on this, and the compound may be in the form of a single crystal form, or may be a mixture composed of two or more crystal forms. The compound of the present invention also encompasses anhydrides, hydrates, and other such solvates.

The scope of the present invention also encompasses compounds produced by oxidation, reduction, hydrolysis, conjugation, and other forms of metabolism in the body (so-called metabolites), and compounds that produce the present invention compound by undergoing oxidation, reduction, hydrolysis, conjugation, and other forms of metabolism in the body (so-called prodrugs).

The term "$C_{1-6}$ alkyl group" used in this Specification means a linear or branched alkyl group with 1 to 6 carbons, which is a monovalent group derived by removing any one hydrogen atom from an aliphatic hydrocarbon with 1 to 6 carbons. Specific examples thereof may include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, an n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, and a 1-ethyl-2-methylpropyl group, with a methyl group, an ethyl group, an n-propyl group, an isopropyl group, an n-butyl group, an isobutyl group, a sec-butyl group, a tert-butyl group, and so forth being preferable.

The term "$C_{2-6}$ alkenyl group" used in this Specification means a linear or branched alkenyl group with 2 to 6 carbons, which may include 1 or 2 double bonds. Specific examples thereof may include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, and a hexanedienyl group, with an ethenyl group, a 1-propenyl group, a 2-propenyl group, a 1-butenyl group, a 2-butenyl group, a 3-butenyl group, a 2-methyl-1-propenyl group, a 3-methyl-2-butenyl group, and so forth being preferable.

The term "$C_{2-6}$ alkynyl group" used in this Specification means a linear or branched alkynyl group with 2 to 6 carbons, which may include 1 or 2 triple bonds. Specific examples thereof may include an ethynyl group, a 1-propynyl group, a 2-propynyl group, a 1-butynyl group, a 2-butynyl group, a 3-butynyl group, a pentynyl group, a hexynyl group, and a hexanediynyl group, with an ethynyl group, a 1-propynyl group, a 2-propynyl group, a 1-butynyl group, a 2-butynyl group, a 3-butynyl group, and so forth being preferable.

The term "$C_{3-8}$ cycloalkyl group" used in this Specification means a cyclic aliphatic hydrocarbon group with 3 to 8 carbons. Specific examples thereof may include a cyclopropyl group, a cyclobutyl group, a cyclopentyl group, a cyclohexyl group, a cycloheptyl group, and a cyclooctyl group, with a cyclopropyl group, a cyclobutyl group, a cyclopentyl group, a cyclohexyl group, and so forth being preferable.

The term "$C_{1-6}$ alkoxy group" used in this Specification means a group in which an oxygen atom is bonded to the terminal of the "$C_{1-6}$ alkyl group" defined above. Specific examples thereof may include a methoxy group, an ethoxy group, an n-propoxy group, an isopropoxy group, an n-butoxy group, an isobutoxy group, a sec-butoxy group, a tert-butoxy group, an n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, an n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, 1,2,2-trimethylpropoxy group, a 1-ethyl-1-methylpropoxy group, and a 1-ethyl-2-methylpropoxy group, with a methoxy group, an ethoxy group, an n-propoxy group, an isopropoxy group, an n-butoxy group, an isobutoxy group, a sec-butoxy group, a tert-butoxy group, and so forth being preferable.

The term "$C_{6-10}$ aryl group" used in this Specification means an aromatic hydrocarbon cyclic group with 6 to 10 carbons. Specific examples thereof may include a phenyl group, a 1-naphthyl group, a 2-naphthyl group, an indenyl group, an azulenyl group, and a heptalenyl group, with a phenyl group, a 1-naphthyl group, a 2-naphthyl group, and so forth being preferable.

The term "$C_{1-6}$-alkoxy-$C_{1-6}$-alkyl group" used in this Specification means a group in which any hydrogen atom in the "$C_{1-6}$ alkyl group" defined above has been substituted with the "$C_{1-6}$ alkoxy group" defined above. Specific examples thereof may include a methoxymethyl group, an ethoxymethyl group, an n-propoxymethyl group, a methoxyethyl group, and an ethoxyethyl group.

The term "halogen atom" used in this Specification means a fluorine atom, a chlorine atom, a bromine atom, or an iodine atom.

The term "hetero atom" used in this Specification means a nitrogen atom, a sulfur atom, or an oxygen atom.

The term "5- or 6-membered heteroaryl ring" used in this Specification means an aromatic ring in which 5 or 6 atoms make up the ring and which contains one or more hetero atoms among the atoms that make up the ring. Specific examples thereof may include a furan ring, a thiophene ring, a pyrrole ring, a pyridine ring, a pyrazine ring, a pyridazine ring, a pyrimidine ring, a triazole ring (a 1,2,3-triazole ring, a 1,2,4-triazole ring, etc.), a tetrazole ring (such as a 1H-tetrazole ring or a 2H-tetrazole ring), a thiazole ring, a pyrazole ring, an oxazole ring, an isoxazole ring, an isothiazole ring, an oxadiazole ring, and a thiadiazole ring.

The term "5- or 6-membered heteroaryl group" used in this Specification means a monovalent group in which five or six atoms make up a ring, and which is derived by removing a hydrogen atom from any position on an aromatic ring containing one or more hetero atoms among the atoms that make up the ring. Specific examples thereof may include a furyl group (such as a 2-furyl group or a 3-furyl group), a thienyl group (such as a 2-thienyl group or a 3-thienyl group), a pyrrolyl group (such as a 1-pyrrolyl group, a 2-pyrrolyl group, or a 3-pyrrolyl group), a pyridyl group (such as a 2-pyridyl group, a 3-pyridyl group, or a 4-pyridyl group), a pyradinyl group, a pyridazinyl group (such as a 3-pyridazinyl group or a 4-pyridazinyl group), a pyrimidinyl group (such as a 2-pyrimidinyl group, a 4-pyrimidinyl group, or a 5-pyrimidinyl group), a triazolyl group (such as a 1,2,3-triazolyl group or a 1,2,4-triazolyl group), a tetrazolyl group (such as a 1H-tetrazolyl group or a 2H-tetrazolyl group), a thiazolyl group (such as a 2-thiazolyl group, a 4-thiazolyl group, or a 5-thiazolyl group), a pyrazolyl group (such as a 3-pyrazolyl group or a 4-pyrazolyl group), an oxazolyl group (such as a 2-oxazolyl group, a 4-oxazolyl group, or a 5-oxazolyl group), an isoxazolyl group (such as a 3-isoxazolyl group, a 4-isoxazolyl group, or a 5-isoxazolyl group), an isothiazolyl group (such as a 3-isothiazolyl group, a 4-isothiazolyl group, or a 5-isothiazolyl group), an oxadiazolyl group, and a thiadiazolyl group.

The phrase "may have one or two substituents" used in this Specification means that substitutable positions may have one or two substituents in any combination.

Next, variable groups in the compound of the present invention represented by formula I will be described. $R^1$ represents a hydrogen atom, a halogen atom, an amino group, a $C_{1-6}$ alkyl group, a $C_{1-6}$ alkoxy group, or a $C_{1-6}$-alkoxy-$C_{1-6}$-alkyl group, preferably a hydrogen atom, a $C_{1-6}$ alkyl group, an amino group, or a $C_{1-6}$-alkoxy-$C_{1-6}$-alkyl group.

Said $C_{1-6}$ alkyl group is preferably a methyl group, and said $C_{1-6}$-alkoxy-$C_{1-6}$-alkyl group is preferably a methoxymethyl group.

$R^2$ represents a hydrogen atom or an amino group.

Each of X, Y, Z, and W independently represents a nitrogen atom, an oxygen atom, a sulfur atom, or —CH—, provided that at least two among X, Y, and W are nitrogen atoms. The ring including X, Y, Z, and W represents a 5-membered heteroaryl ring.

However, pyrazole rings are excluded from among 5-membered heteroaryl rings including X, Y, Z, and W.

More specifically, the partial structure represented by the following formula II:

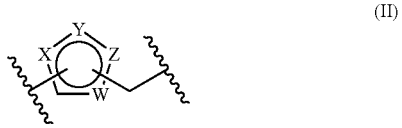

(II)

including X, Y, Z, and W is preferably any of the structures represented by the following.

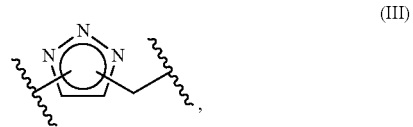

(III)

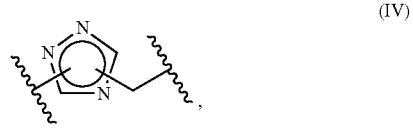

(IV)

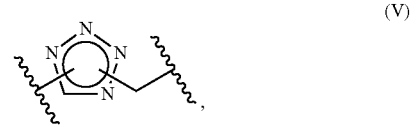

(V)

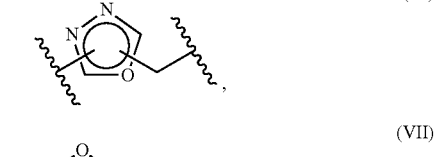

(VI)

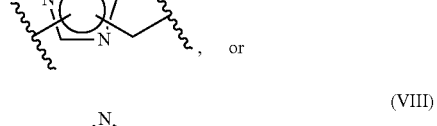

(VII)

, or

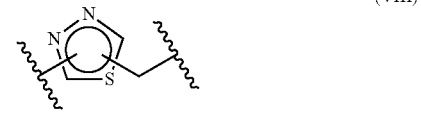

(VIII)

A partial structure represented by the following is more preferable.

(iii-a)
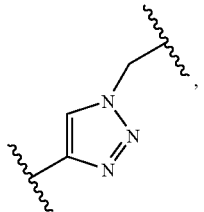

(iii-b)
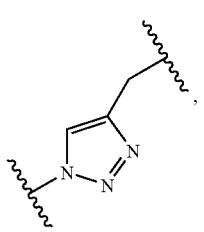

(iv-a)
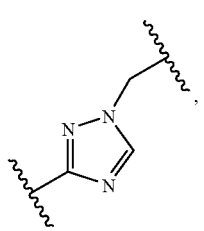

(iv-b)
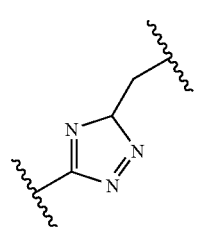

(v)
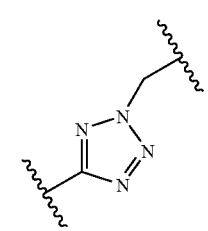

(vi)
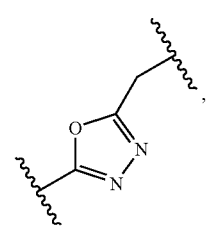

(vii)
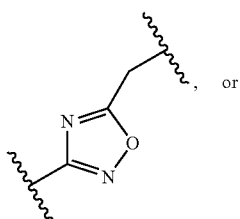, or (viii)
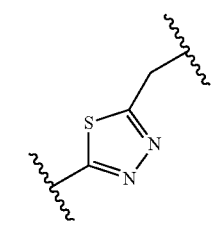

It is known that a partial structure represented by the formula iv-b:

(iv-b)
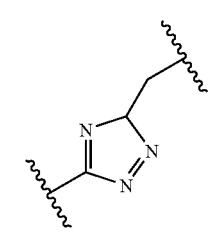

assumes the following equilibrium state.

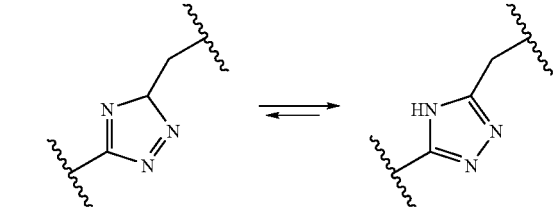

(iv-b)　　　　　(iv-b′)

In this Specification, the partial structure represented by formula iv-b shall also include the equilibrium state of the above formula iv-b'.

The partial structures represented by formula II including X, Y, Z, and W:

(II)
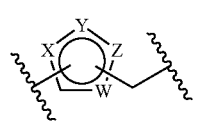

can be divided into the following three groups based on the type and number of X, Y, Z, and W.

The first group is when X, Y, Z, and W are all a nitrogen atom, and the partial structure represented by the following formula II:

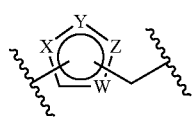
(II)

is represented by formula V:

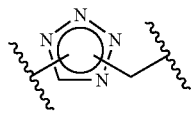
(V)

and a partial structure represented by formula v is especially favorable.

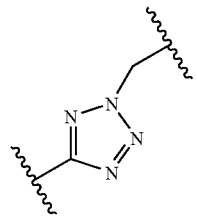
(v)

The second group is when three of X, Y, Z, and W are nitrogen atoms and the other one is —CH—, and the partial structure represented by the following formula II:

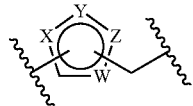
(II)

is a partial structure represented by formula III:

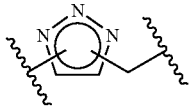
(III)

or is a partial structure represented by formula IV:

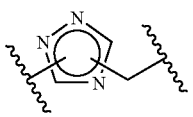
(IV)

Of these, a partial structure selected from among the following group is preferred.

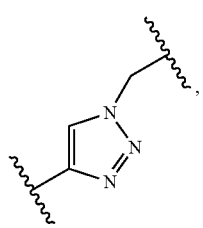
(iii-a)

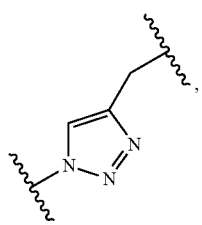
(iii-b)

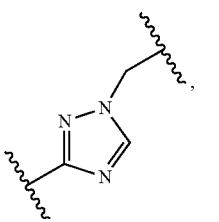
(iv-a)

and

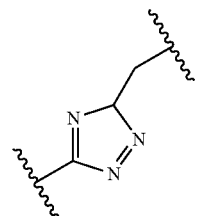
(iv-b)

In particular, a partial structure represented by formula iii-a is preferable.

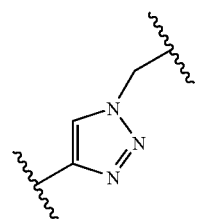
(iii-a)

The third group is when two of X, Y, Z, and W are nitrogen atoms, one is an oxygen atom or a sulfur atom, and the other one is —CH—. Of these, the partial structure represented by the following formula II:

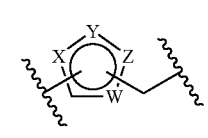
(II)

is preferably a partial structure selected from the following group:

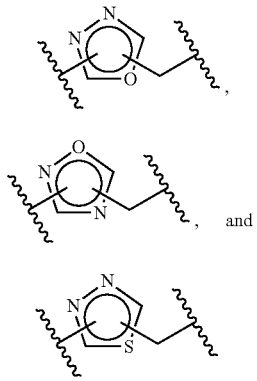

(VI)

(VII), and (VIII)

and more preferably a partial structure selected from the following group:

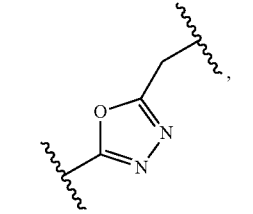

(vi),

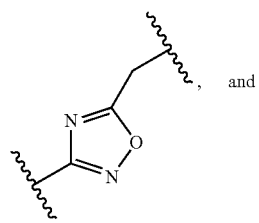

(vii), and

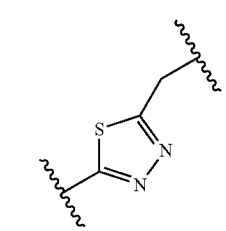

(viii)

The partial structure represented by formula vi:

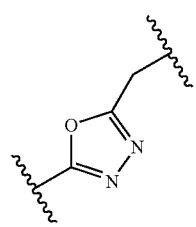

(vi)

and the partial structure represented by formula viii:

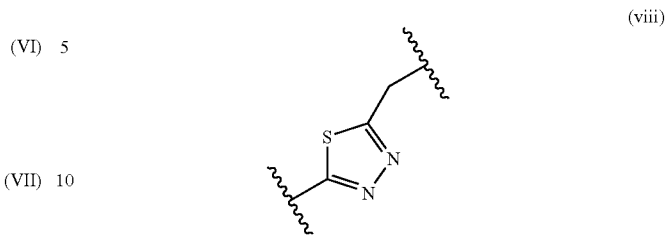

(viii)

are particularly favorable.

It is preferable if the 5-membered heteroaryl ring including X, Y, Z, and W is such that the left end is bonded to the 3-position of a pyridine ring via a single bond, and the right end is bonded to the ring A via a methylene group.

For example, if the 5-membered heteroaryl ring including X, Y, Z, and W is a tetrazole ring, and the partial structure represented by the following formula II:

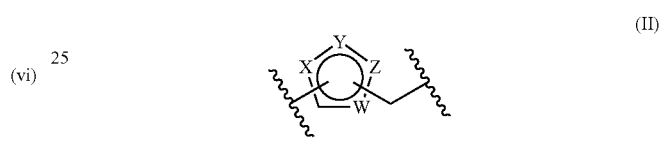

(II)

has a structure represented by the following formula v:

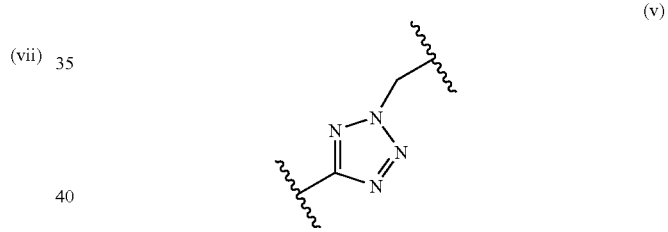

(v)

then the structure of the present invention compound is as represented by the following formula:

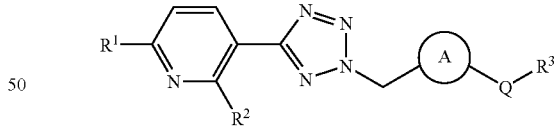

The ring A represents a 5- or 6-membered heteroaryl ring or benzene ring, with a pyridine ring, a benzene ring, a furan ring, a thiophene ring, or a pyrrole ring being preferable, a pyridine ring, a benzene ring, or a thiophene ring being more preferable, and a pyridine ring or a benzene ring being even more preferable.

Q represents a methylene group, an oxygen atom, —CH$_2$O—, —OCH$_2$—, —NH—, —NHCH$_2$—, or —CH$_2$NH—, of which a methylene group, an oxygen atom, —CH$_2$O—, or —OCH$_2$— is preferable, and an oxygen atom, —CH$_2$O—, or —OCH$_2$— is more preferable.

R$^3$ represents a C$_{1-6}$ alkyl group, a C$_{3-8}$ cycloalkyl group, a C$_{6-10}$ aryl group, or a 5- or 6-membered heteroaryl group, each of which may have one or two substituents selected from among a substituent group α.

Substituent Group α a halogen atom, a $C_{1-6}$ alkyl group, a $C_{1-6}$ alkoxy group, a $C_{3-8}$ cycloalkyl group, a $C_{2-6}$ alkenyl group, and a $C_{2-6}$ alkynyl group.

Examples of $R^3$ may include an ethyl group, an n-butyl group, a cyclopropyl group, a phenyl group, a fluorophenyl group, a furyl group, a chlorofuryl group, a methylfuryl group, a thienyl group, a bromothienyl group, a methylthienyl group, a pyridyl group, and a methylpyridyl group. Favorable examples of the substituents that may be had by $R^3$ and that are selected from Substituent Group α may include fluoro, chloro, bromo, and methyl groups.

$R^3$ is preferably an ethyl group, an n-butyl group, a phenyl group, a fluorophenyl group, a furyl group, a chlorofuryl group, a bromothienyl group, a methylthienyl group, or a pyridyl group.

The substituents of the ring A can be constituted by any combination of Q and $R^3$. Favorable examples of $R^3$-Q- serving as the substituent of the ring A thus constituted may include a benzyl group, a phenoxy group, a phenoxymethyl group, a benzyloxy group, a 2-fluoro-benzyloxy group, a 3-fluoro-benzyloxy group, a 4-fluoro-benzyloxy group, a 4-fluoro-phenoxy group, a 5-chloro-furan-2-ylmethyl group, a 5-methyl-furan-2-ylmethyl group, a 5-bromo-thiophen-2-ylmethyl group, a 5-methyl-thiophen-2-ylmethyl group, a pyridin-2-ylmethyl group, a 6-methyl-pyridin-2-yloxymethyl group, a pyridin-2-ylmethoxy group, a 6-methyl-pyridin-2-ylmethoxy group, a 4-methyl-pyridin-2-ylmethoxy group, an ethoxy group, a butoxy group, a butoxymethyl group, and a cyclopropylmethoxy group, of which a benzyl group, a phenoxy group, a phenoxymethyl group, a benzyloxy group, a 4-fluoro-phenoxy group, a 5-chloro-furan-2-ylmethyl group, a 5-methyl-furan-2-ylmethyl group, a 5-bromo-thiophen-2-ylmethyl group, a 5-methyl-thiophen-2-ylmethyl group, a pyridin-2-yloxymethyl group, a pyridin-2-ylmethoxy group, an ethoxy group, a butoxy group, or a butoxymethyl group is preferable.

Examples of the term "salt" used in this Specification may include a salt with an inorganic acid, a salt with an organic acid, and a salt with an acidic amino acid. Among these salts, pharmaceutically acceptable salts are preferred. Salts of the compound of the present invention encompass anhydrides, hydrates, and other such solvates of these salts.

Preferable examples of salts of inorganic acids may include salts of hydrochloric acid, hydrobromic acid, sulfuric acid, nitric acid, and phosphoric acid. Preferable examples of salts of organic acids include salts of acetic acid, succinic acid, fumaric acid, maleic acid, tartaric acid, citric acid, lactic acid, stearic acid, benzoic acid, methanesulfonic acid, ethanesulfonic acid, and p-toluenesulfonic acid.

Preferable examples of salts of an acidic amino acid may include salts of aspartic acid and glutamic acid. Preferable examples of salts of a basic amino acid may include salts of arginine, lysine, and ornithine.

The term "antifungal agent" used in this Specification refers to an agent for preventing and/or treating fungal infections.

The compounds of the present invention, or salts or hydrates thereof, can be formulated by conventional methods into tablets, powders, fine granules, granules, coated tablets, capsules, syrups, lozenges, inhalants, suppositories, injections, ointments, eye ointments, tapes, eye drops, nose drops, ear drops, plasters, lotions, and so forth.

Any excipients, binders, lubricants, colorants, flavorings, and, as necessary, stabilizers, emulsifiers, absorbefacients, surfactants, pH regulators, preservatives, antioxidants, and so forth that are commonly used in formulation can be used, and components commonly used as ingredients of pharmaceutical preparations can be blended and formulated by standard methods. For example, an oral preparation can be produced by combining a compound of the present invention or a pharmaceutically acceptable salt thereof with an excipient and, if required, a binder, a disintegrant, a lubricant, a colorant, a flavoring, or the like, and then formulating the mixture into a powder, fine granules, granules, tablets, coated tablets, capsules, or the like by a standard method.

Examples of these components may include animal and vegetable oils such as soy bean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerol fatty acid esters, polyoxyethylene sorbitan fatty acid esters, polyoxyethylene hydrogenated castor oil, and polyoxyethylene polyoxypropylene block copolymers; water-soluble polymers such as hydroxyethyl cellulose, polyacrylic acid, carboxyvinyl polymer, polyethylene glycol, polyvinylpyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powders such as anhydrous silicic acid, magnesium aluminum silicate, and aluminum silicate; and pure water.

Examples of excipients may include lactose, corn starch, white sugar, glucose, mannitol, sorbitol, crystalline cellulose, and silicon dioxide. Examples of binders may include polyvinyl alcohol, polyvinyl ether, methyl cellulose, ethyl cellulose, gum Arabic, tragacanth, gelatin, shellac, hydroxypropyl methyl cellulose, hydroxypropyl cellulose, polyvinylpyrrolidone, polypropylene glycol-polyoxyethylene block copolymer, and meglumine. Examples of disintegrants may include starch, agar, gelatin powder, crystalline cellulose, calcium carbonate, sodium hydrogencarbonate, calcium citrate, dextrin, pectin, and calcium carboxymethyl cellulose. Examples of lubricants may include magnesium stearate, talc, polyethylene glycol, silica, and hydrogenated vegetable oils. Examples of colorants may include those that are pharmaceutically acceptable. Examples of flavorings may include cocoa powder, peppermint camphor, aromatic powders, peppermint oil, Borneo camphor, and cinnamon powder. Naturally, tablets and granules of these may be coated with sugar or, if necessary, other appropriate coatings can be given.

In manufacturing a liquid formulation such as a syrup or an injection, a pH regulator, a solubilizer, an isotonic agent, or the like and, if necessary, an auxiliary solubilizer, a stabilizer, or the like, are added to a compound of the present invention or a pharmaceutically acceptable salt thereof, and formulated according to a conventional method. Methods for manufacturing external preparations are not limited, and such preparations can be manufactured by any conventional method. Specifically, various raw materials normally used in pharmaceuticals, quasi drugs, cosmetics, and the like can be used as base materials for the formulation. Specific examples of base materials to be used may include animal and vegetable oils, minerals oils, ester oils, waxes, higher alcohols, fatty acids, silicone oil, surfactants, phospholipids, alcohols, polyhydric alcohols, water-soluble polymers, clay minerals, and pure water. Furthermore, pH regulators, antioxidants, chelating agents, preservatives and anti-mildew agents, colorants, fragrances, and the like can be added as needed, but the base materials for external preparations according to the present invention are not limited to those listed here. Also, components having a differentiation inducing action, blood flow improvers, antimicrobial agents, antiphlogistics, cell activators, vitamins, amino acids, humectants, keratolytic agents, or the like can be added as needed. The amounts in which the above-mentioned base materials are added are adjusted so as to achieve the set concentration in the manufacture of typical external preparations.

When the compound of the present invention or a salt thereof is administered, there are no particular restrictions on the form thereof, and the compound may be given orally or parenterally by any commonly used method. For example, the compound can be formulated and administered in the form of tablets, a powder, granules, capsules, a syrup, a lozenge, an inhalant, a suppository, an injection, an ointment, an eye ointment, a tape, eye drops, nasal drops, ear drops, a plaster, or a lotion.

The dose of the pharmaceutical according to the present invention can be suitably selected according to symptom severity, age, sex, body weight, form of administration, type of salt, specific type of disease, and so on.

The dose will vary markedly with the type of disease, symptom severity, age, sex, drug susceptibility, and other such factors, but in the case of an oral preparation, it is administered from once to several times a day in an amount of 1 to 10000 mg, and preferably 10 to 2000 mg, per day for a normal adult. An injection is usually administered in an amount of 0.1 to 10000 mg, and preferably 1 to 2000 mg, per day for a normal adult.

General Synthesis Methods

The method for manufacturing the compounds of the present invention and represented by formula I (hereinafter referred to as "compounds I") will now be discussed. The compound of the present invention can be synthesized by any ordinary organic synthesis method, but for example, among compounds I, the compounds represented by formula 1a, formula 2a, formula 3a, formula 4a, formula 5a, formula 6a, formula 7a, formula 8a, and formula 9a (hereinafter referred to as compound 1a, compound 2a, compound 3a, compound 4a, compound 5a, compound 6a, compound 7a, compound 8a, and compound 9a, respectively) can be synthesized by the methods given in the following Manufacturing Method 1, Manufacturing Method 2, Manufacturing Method 3, Manufacturing Method 4, Manufacturing Method 5, Manufacturing Method 6, Manufacturing Method 7, Manufacturing Method 8, Manufacturing Method 9, etc.

Manufacturing Method 1

Typical Method for Manufacturing Compound 1a (One of the Compounds I)

Manufacturing Method 1-1

Method for Manufacturing Compound 1a (One of the Compounds I)

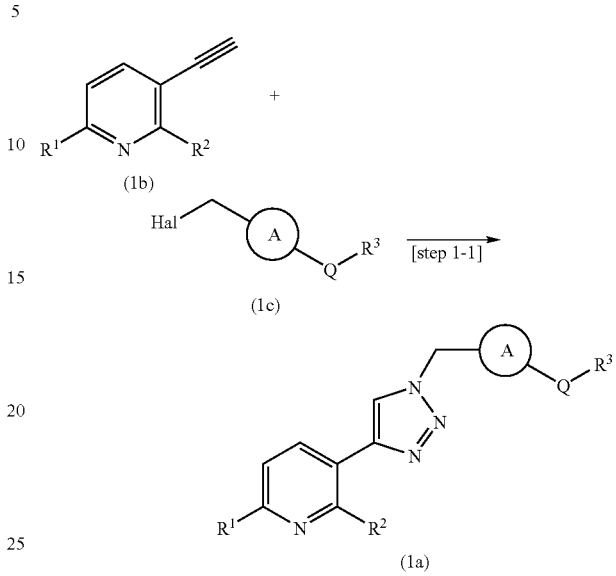

(wherein Hal represents a halogen atom, while A, $R^1$, $R^2$, Q, and $R^3$ are defined the same as above.)

Compounds 1b and 1c can be the commercially available product that is used as is, or can be manufactured by the known method from the commercially available product.

Step 1-1

In this step compound 1a is obtained by reacting compound 1b and compound 1c. Compound 1a can be obtained in a one-pot by directing microwaves at a reaction mixture of compound 1b and compound 1c in the presence of a copper catalyst and an azidation agent. The copper catalyst used in this reaction can be a copper powder or other such copper(0); copper(I) chloride, copper(I) bromide, copper(I) iodide, or other such copper(I); or copper(II) chloride, copper(II) bromide, copper(II) iodide, copper sulfate, copper trifluoromethanesulfonate, copper carbonate, copper nitrate, or other such copper(II). For the reaction to be conducted safely and good results obtained, a mixture of a copper powder or other such copper(0) and copper sulfate or other such copper (II) can be used, and copper(I) produced in the system. There are no particular restrictions on the solvent used in the reaction as long as it will dissolve the starting raw materials and reagents to a certain extent and will not impede the reaction, but examples of solvents that can be used may include tert-butyl alcohol, ethanol, methanol, and other such alcohol-based solvents, tetrahydrofuran, 1,4-dioxane, and other such ether-based solvents, N,N-dimethylformamide, N-methylpyrrolidinone, and other such amide-based solvents, dimethyl sulfoxide, water, and mixtures of these. The azidation agent used in this reaction can be sodium azide, trimethylsilyl azide, or the like. Compound 1c is used in an amount of 1 to 3 equivalents with respect to compound 1b. The copper catalyst is used in an amount of 0.01 to 1 equivalent with respect to compound 1b. The azidation agent is used in an amount of 1 to 5 equivalents with respect to compound 1c. The irradiation power is from 10 to 200 watts, the reaction temperature is from room temperature to 200° C., and the reaction duration is from 10 seconds to 30 minutes.

Manufacturing Method 1-2
Method for Manufacturing Compound 1a (One of the Compounds I)

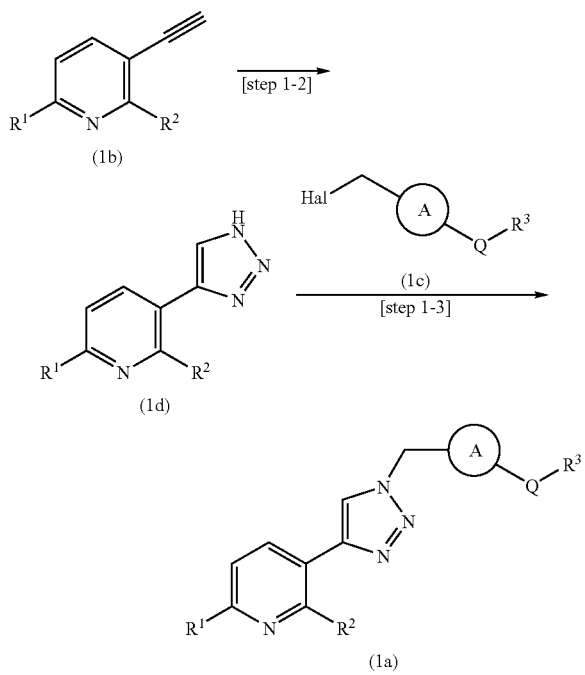

(wherein Hal represents a halogen atom, while A, $R^1$, $R^2$, Q, and $R^3$ are defined the same as above.)

Step 1-2

In this step compound 1d is obtained by reacting compound 1b and an azidation agent. Compound 1d can be obtained by reacting compound 1b and an azidation agent in the presence of a copper catalyst. The copper catalyst used in this reaction can be a copper powder or other such copper(0); copper(I) chloride, copper(I) bromide, copper(I) iodide, or other such copper(I); or copper(II) chloride, copper(II) bromide, copper(II) iodide, or other such copper(II). The azidation agent used in this reaction can be sodium azide, trimethylsilyl azide, or the like. There are no particular restrictions on the solvent used in the reaction as long as it will dissolve the starting raw materials and reagents to a certain extent and will not impede the reaction, but examples of solvents that can be used may include tert-butyl alcohol, ethanol, methanol, and other such alcohol-based solvents, tetrahydrofuran, 1,4-dioxane, and other such ether-based solvents, N,N-dimethylformamide, N-methylpyrrolidinone, and other such amide-based solvents, dimethyl sulfoxide, water, and mixtures of these. The azidation agent is used in an amount of 1 to 5 equivalents with respect to compound 1b. The copper catalyst is used in an amount of 0.01 to 0.5 equivalent with respect to compound 1b. The reaction temperature is from room temperature to the reflux temperature, and the reaction duration is from 30 minutes to 24 hours.

Step 1-3

In this step compound 1a is obtained by reacting compound 1d and compound 1c. Compound 1a can be obtained by reacting compound 1d with compound 1c in the presence of a base. The base used in this reaction can be sodium hydride, sodium hydroxide, potassium hydroxide, sodium carbonate, potassium carbonate, potassium tert-butoxide, sodium tert-butoxide, sodium methoxide, lithium methoxide, sodium acetate, potassium acetate, and triethylamine. There are no particular restrictions on the solvent used in the reaction as long as it will dissolve the starting raw materials and reagents to a certain extent and will not impede the reaction, but examples of solvents that can be used may include tetrahydrofuran, 1,4-dioxane, and other such ether-based solvents, N,N-dimethylformamide, N-methylpyrrolidinone, and other such amide-based solvents, methanol, ethanol, and other such alcohol-based solvents, acetone, acetonitrile, dimethyl sulfoxide, water, and mixtures of these. Compound 1c is used in an amount of 1 to 5 equivalents with respect to compound 1d. The base is used in an amount of 1 to 5 equivalents with respect to compound 1d. The reaction temperature is from 0° C. to the reflux temperature, and the reaction duration is from 1 minute to 24 hours.

Manufacturing Method 1-3
Method for Manufacturing Compound 1b

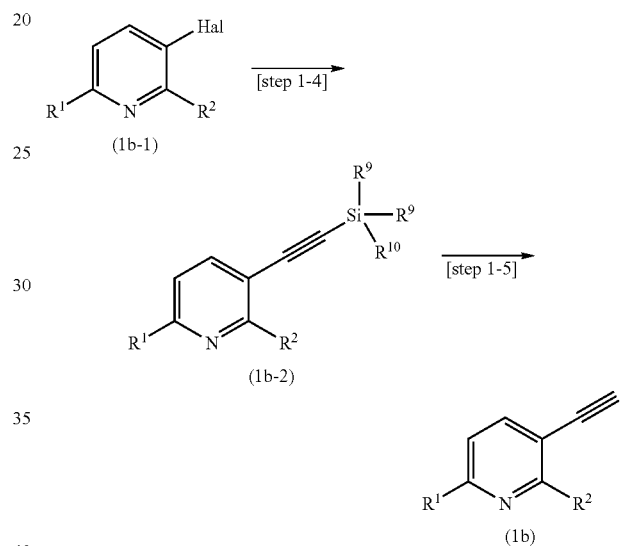

(wherein $R^1$ and $R^2$ are defined the same as above, Hal represents a halogen atom, and $R^9$ and $R^{10}$ are each independently a $C_{1-6}$ alkyl group.)

Compound 1b-1 can be the commercially available product that is used as is, or can be manufactured by the known method from the commercially available product.

Step 1-4

In this step compound 1b-2 is obtained by reacting compound 1b-1 with an ethynylsilane derivative. Compound 1b-2 can be obtained by reacting compound 1b-1 with an ethynylsilane derivative in the presence of a palladium catalyst, a base, and copper(I) iodide. To obtain better results, a phosphine ligand may be added. There are no particular restrictions on the solvent used in the reaction as long as it will dissolve the starting raw materials and reagents to a certain extent and will not impede the reaction, but examples of solvents that can be used include tetrahydrofuran, 1,4-dioxane, and other such ether-based solvents, N,N-dimethylformamide, N-methylpyrrolidinone, and other such amide-based solvents, acetonitrile, dimethyl sulfoxide, and mixtures of these. Examples of ethynylsilane derivatives that can be used may include trimethylsilylacetylene, triethylsilylacetylene, triisopropylsilylacetylene, and tert-butyldimethylsilylacetylene. Examples of palladium catalysts that can be used may include palladium(II) acetate, tetrakis(triphenylphosphine) palladium (0), dichlorobis(triphenylphosphine) palladium(II), dichlorobis(tri-o-tolylphosphine)palladium(II), bis (tri-tert-butylphosphine) palladium(0), and tris (dibenzylideneacetone) dipalladium(0). Examples of bases that can be used may include triethylamine, N,N-diisopropylethylamine, and pyridine. Examples of phosphine ligands that can be used may include triphenylphosphine, tri-o-tolylphosphine, and tri-tert-butylphosphine. The ethynylsilane derivative is used in an amount of 1 to 5 equivalents with respect to compound 1b-1. The palladium catalyst is used in an amount of 0.01 to 0.3 equivalent with respect to compound 1b-1. The base is used in an amount of 2 to 5 equivalents with respect to compound 1b-1. The phosphine ligand is used in an amount of 0.01 to 0.6 equivalent with respect to compound 1b-1. The copper(I) iodide is used in an amount of 0.001 to 0.1 equivalent with respect to compound 1b-1. The reaction temperature is from room temperature to the reflux temperature, and the reaction duration is from 30 minutes to 24 hours.

Step 1-5

In this step compound 1b is obtained by reacting compound 1b-2 with a base. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, methanol, ethanol, and other such alcohol-based solvents, N,N-dimethylformamide, N-methylpyrrolidinone, and other such amide-based solvents, acetonitrile, dimethyl sulfoxide, water, and mixtures of these. Examples of bases that can be used may include potassium carbonate, sodium hydroxide, tetrabutylammonium fluoride, potassium fluoride, and cesium fluoride. The base is used in an amount of 0.05 to 10 equivalents with respect to compound 1b-2. The reaction temperature is from 0° C. to the reflux temperature, and the reaction duration is from 5 minutes to 24 hours.

Manufacturing Method 1-4

Method for Manufacturing Compound 1b

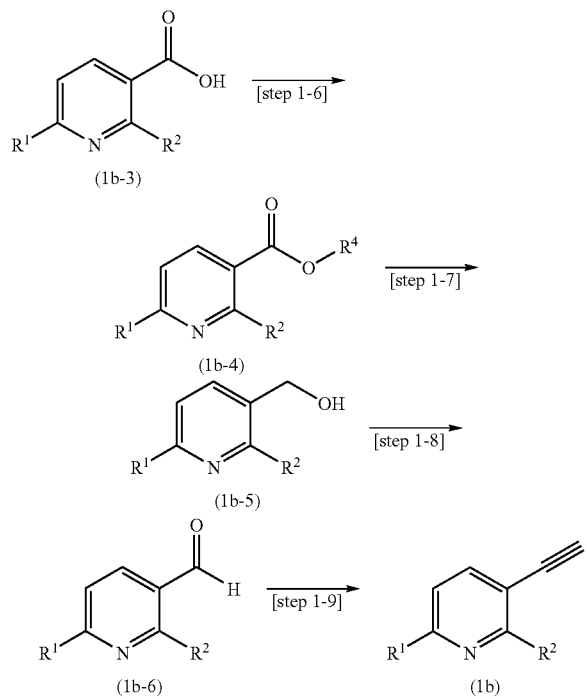

(wherein $R^1$ and $R^2$ are defined the same as above, $R^4$ represents a $C_{1-6}$ alkyl group.)

The various compounds in the step illustrated above can be the commercially available product that is used as is, or can be manufactured by the known method from the commercially available product.

Step 1-6

In this step compound 1b-4 is obtained by esterifying compound 1b-3 in the presence of an acid. The solvent used in this reaction is preferably methanol, ethanol, or another such alcohol-based solvent. Sulfuric acid, hydrochloric acid, hydrobromic acid, or the like can be used as the acid. The reaction temperature is from room temperature to the reflux temperature, and the reaction duration is from 1 hour to 72 hours.

Also, compounds 1b-4 can be obtained from compounds 1b-3 by the following Alternative Methods 1, 2, and 3.

Alternative Method 1:

Compound 1b-3 can be converted into a methyl ester by using diazomethane or trimethylsilyldiazomethane. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, benzene, toluene, and other such aromatic hydrocarbon-based solvents, methanol, ethanol, and other such alcohol-based solvents, methylene chloride, hexane, and mixtures of these. The diazomethane or trimethylsilyldiazomethane is used in an amount of 1 to 2 equivalents with respect to compound 1b-3. The reaction temperature is from 0° C. to room temperature, and the reaction duration is from 10 minutes to 24 hours.

Alternative Method 2:

Compound 1b-3 can be converted into compound 1b-4 by using an alkylation agent in the presence of a base. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, methanol, ethanol, and other such alcohol-based solvents, water, acetone, acetonitrile, dimethyl sulfoxide, and mixtures of these. Tetrabutyl ammonium bromide or another such phase transfer catalyst can also be added to this reaction. Examples of bases that can be used in this reaction may include potassium hydroxide, sodium hydroxide, lithium hydroxide, potassium carbonate, cesium carbonate, and cesium fluoride. Examples of alkylation agents that can be used may include methane iodide, ethane iodide, and dimethylsulfuric acid. The base is used in an amount of 1 to 1.5 equivalents with respect to compound 1b-3. The alkylation agent is used in an amount of 1 to 2 equivalents with respect to compound 1b-3. The reaction temperature is from 0° C. to the reflux temperature, and the reaction duration is from 1 to 72 hours.

Alternative Method 3:

Compound 1b-3 can be made into an acid chloride using a halogenation agent, and then converted into compound 1b-4 by adding an alcohol. There are no particular restrictions on the solvent used in the reaction as long as it will dissolve the starting raw materials to a certain extent and will not impede the reaction, but examples of solvents that can be used may include benzene, toluene, and other such aromatic hydrocarbon-based solvents, N,N-dimethylformamide, N-methylpyrrolidinone, and other such amide-based solvents, acetonitrile, methylene chloride, 1,2-dichloroethane, and mixtures of these. The halogenation agent can also be used as a solvent. A catalytic amount of benzyl triethyl ammonium chloride or another such phase transfer catalyst, or pyridine, can also be added to this reaction. Thionyl chloride, phosphorous pentachloride, or the like can be used as the halogenation agent. Methanol, ethanol, or the like can be used as the alcohol. The halogenation agent is used in an amount of 1 to 20 equivalents with respect to compound 1b-3. The alcohol is used in an amount of 1 to 20 equivalents with respect to compound 1b-3. The reaction temperature in converting to the acid chloride is from 0° C. to the reflux temperature, and the reaction duration is from 10 minutes to 48 hours. The reaction temperature in reacting the alcohol is from 0° C. to the reflux temperature, and the reaction duration is from 10 minutes to 48 hours. An alcohol can also be used as a solvent in this reaction. In this case, compound 1b-4 can be obtained by adding the halogenation agent to a mixture of a solvent and compound 1b-3. The reaction temperature is from 0° C. to room temperature, and the reaction duration is from 10 minutes to 24 hours.

Step 1-7

In this step compound 1b-4 is reduced to obtain compound 1b-5. There are no particular restrictions on the solvent used in the reaction as long as it will dissolve the starting raw materials to a certain extent and will not impede the reaction, but the use of tetrahydrofuran is preferable. Examples of reducing agents that can be used in this reaction may include lithium aluminum hydride, lithium aluminum hydride-aluminum chloride (aluminum chloride in the amount of 1 to 1.5 equivalents based on the lithium aluminum hydride), lithium borohydride and sodium borohydride. The reducing agent is used in an amount of 0.5 to 4 equivalents based on compound 1b-4. The reaction temperature is from 0° C. to the reflux temperature, and the reaction duration is from 10 minutes to 48 hours.

Step 1-8

In this step compound 1b-6 is obtained by oxidizing compound 1b-5. There are no particular restrictions on the solvent used in this reaction as long as it will dissolve the starting materials to a certain extent and will not impede the reaction, but examples of solvents that can be used in this reaction may include tetrahydrofuran, diethyl ether, and other such ether-based solvents, benzene, toluene, and other such aromatic hydrocarbon-based solvents, methanol, ethanol, and other such alcohol-based solvents, methylene chloride, acetone, hexane, and mixtures of these. Examples of the oxidant used in this reaction may include manganese dioxide, pyridinium chlorochromate, pyridinium dichromate, dimethyl sulfoxide-activator, tetrapropylammonium perruthenate, dichlorotris(triphenylphosphine)ruthenium(II), and 1,1,1-tris(acetyloxy)-1,1-dihydro-1,2-benziodoxol-3-(1H)-one (Dess-Martin Periodinane). The oxidant is used in an amount of from the catalytic amount to 10 equivalents with respect to compound 1b-5. When oxidizing with dimethyl sulfoxide-activator, examples of the activator include acid anhydrides such as acetic anhydride and trifluoroacetic anhydride; acid chlorides such as oxalyl chloride and thionyl chloride; chlorine; and N-chlorosuccinimide. The dimethyl sulfoxide is used in an amount of 1 to 20 equivalents with respect to the activator. When using tetrapropyl ammonium perruthenate or dichlorotris(triphenylphosphine)ruthenium(II) in a catalytic amount, an oxidant such as N-methylmorpholine-N-oxide or bis(trimethylsilyl)peroxide can be used at the same time. The reaction temperature is from −78° C. to the reflux temperature, and the reaction duration is from 10 minutes to 72 hours.

Step 1-9

In this step compound 1b is obtained from compound 1b-6 in the presence of a base and using a diazo compound. Examples of the diazo compound used in this reaction may include trimethylsilyl diazomethane, (1-diazo-2-oxopropyl)-phosphoric acid dimethyl ester, and diazomethyl phosphoric acid dimethyl ester. There are no particular restrictions on the solvent used in this reaction as long as it will dissolve the starting materials to a certain extent and will not impede the reaction, but examples of the solvent used in this reaction may include tetrahydrofuran, diethyl ether, and other such ether-based solvents, benzene, toluene, and other such aromatic hydrocarbon-based solvents, methanol, ethanol, and other such alcohol-based solvents, methylene chloride, hexane, and mixtures of these. When using trimethylsilyl diazomethane as the diazo compound, n-butyl lithium or lithium diisopropylamide can be used as the base. When using a phosphoric acid ester derivative such as (1-diazo-2-oxopropyl)-phosphoric acid dimethyl ester or diazomethyl phosphoric acid dimethyl ester as the diazo compound, potassium carbonate, potassium tert-butoxide, or the like can be used as the base. The diazo compound is used in an amount of 1 to 1.5 equivalents with respect to compound 1b-6. The base is used in an amount of 1 to 2 equivalents with respect to compound 1b-6. The reaction temperature is from −78° C. to room temperature, and the reaction duration is from 10 minutes to 24 hours.

Compound 1b can also be obtained from compound 1b-6 by the following Alternative Method 1 or 2.

Alternative Method 1:

Compound 1b-6 can be converted into a dihaloalkene in the presence of a base, and then reacted with a base to obtain compound 1b.

Dihaloalkene synthesis: There are no particular restrictions on the solvent used in this reaction as long as it will dissolve the starting materials to a certain extent and will not impede the reaction, but examples of solvents that can be used in this synthesis may include tetrahydrofuran, diethyl ether, and other such ether-based solvents, benzene, toluene, and other such aromatic hydrocarbon-based solvents, hexane, and mixtures of these. Examples of the reagent for converting compound 1b-6 into a dihaloalkene may include (dichloromethyl)-phosphoric acid dimethyl ester and dibromomethyl triphenyl phosphonium bromide (Tetrahedron Letters, Vol. 40, No. 49, 8575-8578). Examples of bases that can be used in this reaction may include lithium diisopropylamide and potassium tert-butoxide. The reagent for converting into a dihaloalkene is used in an amount of 1 to 1.5 equivalents with respect to compound 1b-6. The base is used in an amount of 1 to 2 equivalents with respect to compound 1b-6. The reaction temperature is from −78° C. to room temperature, and the reaction duration is from 10 minutes to 24 hours.

The following alternative method using carbon tetrabromide can be applied as another method for synthesizing a dihaloalkene. Compound 1b-6 is converted into a dihaloalkene by using carbon tetrabromide and triphenylphosphine, and then a base is used to obtain compound 1b. Zinc can also be added to this reaction. There are no particular restrictions on the solvent used in this reaction as long as it will dissolve the starting materials to a certain extent and will not impede the reaction, but the use of tetrahydrofuran or methylene chloride is preferable. The carbon tetrabromide can be used in an amount of 1 to 2 equivalents with respect to compound 1b-6. The triphenylphosphine can be used in an amount of 2 to 4 equivalents with respect to compound 1b-6. The zinc can be used in an amount of 1 equivalent with respect to the carbon tetrabromide. The reaction temperature is from 0° C. to room temperature, and the reaction duration is from 10 minutes to 12 hours.

Synthesis of compound 1b from a dihaloalkene: There are no particular restrictions on the solvent used in this reaction as long as it will dissolve the starting materials to a certain extent and will not impede the reaction, but examples of solvents that can be used may include tetrahydrofuran, diethyl ether, and other such ether-based solvents, benzene, toluene, and other such aromatic hydrocarbon-based solvents, hexane, and mixtures of these. Examples of bases that can be used in this reaction may include n-butyl lithium, tert-butyl lithium, and potassium tert-butoxide. The base is used in an amount of 2 to 3 equivalents with respect to the dihaloalkene. The reaction temperature is from −78° C. to room temperature, and the reaction duration is from 10 minutes to 24 hours.

Manufacturing Method 1-5

Method for Manufacturing Compound 1b-8 (Compound 1b-3)

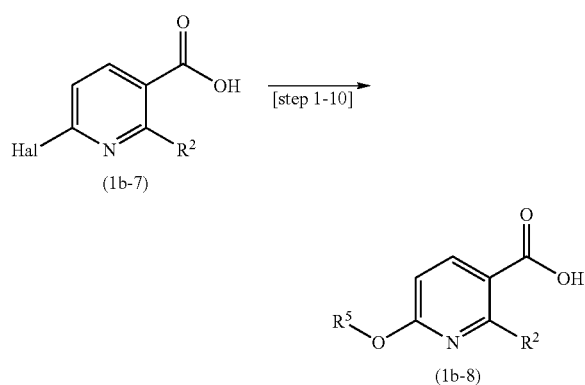

(wherein Hal and $R^2$ are defined the same as above, and $R^8$ represents a $C_{1-6}$ alkyl group.)

Compound 1b-7 can be the commercially available product that is used as is, or can be by the known method from the commercially available product.

Step 1-10

In this step compound 1b-8 is obtained by reacting compound 1b-7 with an alcohol in the presence of a base. There are no particular restrictions on the solvent used in this reaction as long as it will dissolve the starting materials to a certain extent and will not impede the reaction, but examples of the solvents in this step may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, methanol, ethanol, and other such alcohol-based solvents, dimethyl sulfoxide, and mixtures of these. Examples of bases that can be used may include sodium hydride, potassium tert-butoxide, and potassium hexamethyldisilazide. A copper catalyst can also be added to this reaction. Examples of copper catalysts that can be used may include copper, copper(I) iodide, copper(I) bromide, and copper(I) chloride. The base can be used in an amount of 1 to 20 equivalents with respect to compound 1b-7. The alcohol can be used in an amount of 1 to 20 equivalents with respect to compound 1b-7. The copper catalyst can be used in an amount of 0.01 to 0.3 equivalent with respect to compound 1b-7. The reaction temperature is from 0° C. to the reflux temperature, and the reaction duration is from 30 minutes to 48 hours.

Manufacturing Method 1-6

Method for Manufacturing Compound 1b-10 (Compound 1b-4)

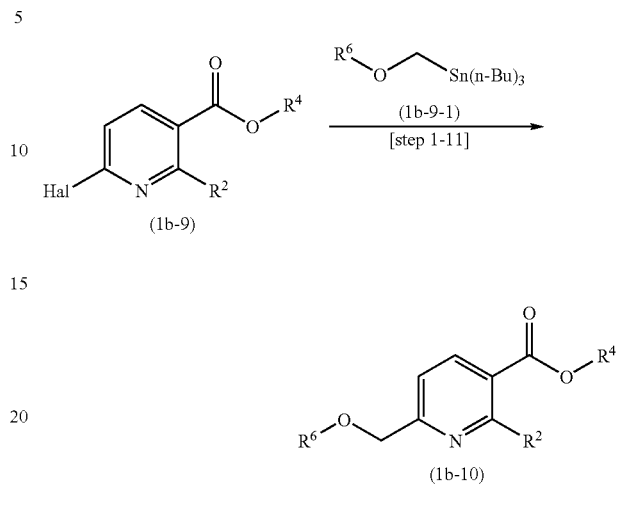

(wherein Hal, $R^2$, and $R^4$ are defined the same as above, and $R^6$ represents a $C_{1-6}$ alkyl group.)

Compound 1b-9 can be the commercially available product that is used as is, or can be manufactured by the known method from the commercially available product. Compound 1b-9-1 can be the commercially available product that is used as is, or can be manufactured by the known method from the commercially available product (such as in WO2005/033079 A1, pp. 82 to 84).

Step 1-11

In this step compound 1b-10 is obtained by reacting compound 1b-9 with compound 1b-9-1 in the presence of a palladium catalyst. A phosphine ligand can also be added to obtain better results. There are no particular restrictions on the solvent used in this reaction as long as it will dissolve the starting materials to a certain extent and will not impede the reaction, but examples of solvents that can be used may include 1,4-dioxane, tetrahydrofuran, and other such ether-based solvents, toluene, xylene, and other such aromatic hydrocarbon-based solvents, N,N-dimethylformamide, N-methylpyrrolidinone, and other such amide-based solvents, dimethyl sulfoxide, and mixtures of these. Examples of palladium catalysts that can be used may include palladium (II) acetate, tris(dibenzylideneacetone)dipalladium(0), dichlorobis(triphenylphosphine)palladium (II), dichlorobis (tri-o-tolylphosphine)palladium(II), bis(tri-tert-butylphosphine)palladium(0), tetrakis(triphenylphosphine)palladium (0), and 1,1'-bis(diphenylphosphinoferrocene)dichloropalladium(II). Examples of phosphine ligands that can be used may include triphenylphosphine, tri-o-tolylphosphine, tri-tert-butylphosphine, and diphenylphosphinoferrocene. Compound 1b-9-1 is used in an amount of 1 to 3 equivalents with respect to compound 1b-9. The palladium catalyst is used in an amount of 0.01 to 0.3 equivalent with respect to compound 1b-9. The phosphine ligand is used in an amount of 0.01 to 1.2 equivalents with respect to compound 1b-9. The reaction temperature is from room temperature to the reflux temperature, and the reaction duration is from 10 minutes to 24 hours.

Manufacturing Method 1-7
Method for Manufacturing Compound 1c-3

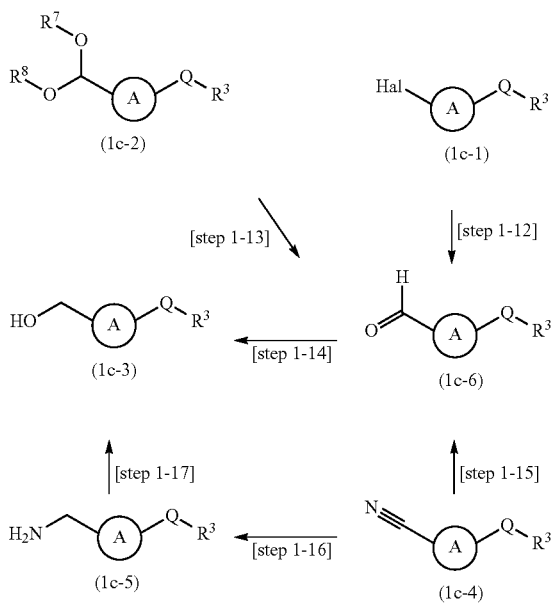

(wherein the ring A, $R^3$, Q, and Hal are defined the same as above, $R^7$ and $R^8$ independently represent a $C_{1-6}$ alkyl group or a crosslinked —$(CH_2)_n$—, and n is 2 or 3.)

Each compound in the above diagram can be the commercially available product that is used as is, or can be manufactured by the known method from the commercially available product. Also, these compounds can be manufactured by the methods described in the manufacturing examples in the working examples, and by the methods described in Manufacturing Method 1-8, Manufacturing Method 1-9, Manufacturing Method 1-10, Manufacturing Method 1-12, Manufacturing Method 1-13, Manufacturing Method 1-14, Manufacturing Method 1-15, Manufacturing Method 1-16, Manufacturing Method 1-17, Manufacturing Method 2-4, Manufacturing Method 2-5, Manufacturing Method 2-6, Manufacturing Method 2-7, Manufacturing Method 2-8, etc.

Step 1-12

In this step compound 1c-6 is obtained by substituting a metal atom for the halogen atom in compound 1c-1 to obtain an organometallic compound, and then subjecting this to the action of a formylation reagent. There are no particular restrictions on the solvent used in this reaction as long as it will dissolve the starting materials to a certain extent and will not impede the reaction, but an ether-based solvent such as tetrahydrofuran or diethyl ether is preferable. Examples of the organometallic compound may include organolithium compounds obtained using a base such as n-butyl lithium, s-butyl lithium, tert-butyl lithium, or lithium diisopropylamide, and Grignard reagents obtained using a base such as metallic magnesium, ethyl magnesium bromide, or isopropyl magnesium chloride. A catalytic amount of iodine, dibromoethane, or the like may be added in using metallic magnesium to prepare the Grignard reagents. The temperature at which the organolithium compound is prepared is from −78° C. to room temperature, and preferably from −78° C. to −40° C. The base is used in an amount of 1 to 1.5 equivalents with respect to compound 1c-1, and the reaction duration is from 30 minutes to 24 hours. The temperature at which the Grignard reagents are prepared using metal magnesium is from room temperature to the reflux temperature of the solvent. The metallic magnesium is used in an amount of 1 to 2 equivalents with respect to compound 1c-1, and the reaction duration is from 30 minutes to 12 hours. The temperature for preparing the Grignard reagents using ethyl magnesium bromide or isopropyl magnesium bromide is from −60° C. to the reflux temperature, ethyl magnesium bromide or isopropyl magnesium chloride is used in an amount of 1 to 1.6 equivalents with respect to compound 1c-1, and the reaction duration is from 5 minutes to 12 hours. Examples of formylation reagents that can be used may include dimethylformamide, N-formylpiperidine, N-formylmorpholine, and N-methylformanilide. The formylation reagent may be used in an amount of 1 to 20 equivalents, and preferably 1 to 2 equivalents, with respect to the organometallic compound. The temperature at which the organometallic compound and formylation reagent are reacted is from −78° C. to room temperature in the case of the organolithium compounds, with a reaction time of from 5 minutes to 6 hours, while in the case of the Grignard reagents the reaction temperature is from 0° C. to the reflux temperature of the solvent, with a reaction time of from 5 minutes to 24 hours.

Step 1-13

In this step compound 1c-6 is obtained by allowing an acid to act on the acetal of compound 1c-2 so as to remove the protective group. There are no particular restrictions on the solvent used in this reaction as long as it will dissolve the starting materials to a certain extent and will not impede the reaction, but examples of solvents that can be used may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, methanol, ethanol, and other such alcohol-based solvents, dimethyl sulfoxide, and mixtures of these. Examples of acids that can be used may include inorganic acids such as hydrochloric acid, sulfuric acid, and hydrobromic acid, and organic acids such as citric acid, trifluoroacetic acid, and p-toluenesulfonic acid. The reaction temperature is from 0° C. to the reflux temperature of the solvent, and the reaction duration is from 5 minutes to 24 hours.

Step 1-14

In this step compound 1c-3 is obtained by the reduction of compound 1c-6. Compound 1c-3 can be manufactured by the method as in Step 1-7.

Step 1-15

In this step compound 1c-6 is obtained by the reduction of compound 1c-4. Compound 1c-6 can be obtained by a reduction reaction using a reducing agent such as diisobutylaluminum hydride, sodium triethoxyaluminum hydride, or lithium triethoxyaluminum hydride. There are no particular restrictions on the solvent used in the reaction as long as it will dissolve the starting raw materials to a certain extent and will not impede the reaction, but examples of solvents that can be used may include toluene and other such aromatic hydrocarbon-based solvents, and tetrahydrofuran and other such ether-based solvents. The reducing agent is used in an amount of 1 to 2 equivalents with respect to compound 1c-4. The reaction temperature is from −78° C. to room temperature, and the reaction duration is from 10 minutes to 24 hours.

Step 1-16

In this step compound 1c-5 is obtained by the reduction of compound 1c-4. Compound 1c-5 can be obtained by a reduction reaction using a reducing agent such as lithium aluminum hydride or diisobutylaluminum hydride. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, and toluene and other such aromatic hydrocarbon-based solvents. The reducing agent is used in an amount of 1 to 10 equivalents with respect to compound 1c-4. The reaction temperature is from room temperature to 80° C., and the reaction duration is from 10 minutes to 24 hours.

Compound 1c-5 can also be obtained from compound 1c-4 by the following Alternative Method 1.

Alternative Method 1:

Compound 1c-5 can be obtained either by the catalytic hydrogenation of compound 1c-4 using a catalyst such as Raney nickel or palladium-carbon under a hydrogen atmosphere. There are no particular restrictions on the solvent used in the reaction as long as it will dissolve the starting raw materials to a certain extent and will not impede the reaction, but examples of solvents that can be used may include methanol, ethanol, propanol, and other such alcohol-based solvents. The reaction pressure is from 1 to 4 atmospheres. The catalyst is used in an amount ranging from a catalytic amount to an excess amount.

Step 1-17

In this step compound 1c-3 is obtained by converting the amino groups of compound 1c-5 into acetoxy groups under the action of sodium nitrite and acetic acid, and then using a base to perform hydrolysis.

Acetoxylation reaction: There are no particular restrictions on the solvent used in the reaction as long as it will dissolve the starting raw materials to a certain extent and will not impede the reaction, but favorable examples thereof may include a mixed solvent of acetic acid and water. More preferably, the ratio of acetic acid to water is from 1:5 to 5:1. Sodium nitrite is used in an amount of 1 to 20 equivalents with respect to compound 1c-5. The reaction temperature is from 0° C. to room temperature, and the reaction duration is from 1 minute to 12 hours.

Hydrolysis reaction: There are no particular restrictions on the solvent used in this reaction as long as it will dissolve the starting materials to a certain extent and will not impede the reaction, but examples of solvents that can be used may include methanol, ethanol, and other such alcohol-based solvents, tetrahydrofuran and other such ether-based solvents, N,N-dimethylformamide, N-methylpyrrolidinone, and other such amide-based solvents, water, dimethyl sulfoxide, and mixtures of these. Examples of bases that can be used may include sodium hydroxide, potassium hydroxide, and potassium carbonate. The reaction temperature is from 0° C. to 60° C., and preferably from 20° C. to 40° C., and the reaction duration is from 5 minutes to 12 hours.

Compound 1c-3 can also be obtained from compound 1c-5 by the method described as Alternative Method 1 below.

Alternative Method 1: Compound 1c-3 can be obtained by heating compound 1c-5 under strongly basic conditions. Diethylene glycol is preferable as the solvent, and potassium hydroxide is preferable as the base. The potassium hydroxide is used in an amount of 5 to 30 equivalents with respect to compound 1c-5, the reaction temperature is from 150° C. to 230° C., and the reaction duration is from 1 hour to 12 hours. During the reaction, the inside of the reaction vessel is preferably replaced with an inert gas.

Manufacturing Method 1-8

Method for Manufacturing Compound 1c-9 (Compound 1c-1)

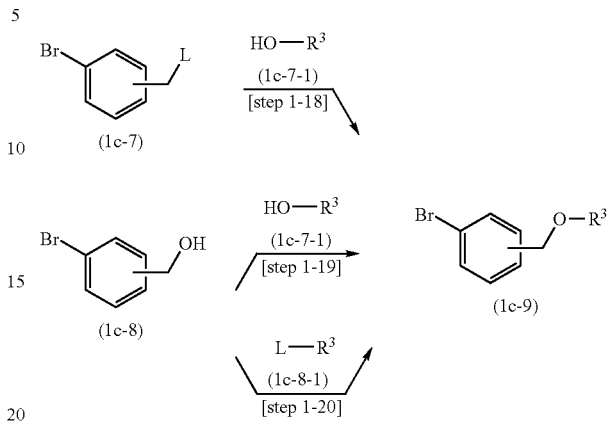

(wherein $R^3$ is defined the same as above, and L represents a leaving group such as a halogen atom, a p-toluenesulfonyl group, or a trifluoromethanesulfonyl group.)

Compound 1c-7, compound 1c-8, compound 1c-7-1, and compound 1c-8-1 can be the commercially available product that is used as is, or can be manufactured by the known method from the commercially available product.

Step 1-18

In this step compound 1c-9 is obtained by reacting compound 1c-7 and 1c-7-1 in the presence of a base. There are no particular restrictions on the solvent used in this reaction as long as it will dissolve the starting materials to a certain extent and will not impede the reaction, but examples of the solvents used in this reaction may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, methanol, ethanol, and other such alcohol-based solvents, dimethyl sulfoxide, and mixtures of these. Examples of bases that can be used may include sodium hydride, potassium tert-butoxide, sodium ethoxide, sodium methoxide, N,N-diisopropylethylamine, triethylamine, potassium hydroxide, sodium hydroxide, potassium carbonate, and sodium carbonate. The base is used in an amount of 1 to 5 equivalents with respect to compound 1c-7-1. Compound 1c-7-1 is used in an amount of 1 to 20 equivalents with respect to compound 1c-7. The reaction temperature is from 0° C. to the reflux temperature, and the reaction duration is from 5 minutes to 6 hours.

Step 1-19

In this step compound 1c-9 is obtained by reacting compound 1c-8 with an organophosphorus compound, an azo reagent, and compound 1c-7-1. There are no particular restrictions on the solvent used in this reaction as long as it will dissolve the starting materials to a certain extent and will not impede the reaction, but examples of the solvents used in this reaction may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, ethyl acetate, acetonitrile, methylene chloride, and mixtures of these. Examples of organophosphorus compounds that can be used may include triphenyl phosphine and tri-n-butyl phosphine. Examples of azo compounds that can be used may include diethyl azodicarboxylate, diisopropyl azodicarboxylate, and other such ester derivatives, and 1,1'-(azodicarbonyl)dipiperidine and other such amide derivatives. Compound 1c-7-1 is used in an amount of 1 to 1.5 equivalents with respect to compound 1c-8. The organophosphorus compound is used in an amount of 1 to 3 equivalents with respect to compound 1c-8. The azo reagent is used in an amount of 1 to 3 equivalents with respect to compound 1c-8. The reaction temperature is from 0° C. to the reflux temperature, and the reaction duration is from 5 minutes to 24 hours.

Step 1-20

In this step compound 1c-9 is obtained by reacting compound 1c-8 and compound 1c-8-1 in the presence of a base. A catalytic amount of sodium iodide, potassium iodide, or tetrabutylammonium iodide can also be added to obtain better results, or copper catalysts can be added to carry out this step. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, methanol, ethanol, and other such alcohol-based solvents, dimethyl sulfoxide, and mixtures of these. Examples of bases that can be used may include sodium hydride, potassium tert-butoxide, sodium ethoxide, sodium methoxide, N,N-diisopropylethylamine, triethylamine, potassium hydroxide, sodium hydroxide, potassium carbonate, and sodium carbonate. Examples of copper catalysts that can be used may include copper(0), copper(I) iodide, copper(I) bromide, and copper(I) chloride. Compound 1c-8-1 is used in an amount of 1 to 5 equivalents with respect to compound 1c-8. The base is used in an amount of 1 to 5 equivalents with respect to compound 1c-8. The copper catalyst can be used in an amount of 0.01 to 0.3 equivalent with respect to compound 1b-8. The reaction temperature is from 0° C. to the reflux temperature, and the reaction duration is from 5 minutes to 48 hours.

Manufacturing Method 1-9
Method for Manufacturing Compound 1c-11 (Compound 1c-3)

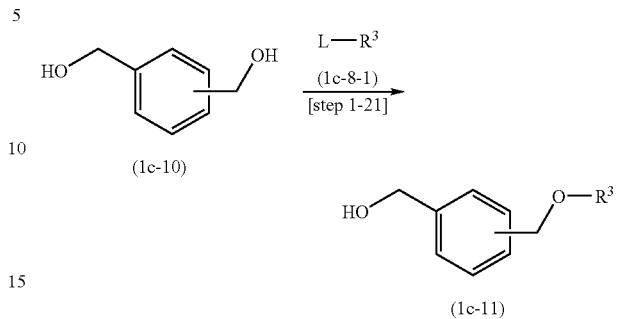

(wherein L, $R^3$ is defined the same as above.)

Compound 1c-10 can be the commercially available product. Compound 1c-8-1 can be the commercially available product or can be manufactured by the known method from the commercially available product.

Step 1-21

In this step compound 1c-11 is obtained by reacting compound 1c-10 with compound 1c-8-1. Compound 1c-8-1 is used in an amount of 0.2 to 1.0 equivalent with respect to compound 1c-10, and compound 1c-11 can be manufactured by the same method as in step 1-20.

Manufacturing Method 1-10
Method for Manufacturing Compound 1c-15 (Compound 1c-3)

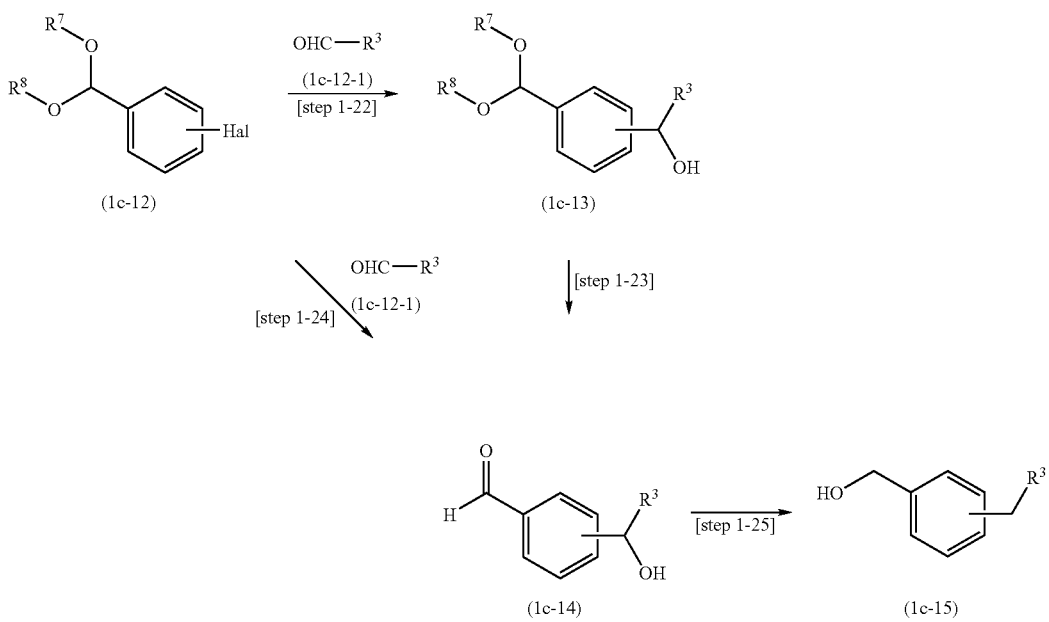

(wherein $R^3$, $R^7$, $R^8$, and Hal are defined the same as above.)

Compounds 1c-12 and 1c-12-1 can be the commercially available product that is used as is, or can be manufactured by the known method from the commercially available product.

Step 1-22

In this step compound 1c-13 is obtained by substituting a metal atom for a halogen atom of compound 1c-12 to produce an organometallic compound, and then reacting with compound 1c-12-1. There are no particular restrictions on the solvent used in this reaction as long as it will dissolve the starting materials to a certain extent and will not impede the reaction, but examples of the solvents used in this reaction may include tetrahydrofuran, diethyl ether, and other such ether-based solvents, benzene, toluene, and other such aromatic hydrocarbon-based solvents, and mixtures of these. Examples of the reagent for converting compound 1c-12 into an organometallic compound may include n-butyl lithium, s-butyl lithium, ethyl magnesium bromide, ethyl magnesium chloride, isopropyl magnesium chloride, magnesium, and zinc. The reagent for converting compound 1c-12 into an organometallic compound is used in an amount of 1 to 3 equivalents with respect to compound 1c-12. Compound 1c-12-1 is used in an amount of 1 to 2 equivalents with respect to compound 1c-12. The reaction temperature in the reaction for converting compound 1c-12 into an organometallic compound is from −78° C. to the reflux temperature, with a reaction time of from 10 minutes to 12 hours. The reaction temperature in the reaction where compound 1c-12-1 is added is from −78° C. to room temperature, with a reaction time of from 10 minutes to 6 hours.

Step 1-23

In this step compound 1c-14 is obtained by deprotecting the acetal of compound 1c-13. Compound 1c-14 can be manufactured by the same method as in Step 1-13.

Step 1-24

In this step compound 1c-14 is obtained by reacting compound 1c-12 with compound 1c-12-1. In this step, compound 1c-14 can be obtained by manufacturing compound 1c-13 by the same method as in step 1-22, then adding an acid in the reaction system or at the after-processing stage. Examples of acids that can be used in this reaction may include inorganic acids such as hydrochloric acid, sulfuric acid, and hydrobromic acid, organic acids such as citric acid, trifluoroacetic acid, and p-toluenesulfonic acid, and acidic silica gel. The reaction temperature is from 0° C. to the reflux temperature of the solvent, and the reaction duration is from 5 minutes to 24 hours.

Step 1-25

In this step compound 1c-15 is obtained by reducing compound 1c-14. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, and benzene, toluene, and other such aromatic hydrocarbon-based solvents. Lithium aluminum hydride-aluminum chloride can be used as the reducing agent. The lithium aluminum hydride is used in an amount of 2 to 6 equivalents with respect to compound 1c-14. The aluminum chloride in an amount of 2 to 9 equivalents with respect to compound 1c-14. The reaction temperature is from 0° C. to room temperature, and the reaction duration is from 10 minutes to 10 hours.

Manufacturing Method 1-11
Method for Manufacturing Compound 1c

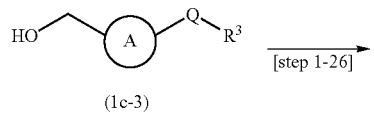

(1c-3)

[step 1-26]

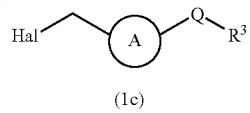

(1c)

(wherein the ring A, $R^3$, Hal, and Q are defined the same as above.)

Compound 1c-3 can be the commercially available product that is used as is, or can be manufactured by the known method from the commercially available product. Also, these compounds can be manufactured by the methods described in the manufacturing examples in the examples, or in "Manufacturing Method 1-3," etc.

Step 1-26

In this step compound 1c is obtained by substituting a hydroxyl group of compound 1c-3 for a halogen atom.

When Hal represents a chlorine atom or a bromine atom: Compound 1c can be obtained by halogenating compound 1c-3 with tetrachloromethane or tetrabromomethane in the presence of triphenylphosphine. There are no particular restrictions on the solvent used in this reaction as long as it will dissolve the starting materials to a certain extent and will not impede the reaction, but examples of the solvent may include tetrahydrofuran and other such ether-based solvents, N,N-dimethylformamide, N-methylpyrrolidinone, and other such amide-based solvents, methylene chloride, and mixtures of these. The tetrachloromethane or tetrabromomethane can also be used as the solvent. The triphenylphosphine is used in an amount of 1 to 2 equivalents with respect to compound 1c-3. The tetrachloromethane or tetrabromomethane is used in an amount of 1 equivalent to the solvent amount with respect to compound 1c-3. The reaction temperature is from 0° C. to the reflux temperature, and the reaction duration is from 10 minutes to 12 hours.

Compound 1c can also be obtained from compound 1c-3 by the methods described below as Alternative Methods 1, 2, and 3.

Alternative Method 1:

Compound 1c-3 can be converted into compound 1c under acidic conditions. There are no particular restrictions on the solvent used in this reaction as long as it will dissolve the starting materials to a certain extent and will not impede the reaction, but examples of the solvent may include diethyl ether and other such ether-based solvents, water, ethyl acetate, and mixtures of these. A phase transfer agent such as tetrabutylammonium bromide can be used in an amount of 0.01 to 2 equivalents with respect to compound 1c-3 in this reaction. Examples of acids that can be used may include hydrochloric acid and hydrobromic acid. Sulfuric acid can also be added to obtain a higher yield. The reaction temperature is from 0° C. to room temperature, and the reaction duration is from 10 minutes to 12 hours.

Alternative Method 2:

Compound 1c can be obtained by reacting compound 1c-3 with thionyl chloride. There are no particular restrictions on the solvent used in this reaction as long as it will dissolve the starting materials to a certain extent and will not impede the reaction, but examples of the solvent may include benzene, toluene, and other such aromatic hydrocarbon-based solvents, acetonitrile, chloroform, and methylene chloride, and the thionyl chloride can also be used as the solvent. Pyridine can also be added to the reaction in a catalytic amount to obtain a higher yield. The thionyl chloride is used in an amount of 1 equivalent to the solvent amount with respect to compound 1c-3. The reaction temperature is from 0° C. to the reflux temperature, and the reaction duration is from 10 minutes to 12 hours.

Alternative Method 3:

Compound 1c can be obtained by reacting compound 1c-3 with a phosphorus halide. There are no particular restrictions on the solvent used in this reaction as long as it will dissolve the starting materials to a certain extent and will not impede the reaction, but examples of the solvent may include diethyl ether and other such ether-based solvents, N,N-dimethylformamide, acetonitrile, and chloroform. Examples of phosphorus halides that can be used may include phosphorus oxychloride, phosphorus trichloride, and phosphorus tribromide. The phosphorus halide is used in an amount of 0.33 to 3 equivalents with respect to compound 1c-3. The reaction temperature is from 0° C. to the reflux temperature, and the reaction duration is from 10 minutes to 12 hours.

Manufacturing Method 1-12
Method 1 for Manufacturing Compound 1c-4

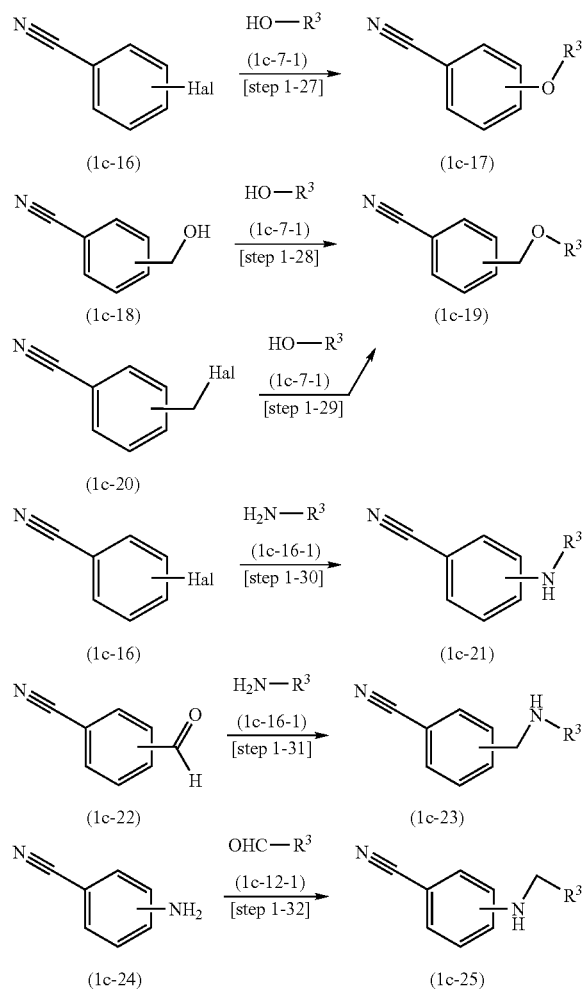

(wherein $R^3$ and Hal are defined the same as above.)

Compound 1c-16, compound 1c-18, compound 1c-20, compound 1c-22, compound 1c-24, compound 1c-7-1, compound 1c-16-1, and compound 1c-12-1 can be the commercially available product that is used as is, or can be manufactured by the known method from the commercially available product.

Step 1-27

Compound 1c-17 can be obtained by reacting compound 1c-16 with compound 1c-7-1 in the presence of a base. There are no particular restrictions on the solvent used in this reaction as long as it will dissolve the starting materials to a certain extent and will not impede the reaction, but examples of the solvent used in this reaction may include tetrahydrofuran and other such ether-based solvents, N,N-dimethylformamide, N-methylpyrrolidinone, and other such amide-based solvents, methanol, ethanol, and other such alcohol-based solvents, dimethyl sulfoxide, and mixtures of these. Examples of the base may include sodium hydride, potassium tert-butoxide, sodium ethoxide, sodium methoxide, N,N-diisopropylethylamine, triethylamine, potassium hydroxide, sodium hydroxide, potassium carbonate, and sodium carbonate. The base is used in an amount of 1 to 5 equivalents with respect to compound 1c-7-1. Compound 1c-7-1 is used in an amount of 1 equivalent to the solvent amount with respect to compound 1c-16. The reaction temperature is from room temperature to the reflux temperature, and the reaction duration is from 30 minutes to 48 hours.

Step 1-28

In this step compound 1c-19 is obtained by reacting compound 1c-18 with compound 1c-7-1. Compound 1c-19 can be manufactured by the same method as in step 1-19.

Step 1-29

In this step compound 1c-19 is obtained by reacting compound 1c-20 with compound 1c-7-1. Compound 1c-19 can be manufactured by the same method as in step 1-18.

Step 1-30

In this step compound 1c-21 is obtained by reacting compound 1c-16 with compound 1c-16-1 in the presence of a palladium catalyst. A phosphine ligand can also be added to the reaction system to obtain better results. There are no particular restrictions on the solvent used in this reaction as long as it will dissolve the starting materials to a certain extent and will not impede the reaction, but examples of the solvent in this reaction may include 1,4-dioxane, tetrahydrofuran, and other such ether-based solvents, methanol, ethanol, and other such alcohol-based solvents, toluene, xylene, and other such aromatic hydrocarbon-based solvents, N,N-dimethylformamide, N-methylpyrrolidinone, and other such amide-based solvents, and mixtures of these. Examples of palladium catalysts that can be used may include palladium(II) acetate, tris(dibenzylideneacetone)dipalladium(0), dichlorobis(triphenylphosphine)palladium(II), dichlorobis(tri-o-tolylphosphine)palladium(II), bis(tri-tert-butylphosphine)palladium (0), tetrakis(triphenylphosphine)palladium(0), and palladium(0) pentadienone. Examples of phosphine ligands that can be used may include triphenylphosphine, tri-o-tolylphosphine, tri-tert-butylphosphine, diphenylphosphinoferrocene, 2-dicyclohexylphosphinobiphenyl, 2-di-tert-butylphosphinobiphenyl, and 2,2'-bis(diphenylphosphino)-1,1'-binaphthyl (BINAP). Examples of bases that can be used may include sodium tert-butoxide, cesium carbonate, potassium carbonate, and potassium phosphate. Compound 1c-16-1 is used in an amount of 1 equivalent to an excess amount with respect to compound 1c-16. The palladium catalyst is used in an amount of 0.01 to 0.3 equivalents with respect to compound 1c-16. The phosphine ligand is used in an amount of 0.01 to 1.2 equivalents with respect to compound 1c-16. The base is used in an amount of 1 to 4 equivalents with respect to compound 1c-16. The reaction temperature is from room temperature to the reflux temperature, and the reaction duration is from 30 minutes to 72 hours.

Step 1-31

In this step compound 1c-23 is obtained by reductive amination in which compound 1c-22 is reacted with compound 1c-16-1. Acetic acid may also be added to promote the reaction. There are no particular restrictions on the solvent used in this reaction as long as it will dissolve the starting materials to a certain extent and will not impede the reaction, but examples of the solvent in this reaction may include 1,4-dioxane, tetrahydrofuran, and other such ether-based solvents, methanol, ethanol, and other such alcohol-based solvents, methylene chloride, and mixtures of these. Examples of reducing agents that can be used may include lithium aluminum hydride, sodium borohydride, sodium cyanoborohydride, sodium triacetoxyborohydride, and 2-picoline-borane. Compound 1c-16-1 is used in an amount of 1 to 2 equivalents with respect to compound 1c-22. The reducing agent is used in an amount of 1 to 2 equivalents with respect to compound 1c-22. The reaction temperature is from room temperature to the reflux temperature, and the reaction duration is from 10 minutes to 24 hours.

Step 1-32

In this step compound 1c-25 is obtained by reductive amination in which compound 1c-24 is reacted with compound 1c-12-1. Compound 1c-25 can be manufactured by the same method as in step 1-31.

Manufacturing Method 1-13

Method 2 for Manufacturing Compound 1c-4

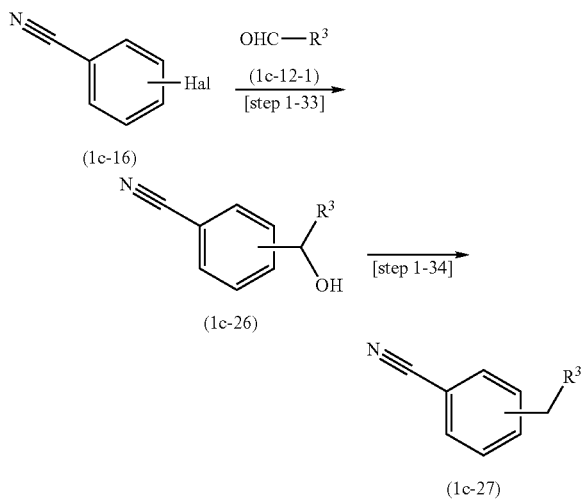

(wherein $R^3$ and Hal are defined the same as above.)

Compound 1c-16 can be the commercially available product that is used as is, or can be manufactured by the known method from the commercially available product. Compound 1c-12-1 can be the commercially available product that is used as is, or can be manufactured by the known method from the commercially available product.

Step 1-33

In this step compound 1c-26 is obtained by reacting compound 1c-16 with compound 1c-12-1. Compound 1c-26 can be manufactured by the same method as in step 1-22.

Step 1-34

In this step compound 1c-27 is obtained by reducing compound 1c-26 with iodotrimethylsilane. There are no particular restrictions on the solvent used in this reaction as long as it will dissolve the starting materials to a certain extent and will not impede the reaction, but examples of the solvent may include tetrahydrofuran and other such ether-based solvents, acetonitrile, and methylene chloride. The use of methylene chloride or acetonitrile is preferred. The iodotrimethylsilane is used in an amount of 2 to 10 equivalents with respect to compound 1c-26, the reaction temperature is from 0° C. to 60° C., and the reaction duration is from 5 minutes to 6 hours. The iodotrimethylsilane used in the reaction may be a commercially available product, or may be prepared at the time of use by reacting sodium iodide and chlorotrimethylsilane in acetonitrile at room temperature.

Manufacturing Method 1-14

Method for Manufacturing Compound 1c-28 (Compound 1c-5)

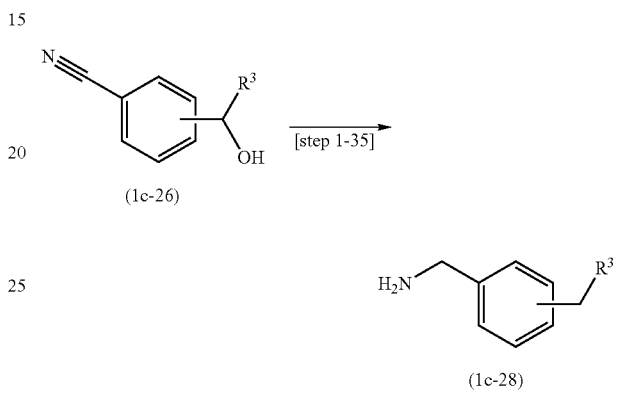

(wherein $R^3$ is defined the same as above.)

Compound 1c-26 can be the commercially available product that is used as is, or can be manufactured by the known method from the commercially available product.

Step 1-35

In this step compound 1c-28 is obtained by reducing compound 1c-26. There are no particular restrictions on the solvent used in this reaction as long as it will dissolve the starting materials to a certain extent and will not impede the reaction, but examples of the solvents used in this reaction may include tetrahydrofuran, diethyl ether, and other such ether-based solvents, and benzene, toluene, and other such aromatic hydrocarbon-based solvents. Lithium aluminum hydride-aluminum chloride can be used as the reducing agent. The lithium aluminum hydride is used in an amount of 3 to 8 equivalents with respect to compound 1c-26. The aluminum chloride is used in an amount of 3 to 10 equivalents with respect to compound 1c-26. The reaction temperature is from 0° C. to the reflux temperature, and the reaction duration is from 10 minutes to 48 hours.

Manufacturing Method 1-15

Method for Manufacturing Compound 1c-29 (Compound 1c-6)

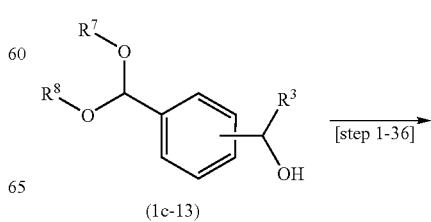

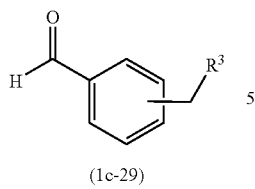

(1c-29)

(wherein $R^3$, R', and $R^8$ are defined the same as above.)

Compound 1c-13 can be the commercially available product that is used as is, or can be manufactured by the known method from the commercially available product.

Step 1-36

In this step compound 1c-29 is obtained by simultaneous reduction and acetal deprotection of compound 1c-13 using iodotrimethylsilane. There are no particular restrictions on the solvent used in this reaction as long as it will dissolve the starting materials to a certain extent and will not impede the reaction, but examples of the solvent may include tetrahydrofuran and other such ether-based solvents, acetonitrile, and methylene chloride. The use of methylene chloride or acetonitrile is preferred. The iodotrimethylsilane is used in an amount of 2 to 10 equivalents with respect to compound 1c-13. The reaction temperature is from 0° C. to 60° C., and the reaction duration is from 5 minutes to 6 hours. The iodotrimethylsilane used in the reaction may be the commercial product, or may be prepared at the time of use by reacting sodium iodide and chlorotrimethylsilane in acetonitrile at room temperature.

Manufacturing Method 1-16

Method for Manufacturing Compound 1c-34 (Compound 1c-3)

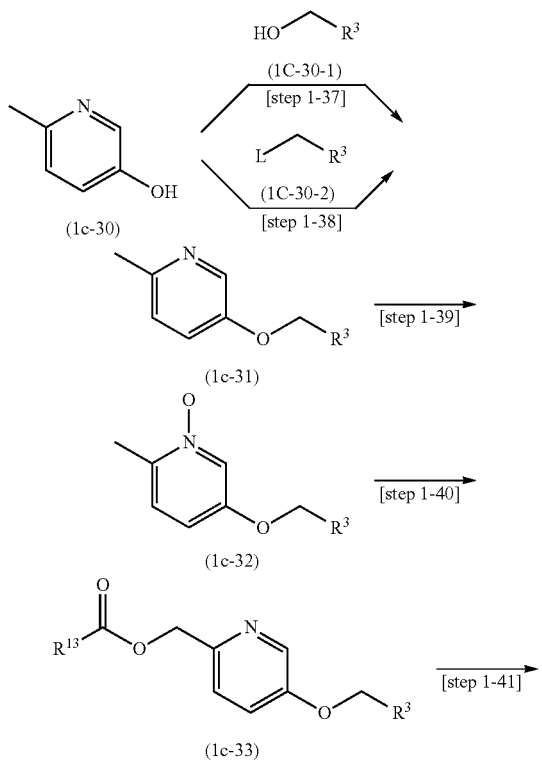

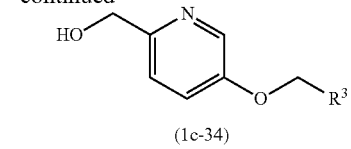

(1c-34)

(wherein $R^3$ and L are defined the same as above, and $R^{13}$ represents a $C_{1-6}$ alkyl group that may be substituted with a halogen or the like.)

Compound 1c-30, compound 1c-30-1, and compound 1c-30-2 can be the commercially available product that is used as is, or can be manufactured by the known method from the commercially available product.

Step 1-37

In this step compound 1c-31 is obtained by reacting compound 1c-30 with an organophosphorus compound, an azo reagent, and compound 1c-30-1. Compound 1c-31 can be obtained by the same method as in step 1-19.

Step 1-38

In this step compound 1c-31 is obtained by reacting compound 1c-30 with compound 1c-30-2 in the presence of a base. Compound 1c-31 can be obtained by the same method as in step 1-18.

Step 1-39

In this step compound 1c-32 is obtained by reacting compound 1c-31 with a peroxide. Examples of peroxides that can be used may include m-chloroperbenzoic acid, hydrogen peroxide, dimethyldioxirane, benzoyl peroxide, and peracetic acid. There are no particular restrictions on the solvent used in this reaction as long as it will dissolve the starting materials to a certain extent and will not impede the reaction, but examples of the solvent may include chloroform, methylene chloride, and other such halogen-based solvents, methanol, ethanol, and other such alcohol-based solvents, N,N-dimethylformamide, N-methylpyrrolidinone, and other such amide-based solvents, benzene, toluene, and other such aromatic hydrocarbon-based solvents, diethyl ether, acetone, acetonitrile, acetic acid, and water. The peroxide is used in an amount of 1 to 5 equivalents with respect to compound 1c-31. The reaction temperature is from −40° C. to the reflux temperature, and the reaction duration is from 1 minute to 48 hours.

Step 1-40

In this step compound 1c-33 is obtained by reacting compound 1c-32 with an acid anhydride. Examples of the acid anhydride used in this reaction may include acetic anhydride and trifluoroacetic acid anhydride. There are no particular restrictions on the solvent used in this reaction as long as it will dissolve the starting materials to a certain extent and will not impede the reaction, but examples of the solvent may include chloroform, methylene chloride, and other such halogen-based solvents, benzene, toluene, and other such aromatic hydrocarbon-based solvents, acetic acid, and trifluoroacetic acid. An acid anhydride can also be used as the solvent. The acid anhydride is used in an amount of from 1 equivalent to an excess amount with respect to compound 1c-32. The reaction temperature is from 0° C. to the reflux temperature, and the reaction duration is from 10 minutes to 24 hours.

Step 1-41

In this step compound 1c-34 is obtained by hydrolyzing compound 1c-33. For example, compound 1c-34 can be obtained by hydrolyzing compound 1c-33 in the presence of an acid such as hydrochloric acid or sulfuric acid, or in the presence of an alkali such as sodium hydroxide, potassium hydroxide, sodium methoxide, potassium carbonate, or sodium carbonate. There are no particular restrictions on the solvent used in this reaction as long as it will dissolve the starting materials to a certain extent and will not impede the reaction, but examples of the solvent may include 1,4-dioxane, tetrahydrofuran, and other such ether-based solvents, methanol, ethanol, and other such alcohol-based solvents, methylene chloride, chloroform, and other such halogen-based solvents, benzene, toluene, and other such aromatic hydrocarbon-based solvents, N,N-dimethylformamide, N-methylpyrrolidinone, and other such amide-based solvents, dimethyl sulfoxide, acetonitrile, water, and mixtures of these. The acid or base is used in an amount of from 1 equivalent to an excess amount with respect to compound 1c-33. The reaction temperature is from 0° C. to the reflux temperature, and the reaction duration is from 10 minutes to 24 hours.

Manufacturing Method 1-17

Method for Manufacturing Compound 1c-41 (Compound 1c-3)

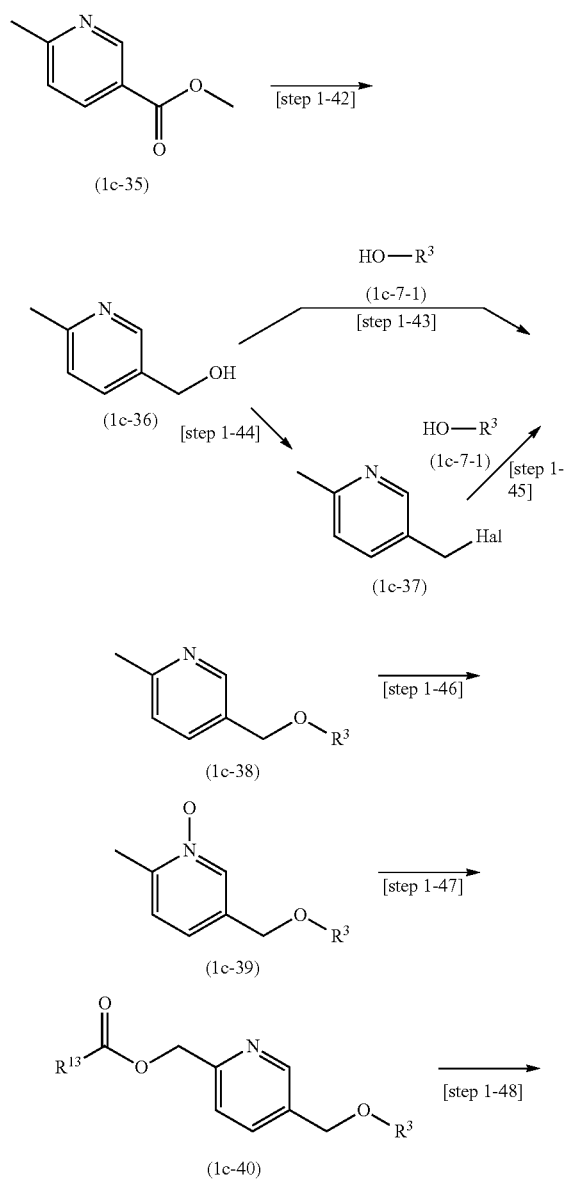

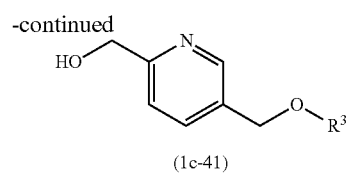

(wherein $R^3$ and Hal are defined the same as above, and $R^{13}$ represents a $C_{1-6}$ alkyl group that may be substituted with a halogen or the like.)

Compound 1c-35 and compound 1c-7-1 can be the commercially available product that is used as is, or can be manufactured by the known method from the commercially available product.

Step 1-42

In this step compound 1c-36 is obtained by reducing compound 1c-35, and can be obtained by the same method as in step 1-7.

Step 1-43

In this step compound 1c-38 is obtained by reacting compound 1c-36 with an organophosphorus compound, an azo reagent, and compound 1c-7-1. Compound 1c-38 can be manufactured by the same method as in step 1-19.

Step 1-44

In this step compound 1c-37 is obtained by converting the hydroxyl group of compound 1c-36 into a leaving group. Compound 1c-37 can be manufactured by the same method as in step 1-26.

Step 1-45

In this step compound 1c-38 is obtained by reacting compound 1c-37 with compound 1c-7-1 in the presence of a base. Compound 1c-38 can be manufactured by the same method as in step 1-18.

Step 1-46

In this step compound 1c-39 is obtained by reacting compound 1c-38 with a peroxide. Compound 1c-39 can be manufactured by the same method as in step 1-39.

Step 1-47

In this step compound 1c-40 is obtained by reacting compound 1c-39 with an acid anhydride. Compound 1c-40 can be manufactured by the same method as in step 1-40.

Step 1-48

In this step compound 1c-41 is obtained by hydrolyzing compound 1c-40. Compound 1c-41 can be manufactured by the same method as in step 1-41.

Manufacturing Method 2

Typical Method for Manufacturing Compound 2a (Compound I)

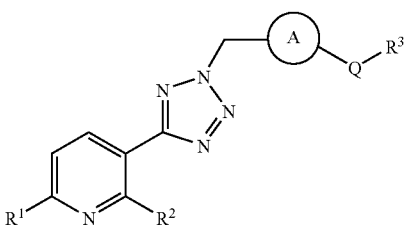

(wherein A, $R^1$, $R^2$, Q, and $R^3$ are defined the same as above.)

Manufacturing Method 2-1

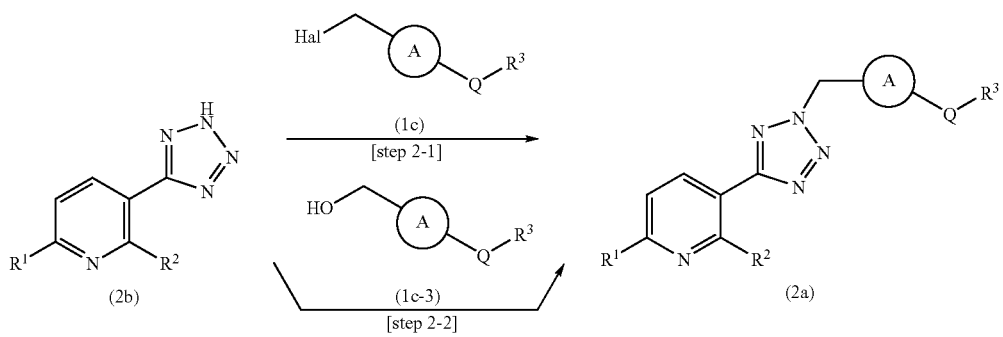

(wherein A, Hal, $R^1$, $R^2$, Q, and $R^3$ are defined the same as above.)

Compound 1c and compound 1c-3 can be the commercially available product that is used as is, or can be manufactured by the known method from the commercially available product, or can be manufactured by one of the methods described herein.

Step 2-1

In this step compound 2a is obtained by reacting compounds 2b and 1c. Examples of bases that can be used may include triethylamine, N,N-diisopropylethylamine, sodium hydrogencarbonate, potassium carbonate, sodium hydroxide, potassium hydroxide, and sodium hydride. There are no particular restrictions on the solvent used in the reaction as long as it will dissolve the starting raw materials to a certain extent and will not impede the reaction, but examples of solvents that can be used may include tetrahydrofuran, 1,4-dioxane, and other such ether-based solvents, N,N-dimethylformamide, N-methylpyrrolidinone, and other such amide-based solvents, dimethyl sulfoxide, and mixtures of these. Compound 1c and the base are used in an amount of 1 to 2 equivalents with respect to compound 2b. The reaction temperature is from room temperature to the reflux temperature, and the reaction duration is from 10 minutes to 48 hours.

Step 2-2

In this step compound 2a is obtained by allowing an azo reagent and an organophosphorus compound to act on compound 1c-3 and compound 2b. There are no particular restrictions on the solvent used in this reaction as long as it will dissolve the starting materials to a certain extent and will not impede the reaction, but examples of the solvents used in this reaction may include toluene, xylene, and other such aromatic hydrocarbon-based solvents, tetrahydrofuran, 1,4-dioxane, and other such ether-based solvents, dichloromethane, chloroform, and other such halogen-based solvents, N,N-dimethylformamide, N-methylpyrrolidinone, and other such amide-based solvents, dimethyl sulfoxide, and mixtures of these. Examples of organophosphorus compounds that can be used may include triphenyl phosphine, tri-2-furyl phosphine, and diphenyl-2-pyridyl phosphine. Examples of azo reagents that can be used include diethyl azodicarboxylate, diisopropyl azodicarboxylate, and dimethyl azodicarboxylate. Compound 1c-3, the organophosphorus compound, and the azo reagent are used in an amount of 1 to 3 equivalents with respect to compound 2b. The reaction temperature is from −20° C. to 80° C., and the reaction duration is from 5 minutes to 48 hours.

Method for Manufacturing Compound 2a (Compound I)

Manufacturing Method 2-2
Method for Manufacturing Compound 2b

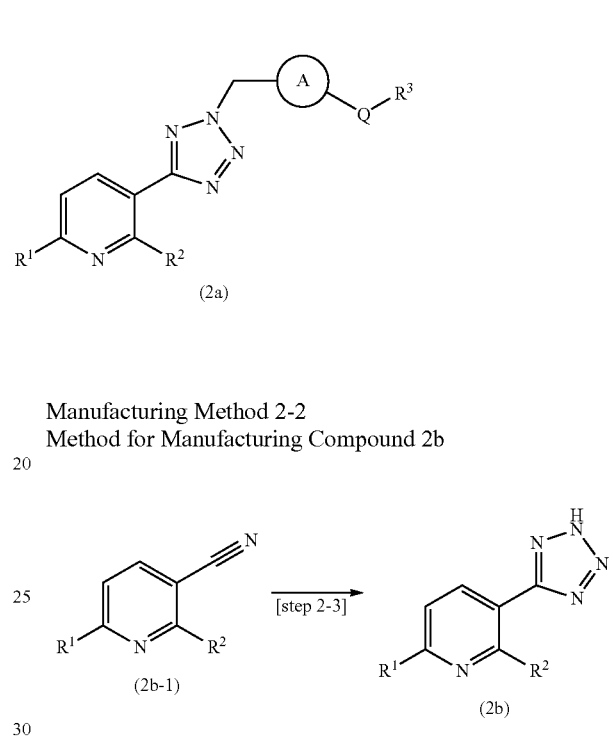

(wherein $R^1$ and $R^2$ are defined the same as above.)

Compound 2b-1 can be the commercially available product that is used as is, or can be manufactured by the known method from the commercially available product, or can be manufactured by one of the methods described herein.

Step 2-3

In this step compound 2b is obtained by reacting compound 2b-1 with sodium azide in the presence of a salt. Examples of salts that can be used in this reaction may include triethylamine hydrochloride and ammonium chloride. There are no particular restrictions on the solvent used in the reaction as long as it will dissolve the starting raw materials to a certain extent and will not impede the reaction, but examples of solvents that can be used may include N,N-dimethylformamide, N-methylpyrrolidinone, and other such amide-based solvents, dimethyl sulfoxide, and mixtures of these. The sodium azide is used in an amount of 1 to 10 equivalents with respect to compound 2b-1. The salt is used in an amount of 1 to 5 equivalents with respect to the sodium azide. The reaction temperature is from 60° C. to the reflux temperature, and the reaction duration is from 1 to 48 hours.

Compound 2b can also be obtained from compound 2b-1 by the method described below as Alternative Method 1.

Alternative Method 1: Compound 2b can be obtained by reacting compound 2b-1 with an azidation agent such as trimethyltin azide or tributyltin azide, and then subjecting this to the action of an acid and deprotecting the trialkyltin group. The azidation agent is used in an amount of 1 to 10 equivalents with respect to compound 2b-1. There are no particular restrictions on the solvent used in the reaction as long as it will dissolve the starting raw materials to a certain extent and will not impede the reaction, but examples of solvents that can be used may include toluene, xylene, and other such aromatic hydrocarbon-based solvents, 1,4-dioxane and other such ether-based solvents, N,N-dimethylformamide, N-methylpyrrolidinone, and other such amide-based solvents, dimethyl sulfoxide, and mixtures of these. The reaction temperature is from 60° C. to the reflux temperature, and the reaction duration is from 30 minutes to 48 hours. There are no particular restrictions on the acid used to deprotect the trialkyltin group, but a strong acid such as hydrochloric acid is preferable. There are no particular restrictions on the solvent used in the reaction as long as it will dissolve the starting raw materials and reagents to a certain extent and will not impede the reaction, but examples of solvents that can be used may include toluene, xylene, and other such aromatic hydrocarbon-based solvents, tetrahydrofuran, 1,4-dioxane, and other such ether-based solvents, N,N-dimethylformamide, N-methylpyrrolidinone, and other such amide-based solvents, dimethyl sulfoxide, and mixtures of these. The reaction temperature is from 0° C. to the reflux temperature, the acid is used in an amount of from 2 equivalents to an excess amount with respect to compound 1b, and the reaction duration is from 10 minutes to 24 hours.

Manufacturing Method 2-3
Method for Manufacturing Compound 2b-1

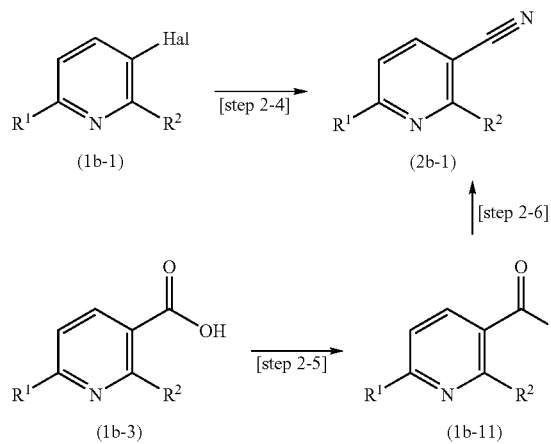

(wherein Hal represents a halogen atom, and $R^1$ and $R^2$ are defined the same as above.)

The various compounds in the step illustrated above can be the commercially available product that is used as is, or can be manufactured by the known method from the commercially available product.

Step 2-4

In this step compound 2b-1 is obtained by subjecting compound 1b-1 to cyanization with zinc cyanide in the presence of a catalyst. A phosphine ligand may also be added to obtain better results. There are no particular restrictions on the solvent used in the reaction as long as it will dissolve the starting raw materials to a certain extent and will not impede the reaction, but examples of solvents that can be used may include tetrahydrofuran, 1,4-dioxane, and other such ether-based solvents, N,N-dimethylformamide, N-methylpyrrolidinone, and other such amide-based solvents, acetonitrile, dimethyl sulfoxide, and mixtures of these. Examples of palladium catalysts that can be used may include palladium(II) acetate, tetrakis(triphenylphosphine) palladium(0), dichlorobis(triphenylphosphine) palladium(II), dichlorobis(tri-o-tolylphosphine) palladium(II), bis(tri-tert-butylphosphine) palladium(0), and tris(dibenzylideneacetone) palladium(0). Examples of phosphine ligands that can be used may include triphenylphosphine, tri-o-tolylphosphine, and tri-tert-butylphosphine. The zinc cyanide is used in an amount of 0.5 to 5 equivalents with respect to compound 1b-1. The palladium catalyst is used in an amount of 0.01 to 0.3 equivalents with respect to compound 1b-1. The phosphine ligand is used in an amount of 0.01 to 1.2 equivalents with respect to compound 1b-1. The reaction temperature is from 60° C. to the reflux temperature, and the reaction duration is from 30 minutes to 24 hours.

Step 2-5

In this step compound 1b-11 is obtained by the amidation of compound 1b-3. Compound 1b-11 can be obtained by allowing ammonium chloride and a condensation agent to act on compound 1b-3 in the presence of a base. There are no particular restrictions on the solvent used in the reaction as long as it will dissolve the starting raw materials to a certain extent and will not impede the reaction, but examples of solvents that can be used may include tetrahydrofuran, 1,4-dioxane, and other such ether-based solvents, N,N-dimethylformamide, N-methylpyrrolidinone, and other such amide-based solvents, acetonitrile, dimethyl sulfoxide, and mixtures of these. Examples of bases that can be used may include triethylamine, diisopropylethylamine, potassium carbonate, and sodium hydroxide. Examples of condensation agents that can be used may include 1-ethyl-3-(3-dimethylaminopropyl) carbodiimide hydrochloride (hereinafter referred to as WSC), and N,N-dicyclohexylcarbodiimide (hereinafter referred to as DCC). The ammonium chloride is used in an amount of 1 to 10 equivalents with respect to compound 1b-3. The base is used in an amount of 1 to 5 equivalents with respect to the ammonium chloride. The reaction temperature is from room temperature to the reflux temperature, and the reaction duration is from 1 to 72 hours.

Step 2-6

In this step compound 2b-1 is obtained by allowing a dehydration agent to act on compound 1b-11. There are no particular restrictions on the solvent used in the reaction as long as it will dissolve the starting raw materials to a certain extent and will not impede the reaction, but examples of solvents that can be used may include tetrahydrofuran, 1,4-dioxane, and other such ether-based solvents, N,N-dimethylformamide, N-methylpyrrolidinone, and other such amide-based solvents, toluene, xylene, and other such aromatic hydrocarbon-based solvents, pyridine, acetonitrile, dimethyl sulfoxide, and mixtures of these. Using a dehydration agent as the solvent is also effective. Examples of dehydration agents that can be used may include diphosphorus pentoxide, thionyl chloride, dicyclohexylcarbodiimide, and phosphorus oxychloride. The dehydration agent is used in an amount of from 1 equivalent to an excess amount with respect to compound 1b-11. The reaction temperature is from room temperature to the reflux temperature of the solvent.

Manufacturing Method 2-4
Method for Manufacturing Compound 1c-44 (Compound 1c-3)

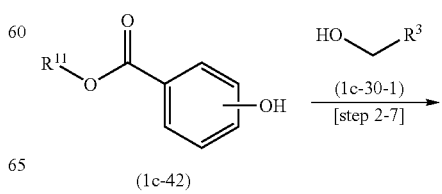

51

-continued (1c-43)

(1c-44)

(wherein R¹¹ represents a $C_{1-6}$ alkyl group, and $R^3$ is defined the same as above.)

Compound 1c-42 and compound 1c-30-1 can be the commercially available product that is used as is, or can be manufactured by the known method from the commercially available product.

Step 2-7

In this step compound 1c-43 is obtained by condensing compounds 1c-42 and 1c-30-1 in the presence of an organophosphorus compound and an azo reagent. Compound 1c-43 can be obtained by the same method as in step 2-2.

Step 2-8

In this step compound 1c-44 is obtained by reducing compound 1c-43. Compound 1c-44 can be obtained by the same method as in step 1-7.

Manufacturing Method 2-5

Method for Manufacturing Compound 1c-47 (Compound 1c-3)

(1c-45)

(1c-46)

(1c-47)

(wherein $R^3$ is defined the same as above.)

Compound 1c-45 and compound 1c-45-1 can be the commercially available product that is used as is, or can be manufactured by the known method from the commercially available product.

Step 2-9

In this step compound 1c-46 is obtained by reacting compound 1c-45 with compound 1c-45-1. There are no particular restrictions on the solvent used in the reaction as long as it will dissolve the starting raw materials and reagents to a certain extent and will not impede the reaction, but acetic acid or the like can be used, for example. Compound 1c-45-1 is used in an amount of 1 equivalent with respect to compound 1c-45.

52

The reaction temperature is from 50° C. to 110° C., and the reaction duration is from 5 minutes to 1 hour.

Step 2-10

In this step compound 1c-47 is obtained by reducing compound 1c-46. Compound 1c-47 can be obtained by the same method as in step 1-7.

Manufacturing Method 2-6

Method for Manufacturing Compound 1c-49 (Compound 1c-6)

(1c-48)

(1c-49)

(wherein E represents an oxygen atom or a sulfur atom, Ar represents a $C_{6-10}$ aryl group or a 5- or 6-membered heteroaryl group, each of which may have one or two substituents selected from among a substituent group α.)

Substituent Group α a halogen atom, a $C_{1-6}$ alkyl group, a $C_{1-6}$ alkoxy group, a $C_{3-8}$ cycloalkyl group, a $C_{2-6}$ alkenyl group, and a $C_{2-6}$ alkynyl group Compound 1c-48 can be the commercially available product that is used as is. Compound 1c-48-1 can be the commercially available product that is used as is, or can be manufactured by the known method from the commercially available product.

Step 2-11

In this step compound 1c-49 is obtained by reacting compound 1c-48 with compound 1c-48-1 in the presence of a base. There are no particular restrictions on the solvent used in the reaction as long as it will dissolve the starting raw materials to a certain extent and will not impede the reaction, but examples of solvents that can be used may include tetrahydrofuran, 1,4-dioxane, and other such ether-based solvents, N,N-dimethylformamide, N-methylpyrrolidinone, and other such amide-based solvents, acetonitrile, dimethyl sulfoxide, and mixtures of these. Examples of bases that can be used may include sodium hydride, potassium carbonate, and sodium hydroxide. Compound 1c-48-1 is used in an amount of 1 to 2 equivalents with respect to compound 1c-48. The base is used in an amount of 1 to 2 equivalents with respect to compound 1c-48. The reaction temperature is from 0° C. to the reflux temperature of the solvent, and the reaction duration is from 5 minutes to 24 hours.

Manufacturing Method 2-7
Method for Manufacturing Compound 1c-52 (Compound 1c-6)

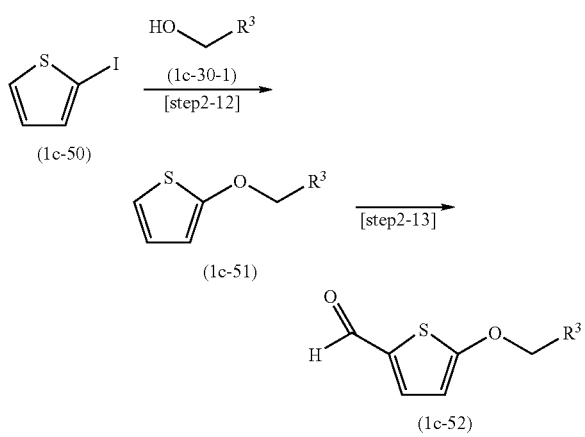

(wherein R³ is defined the same as above.)

Compound 1c-50 can be the commercially available product that is used as is.

Step 2-12

In this step compound 1c-51 is obtained by reacting compound 1c-50 with compound 1c-30-1 in the presence of 1,10-phenanthroline, a base, and a catalyst. There are no particular restrictions on the solvent used in the reaction as long as it will dissolve the starting raw materials to a certain extent and will not impede the reaction, but examples of solvents that can be used may include toluene, xylene, and other such aromatic hydrocarbon-based solvents, tetrahydrofuran, 1,4-dioxane, and other such ether-based solvents, N,N-dimethylformamide, N-methylpyrrolidinone, and other such amide-based solvents, acetonitrile, dimethyl sulfoxide, and mixtures of these. Examples of bases that can be used may include potassium carbonate, cesium carbonate, and potassium phosphate. Examples of catalysts that can be used may include copper(I) iodide, copper(I) chloride, and copper(I) bromide. The base is used in an amount of 1 to 5 equivalents with respect to compound 1c-50, the catalyst is used in an amount of 0.05 to 0.5 equivalent with respect to compound 1c-50, and the 1,10-phenanthroline is used in an amount of 0.05 to 1 equivalent with respect to compound 1c-50. Compound 1c-30-1 is used in an amount of 1 to 3 equivalents with respect to compound 1c-50. The reaction temperature is from 80° C. to the reflux temperature of the solvent, and the reaction duration is from 30 minutes to 24 hours.

Step 2-13

In this step compound 1c-52 is obtained by using a strong base to substitute a hydrogen atom of compound 1c-51 for a metal atom to produce an organometallic compound, and then subjecting this to the action of a formylation reagent. There are no particular restrictions on the solvent used in the reaction as long as it will dissolve the starting raw materials to a certain extent and will not impede the reaction, but tetrahydrofuran, diethyl ether, or another such ether-based solvent is preferable. Examples of strong bases that can be used may include n-butyl lithium, s-butyl lithium, tert-butyl lithium, and lithium diisopropylamide. The temperature at which the organometallic compound is prepared is from −78° C. to room temperature, and preferably from −78° C. to −40° C. The base is used in an amount of 1 to 1.5 equivalents with respect to compound 1c-51, and the reaction duration is from 30 minutes to 24 hours. Examples of formylation reagents that can be used may include dimethylformamide, N-formylpiperidine, N-formylmorpholine, and N-methylformanilide. The formylation reagent is used in an amount of 1 to 20 equivalents, and preferably 1 to 2 equivalents, with respect to the metal compound. The temperature at which the metal compound and the formylation reagent are reacted is from −78° C. to room temperature, and the reaction duration is from 5 minutes to 6 hours.

Manufacturing Method 3

Typical Method for Manufacturing Compound 3a (Compound I)

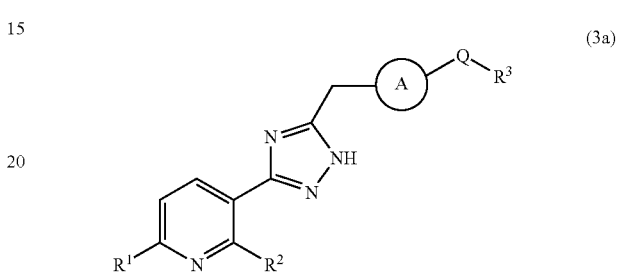

(wherein A, R¹, R², Q, and R³ are defined the same as above.)

Manufacturing Method 3-1

Method for Manufacturing Compound 3a (Compound I)

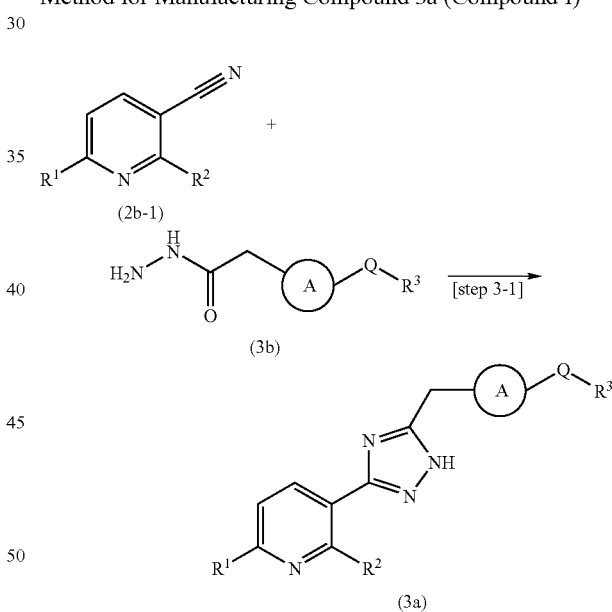

(wherein A, R¹, R², Q, and R³ are defined the same as above.)

Compound 2b-1 can be the commercially available product that is used as is, or can be manufactured by the known method from the commercially available product. Furthermore, it can be manufactured by the methods described in the manufacturing examples in the examples, and by the method described in Manufacturing Method 2-3, etc.

Compound 3b can be manufactured by the known method from the commercially available product. Furthermore, it can be manufactured by the methods described in the manufacturing examples in the examples, and by the methods described in Manufacturing Method 3-2, Manufacturing Method 3-3, etc.

Step 3-1

In this step compound 3a is obtained by reacting compound 2b-1 with compound 3b in the presence of an acid or a base, or by heating under neutral conditions. There are no particular restrictions on the solvent used in the reaction as long as it will dissolve the starting raw materials to a certain extent and will not impede the reaction, but examples of solvents that can be used may include methanol, ethanol, and other such alcohol-based solvents, tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, water, methylene chloride, chloroform, ethyl acetate, dimethyl sulfoxide, and mixtures of these. Examples of acids that can be used in this reaction may include hydrochloric acid, sulfuric acid, and examples of bases that can be used may include sodium methoxide, sodium ethoxide, etc. The acid and base are used in an amount of 0.1 to 1 equivalent with respect to compound 2b-1. Compound 3b is used in an amount of 1.0 to 1.5 equivalents with respect to compound 2b-1. The reaction temperature is from room temperature to the reflux temperature, and the reaction duration is from 1 to 60 hours.

Manufacturing Method 3-2
Method for Manufacturing Compound 3b restrictions on the solvent used in the reaction as long as it will dissolve the starting raw materials to a certain extent and will not impede the reaction, but examples of solvents that can be used may include benzene, toluene, and other such aromatic hydrocarbon-based solvents, N,N-dimethylformamide, N-methylpyrrolidinone, and other such amide-based solvents, acetonitrile, methylene chloride, 1,2-dichloroethane, and mixtures of these. The halogenation agent can also be used as the solvent. A catalytic amount of pyridine or a phase transfer catalyst such as benzyltriethylammonium chloride can also be added to this reaction. Examples of halogenation agents that can be used may include thionyl chloride and phosphorus pentachloride. The halogenation agent is used in an amount of 1 to 20 equivalents with respect to compound 3b-1. The reaction duration is from 10 minutes to 5 hours. The reaction temperature is from 0° C. to room temperature.

Step 3-4

In this step compound 3b is obtained by reacting compound 3b-2 with hydrazine. There are no particular restrictions on the solvent used in the reaction as long as it will dissolve the starting raw materials to a certain extent and will not impede the reaction, but ethanol, propanol, or another such alcohol-based solvent is preferable. The reaction will also proceed in the absence of a solvent. The hydrazine is used in an amount of 1 to 20 equivalents with respect to compound

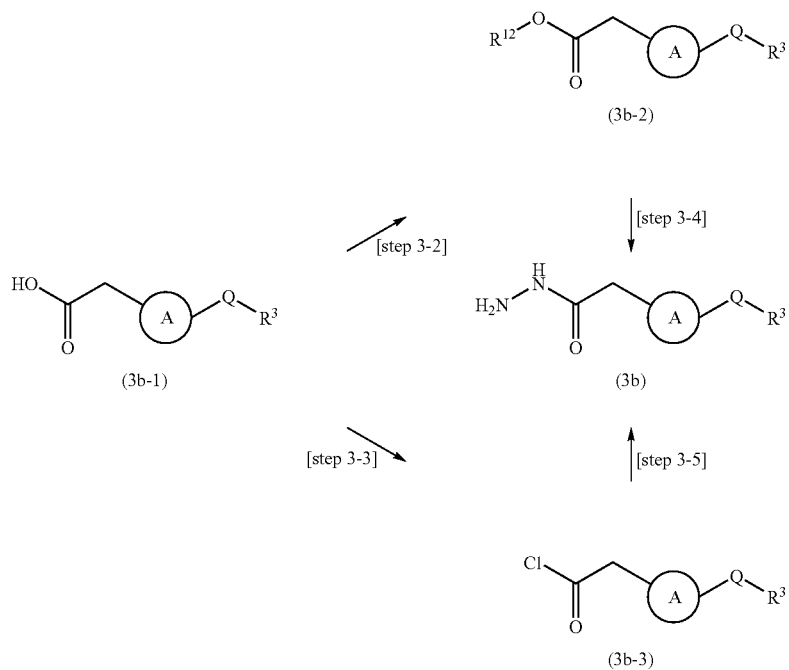

(wherein $R^{12}$ represents a $C_{1-6}$ alkyl group, and A, Q, and $R^3$ are defined the same as above.)

The various compounds in the step illustrated above can be the commercially available product that is used as is, or can be manufactured by the known method from the commercially available product.

Step 3-2

In this step compound 3b-2 is obtained by esterifying compound 3b-1 in the presence of an acid. Compound 3b-2 can be obtained by the same method as in step 1-6.

Step 3-3

In this step compound 3b-3 is obtained by reacting compound 3b-1 with a halogenation agent. There are no particular 3b-2. The reaction temperature is from room temperature to the reflux temperature, and the reaction duration is from 1 to 72 hours.

Step 3-5

In this step compound 3b is obtained by reacting compound 3b-3 with hydrazine in the presence of a base. There are no particular restrictions on the solvent used in the reaction as long as it will dissolve the starting raw materials to a certain extent and will not impede the reaction, but ethanol, propanol, or another such alcohol-based solvent is preferable. The reaction will also proceed in the absence of a solvent. The hydrazine is used in an amount of 1 to 20 equivalents with respect to compound 3b-3. Examples of bases that can be used may include triethylamine, sodium hydroxide, and potassium hydroxide, and the base is used in an amount of 1 to 1.5 equivalents with respect to compound 3b-3. The reaction temperature is from room temperature to the reflux temperature, and the reaction duration is from 1 to 72 hours.

Manufacturing Method 3-3
Method for Manufacturing Compound 3b-4 (Compound 3b)

lents with respect to compound 3b-6. The reaction temperature is from 0° C. to the reflux temperature, and the reaction duration is from 5 minutes to 6 hours.

Step 3-8
In this step compound 3b-4 is obtained by reacting compound 3b-8 with hydrazine. Compound 3b-4 can be manufactured by the same method as in step 3-4.

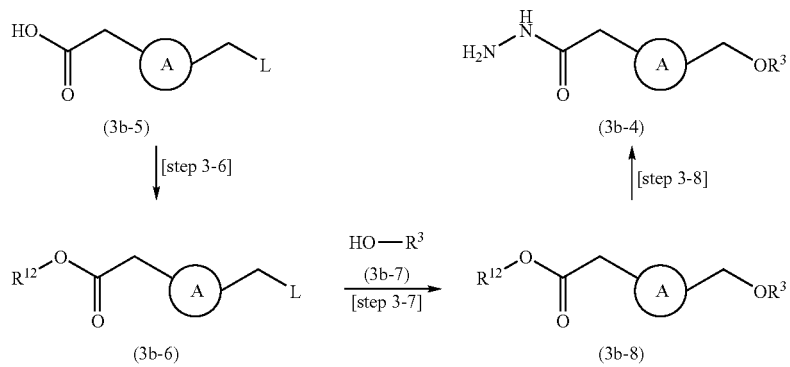

(wherein $R^{12}$ represents a $C_{1-6}$ alkyl group, and A, $R^3$, and L are defined the same as above.)

The various compounds in the step illustrated above can be the commercially available product that is used as is, or can be manufactured by the known method from the commercially available product.

Step 3-6
In this step compound 3b-6 is obtained by esterification in which compound 3b-5 is reacted with diazomethane or trimethylsilyldiazomethane. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, benzene, toluene, and other such aromatic hydrocarbon-based solvents, methanol, ethanol, and other such alcohol-based solvents, methylene chloride, hexane, and mixtures of these. The diazomethane or trimethylsilyldiazomethane is used in an amount of 1 to 2 equivalents with respect to compound 3b-5. The reaction temperature is from 0° C. to room temperature, and the reaction duration is from 10 minutes to 24 hours.

Step 3-7
In this step compound 3b-8 is obtained by reacting compound 3b-6 with 3b-7 in the presence of a base. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, benzene, toluene, and other such aromatic hydrocarbon-based solvents, N,N-dimethylformamide, N-methylpyrrolidinone, and other such amide-based solvents, methanol, ethanol, and other such alcohol-based solvents, dimethyl sulfoxide, and mixtures of these. Examples of bases that can be used may include sodium hydride, potassium tert-butoxide, sodium ethoxide, sodium methoxide, N,N-diisopropylethylamine, triethylamine, potassium hydroxide, sodium hydroxide, potassium carbonate, and sodium carbonate. The base is used in an amount of 1 to 5 equivalents with respect to compound 3b-6. Compound 3b-7 is used in an amount of 1 to 20 equiva- Manufacturing Method 4
Typical Method for Manufacturing Compound 4a (Compound I)

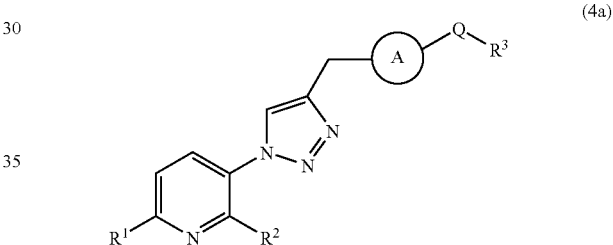

(wherein A, $R^1$, $R^2$, Q, and $R^3$ are defined the same as above.)

Manufacturing Method 4-1
Method for Manufacturing Compound 4a (Compound I)

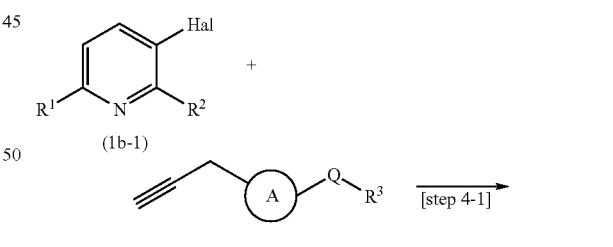

(wherein Hal, A, $R^1$, $R^2$, Q, and $R^3$ are defined the same as above.)

Compound 1b-1 can be the commercially available product that is used as is, or can be manufactured by the known method from the commercially available product.

Compound 4b can be manufactured by the known method from the commercially available product, or it can be manufactured by the methods described in the manufacturing examples in the examples, and by the methods described in Manufacturing Method 4-2, etc.

Step 4-1

In this step compound 4a is obtained by reacting compound 1b-1 with compound 4b and a catalytic amount of copper in the presence of an azidation agent. There are no particular restrictions on the solvent used in the reaction as long as it will dissolve the starting raw materials to a certain extent and will not impede the reaction, but a mixed solvent of dimethyl sulfoxide and water or of tert-butanol and water is preferable. Examples of azidation agents that can be used may include sodium azide and trimethylsilyl azide. The azidation agent is used in an amount of 1 to 1.5 equivalents with respect to compound 1b-1. The copper can be copper(I) iodide, copper (I) bromide, copper(I) chloride, or another such monovalent copper. Alternatively, this may be a compound that will produce monovalent copper in the reaction system, such as copper(II) sulfate-copper(0). The copper is used in an amount of 0.1 to 1.0 equivalent with respect to compound 1b-1. A catalytic amount of an amine-based ligand, such as (1S,2S)—N, N'-dimethylcyclohexane-1,2-diamine, can be added to raise the reaction velocity. The reaction can also be conducted under microwave irradiation. The reaction temperature is from room temperature to the reflux temperature, and the reaction duration is from 5 minutes to 48 hours.

Manufacturing Method 4-2

Method for Manufacturing Compound 4b

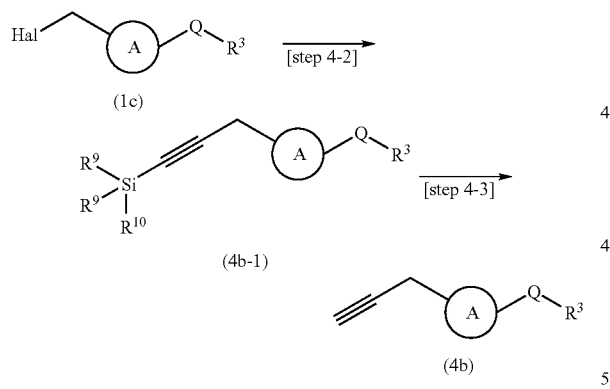

(wherein Hal, A, $R^3$, $R^9$, $R^{10}$, and Q are defined the same as above.)

Compound 1c can be the commercially available product that is used as is, or can be manufactured by the known method from the commercially available product. Furthermore, it can be manufactured by the methods described in the manufacturing examples in the examples, and by the methods described in Manufacturing Method 1-11, etc.

Step 4-2

In this step compound 4b-1 is obtained by reacting compound 1c with an ethynylsilane derivative. Compound 4b-1 can be obtained by reacting compound 1c with a Grignard reagent obtained by reacting an ethynylsilane derivative with a Grignard reagent. A copper compound such as copper(I) bromide or copper(I) iodide may also be added to obtain better results. Examples of ethynylsilane derivatives that can be used may include trimethylsilyl acetylene, triethylsilyl acetylene, triisopropylsilyl acetylene, and tert-butyldimethylsilyl acetylene. An alkyl magnesium halide such as ethyl magnesium bromide or isopropyl magnesium chloride can be used as the Grignard reagent. The ethynylsilane derivative can be used in an amount of 1 to 3 equivalents with respect to compound 1c. The Grignard reagent can be used in an amount of 1 to 3 equivalents with respect to compound 1c. The copper compound can be used in an amount of 0.1 to 3 equivalents with respect to compound 1c. The reaction temperature is from room temperature to the reflux temperature, and the reaction duration is from 1 to 72 hours.

Step 4-3

In this step compound 4b is obtained by deprotecting the trialkylsilyl group of compound 4b-1. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, methanol, ethanol, and other such alcohol-based solvents, N,N-dimethylformamide, N-methylpyrrolidinone, and other such amide-based solvents, acetonitrile, dimethyl sulfoxide, water, and mixtures of these. Examples of bases that can be used may include potassium carbonate, sodium hydroxide, tetrabutylammonium fluoride, potassium fluoride, and cesium fluoride. The base is used in an amount of 0.05 to 10 equivalents with respect to compound 4b-1. The reaction temperature is from 0° C. to the reflux temperature, and the reaction duration is from 5 minutes to 24 hours.

Manufacturing Method 5

Typical Method for Manfacturing Compound 5a (Compound I)

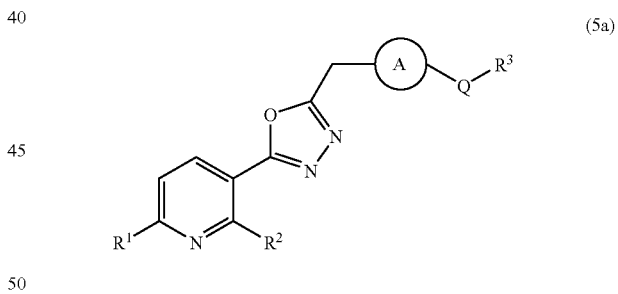

(wherein A, $R^1$, $R^2$, Q, and $R^3$ are defined the same as above.)

Manufacturing Method 5-1

Method for Manufacturing Compound 5a (Compound I)

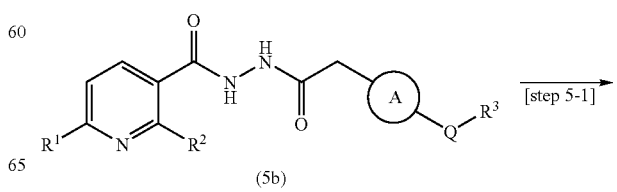

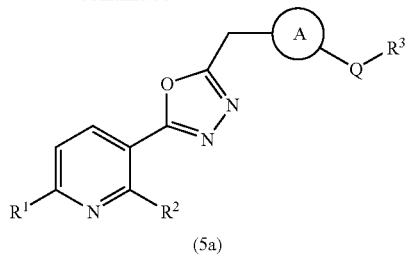

(wherein A, $R^1$, $R^2$, Q, and $R^3$ are defined the same as above.)

Step 5-1

In this step compound 5a is obtained by reacting compound 5b with a phosphorus halide. There are no particular restrictions on the solvent used in the reaction as long as it will dissolve the starting raw materials to a certain extent and will not impede the reaction, but examples of solvents that can be used may include diethyl ether and other such ether-based solvents, benzene, toluene, and other such aromatic hydrocarbon-based solvents, N,N-dimethylformamide, acetonitrile, and chloroform, and the phosphorus halide can also be used as the solvent. Examples of phosphorus halides that can be used may include phosphorus oxychloride, phosphorus trichloride, and phosphorus tribromide. The phosphorus halide is used in an amount of from 1 equivalent to the solvent amount with respect to compound 5b. The reaction temperature is from room temperature to the reflux temperature, and the reaction duration is from 10 minutes to 12 hours.

Compound 5a can also be obtained from compound 5b by the methods described below as Alternative Method 1 and Alternative Method 2.

Alternative Method 1: Compound 5a can be obtained by reacting compound 5b with diphosphorus pentoxide. There are no particular restrictions on the solvent used in the reaction as long as it will dissolve the starting raw materials to a certain extent and will not impede the reaction, but examples of solvents that can be used may include toluene, xylene, and other such aromatic hydrocarbon-based solvents. The diphosphorus pentoxide is used in an amount of 1 to 20 equivalents with respect to compound 5b. The reaction temperature is from room temperature to the reflux temperature, and the reaction duration is from 10 minutes to 12 hours.

Alternative Method 2: Compound 5a can be obtained by reacting compound 5b with thionyl chloride. There are no particular restrictions on the solvent used in the reaction as long as it will dissolve the starting raw materials to a certain extent and will not impede the reaction, but examples of solvents that can be used may include benzene, toluene, and other such aromatic hydrocarbon-based solvents, acetonitrile, chloroform, and methylene chloride, and the thionyl chloride can also be used as the solvent. A catalytic amount of pyridine can also be added to this reaction to obtain better results. The thionyl chloride is used in an amount of from 1 equivalent to the solvent amount with respect to compound 5b. The reaction temperature is from room temperature to the reflux temperature, and the reaction duration is from 10 minutes to 12 hours.

Manufacturing Method 5-2

Method for Manufacturing Compound 5b

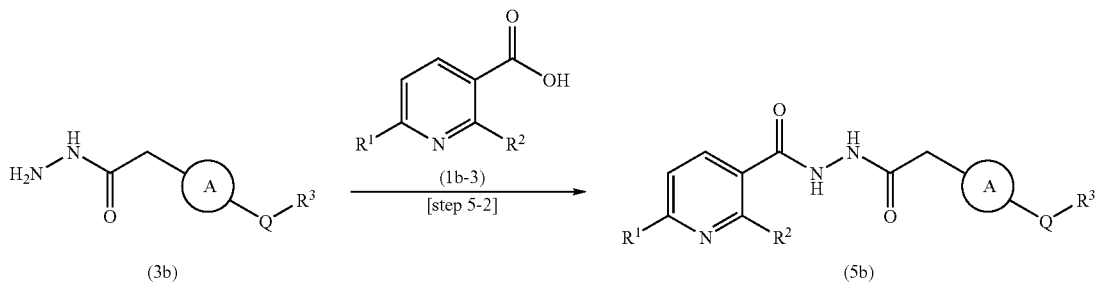

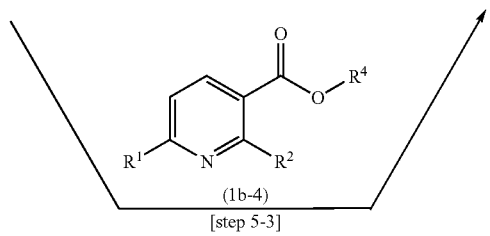

(wherein A, $R^1$, $R^2$, $R^3$, $R^4$, and Q are defined the same as above.)

Compound 3b, compound 1b-3, and compound 1b-4 can be the commercially available product that is used as is, or can be manufactured by the known method from the commercially available product, or by the methods described in this Specification.

Step 5-2

In this step compound 5b is obtained using a condensing agent to condense compound 3b and compound 1b-3. There are no particular restrictions on the solvent used in the reaction as long as it will dissolve the starting raw materials to a certain extent and will not impede the reaction, but examples of solvents that can be used may include dichloromethane, chloroform, and other such halogen-based solvents, dimethyl sulfoxide and other such sulfoxides, ethyl acetate and other such esters, tetrahydrofuran, 1,4-dioxane, and other such ether-based solvents, and N,N-dimethylformamide, N,N-dimethylacetamide and other such amide-based solvents. Examples of condensation agents that can be used may include (1H-1,2,3-benzotriazol-1-yloxy(tri(dimethylamino))phosphonium hexafluorophosphate) (hereinafter referred to as Bop), WSC, DCC, carbonyldiimidazole (hereinafter referred to as CDI), and diethylphosphoryl cyanide. Compound 1b-3 is used in an amount of 0.8 to 1.2 equivalents with respect to compound 3b. The condensation agent is used in an amount of 0.8 to 1.2 equivalents with respect to compound 3b. An organic base, such as triethylamine, can also be added in an amount of 1 to 5 equivalents in this step. The reaction temperature is from room temperature to the reflux temperature, and the reaction duration is from 10 minutes to 30 hours.

Step 5-3

In this step compound 5b is obtained by reacting compound 3b with compound 1b-4. There are no particular restrictions on the solvent used in the reaction as long as it will dissolve the starting raw materials to a certain extent and will not impede the reaction, but examples of solvents that can be used may include ethanol, propanol, and other such alcohol-based solvents, tetrahydrofuran, 1,4-dioxane, and other such ether-based solvents, N,N-dimethylformamide, N-methylpyrrolidinone, and other such amide-based solvents, dimethyl sulfoxide, and mixtures of these. Compound 3b can also be used as the solvent. Compound 3b is used in an amount of from 1 equivalent to the solvent amount with respect to compound 1b-4. The reaction temperature is from 0° C. to the reflux temperature, and the reaction duration is from 10 minutes to 24 hours.

Manufacturing Method 6

Typical Method for Manufacturing Compound 6a (Compound I)

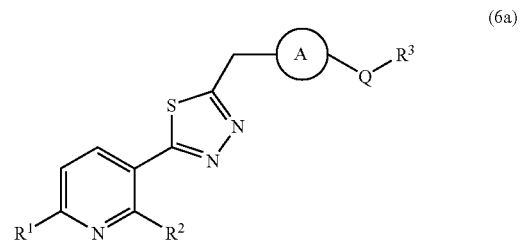

(6a)

(wherein A, R$^1$, R$^2$, Q, and R$^3$ are defined the same as above.)

Manufacturing Method 6-1

Method for Manufacturing Compound 6a (Compound I)

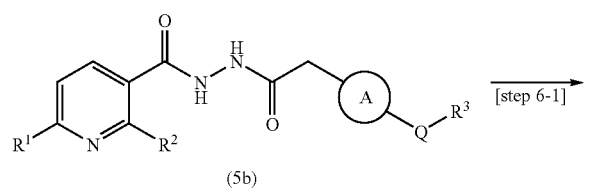

(5b)

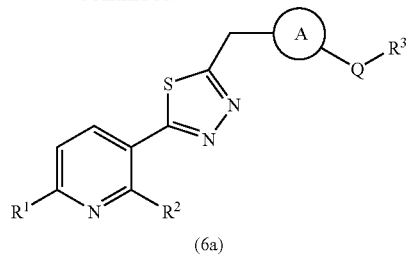

(6a)

(wherein A, R$^1$, R$^2$, Q, and R$^3$ are defined the same as above.)

Compound 5b can be manufactured by the method described in Manufacturing Method 5-2.

Step 6-1

In this step compound 6a is obtained by reacting compound 5b with 2,4-bis(4-methoxyphenyl)-1,3-dithia-2,4-diphosphetane-2,4-disulfide (Lawesson's reagent) or diphosphorus pentasulfide. There are no particular restrictions on the solvent used in the reaction as long as it will dissolve the starting raw materials to a certain extent and will not impede the reaction, but examples of solvents that can be used may include benzene, toluene, and other such aromatic hydrocarbon-based solvents. The Lawesson's reagent or diphosphorus pentasulfide is used in an amount of 1 to 20 equivalents with respect to compound 5b. The reaction temperature is from room temperature to the reflux temperature, and the reaction duration is from 10 minutes to 12 hours.

Manufacturing Method 7

Typical Method for Manufacturing Compound 7a (Compound I)

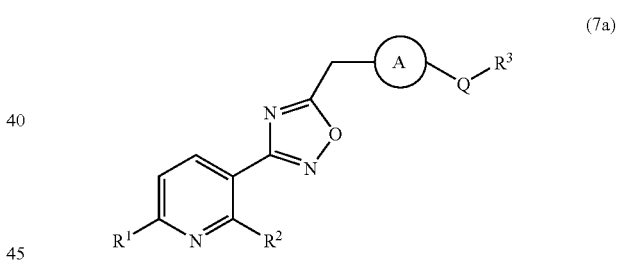

(7a)

(wherein A, R$^1$, R$^2$, Q, and R$^3$ are defined the same as above.)

Manufacturing Method 7-1

Method for Manufacturing Compound 7a (Compound I)

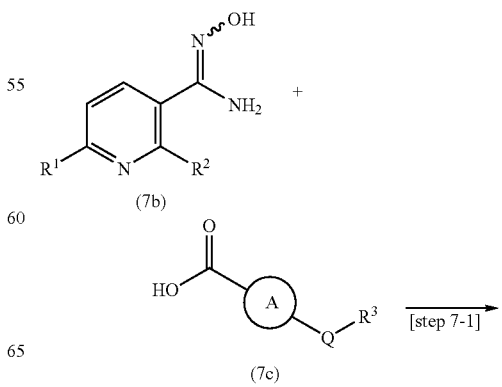

(7b)

(7c)

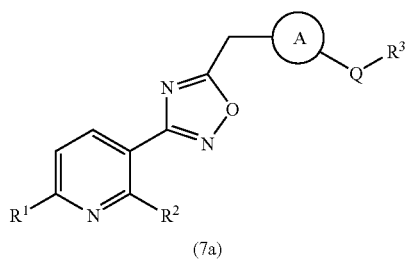

(7a)

(wherein A, $R^1$, $R^2$, Q, and $R^3$ are defined the same as above.)

Compound 7b and compound 7c can be the commercially available product that is used as is, or can be manufactured by the known method from the commercially available product.

Step 7-1

In this step compound 7a is obtained by converting compound 7c into an acid anhydride, an acid chloride, or an active ester, and then reacting it with compound 7b. The step of converting compound 7c into an acid anhydride is a step of obtaining an acid anhydride of compound 7c by dehydrating with a condensation agent in the solvent. There are no particular restrictions on the solvent that is used, but examples of solvents that can be used may include dichloromethane, chloroform, and other such halogen-based solvents, dimethyl sulfoxide and other such sulfoxides, ethyl acetate and other such esters, tetrahydrofuran, 1,4-dioxane, and other such ether-based solvents, and N,N-dimethylformamide, N,N-dimethylacetamide, and other such amide-based solvents. WSC, DCC, and the like can be used as the condensation agent. The condensation agent is used in an amount of 1 to 1.5 equivalents with respect to compound 7c. If needed, an organic base, such as triethylamine, may be added in an amount from 1 equivalent to an excess amount. The reaction temperature is from 0° C. to 80° C., and the reaction duration is from 10 minutes to 30 hours.

The step of converting compound 7c into an acid chloride is carried out by reacting an acid chloride synthesis reagent in an amount of from 1 equivalent to a catalytic amount with respect to compound 7c and in the presence of a solvent such as dichloromethane, benzene, or toluene, or in the absence of a solvent. A catalytic amount of N,N-dimethylformamide may be added to the reaction system. Examples of acid chloride synthesis reagents that can be used may include thionyl chloride, oxalyl chloride, phosphorus trichloride, and phosphorus pentachloride. The reaction temperature is from 0° C. to the reflux temperature, and the reaction duration is from 10 minutes to 24 hours.

The step of converting compound 7c into an active ester is carried out by reacting compound 7c and an active ester synthesis reagent in the presence of DCC or another such condensation agent and in a solvent such as 1,4-dioxane or tetrahydrofuran. N-hydroxysuccinimide can be used as the active ester synthesis reagent. The active ester synthesis reagent and the condensation agent are used in an amount of 1 to 1.5 equivalents with respect to compound 7c. The reaction temperature is from 0° C. to normal temperature. The reaction duration is from 2 to 24 hours.

The step of reacting the acid anhydride, acid chloride, or active ester with compound 7b is a step of obtaining compound 7a by reacting in the presence of a base. Examples of bases that can be used may include pyridine, triethylamine, sodium hydride, sodium methoxide, and sodium ethoxide. There are no particular restrictions on the solvent used in the reaction as long as it will dissolve the starting raw materials to a certain extent and will not impede the reaction, but examples of solvents that can be used may include dichloromethane, chloroform, and other such halogen-based solvents, dimethyl sulfoxide and other such sulfoxides, ethyl acetate and other such esters, tetrahydrofuran, 1,4-dioxane, and other such ether-based solvents, methanol, ethanol, and other such alcohol-based solvents, and 1-methyl-2-pyrrolidinone (hereinafter referred to as "NMP"), N,N-dimethylformamide, N,N-dimethylacetamide, and other such amide-based solvents. The base is used in an amount of 1 to 10 equivalents with respect to compound 7b. The reaction temperature is from room temperature to the reflux temperature, and the reaction duration is from 10 minutes to 24 hours.

Manufacturing Method 7-2

Method for Manufacturing Compound 7b

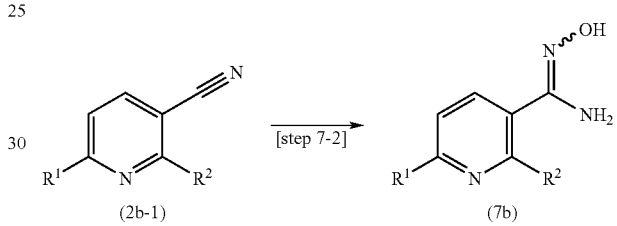

(wherein $R^1$ and $R^2$ are defined the same as above.)

Compound 2b-1 can be the commercially available product that is used as is, or can be manufactured by the known method from the commercially available product. Furthermore, it can be manufactured by the methods described in the manufacturing examples in the examples, and by the methods described in Manufacturing Method 2-3, etc.

Step 7-2

In this step compound 7b is obtained by reacting compound 2b-1 with hydroxylammonium chloride. Examples of bases that can be used in the reaction may include pyridine, sodium acetate, potassium acetate, sodium hydrogencarbonate, sodium carbonate, sodium hydroxide, and potassium hydroxide. There are no particular restrictions on the solvent used in the reaction as long as it will dissolve the starting raw materials to a certain extent and will not impede the reaction, but examples of solvents that can be used may include dichloromethane, chloroform, and other such halogen-based solvents, dimethyl sulfoxide and other such sulfoxides, tetrahydrofuran, 1,4-dioxane, and other such ether-based solvents, methanol, ethanol, and other such alcohol-based solvents, NMP, N,N-dimethylformamide, N,N-dimethylacetamide, and other such amide-based solvents, pyridine, water, and mixtures of these. The hydroxylammonium chloride is used in an amount of 1 to 5 equivalents with respect to compound 2b-1. The base is used in an amount of from 1 equivalent to an excess amount with respect to compound 2b-1. The reaction temperature is from 0° C. to the reflux temperature, and the reaction duration is from 10 minutes to 48 hours.

Manufacturing Method 8
Typical Method for Manufacturing Compound 8a (Compound I)

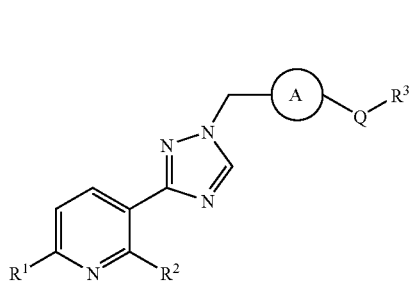

(wherein A, $R^1$, $R^2$, Q, and $R^3$ are defined the same as above.)

Manufacturing Method 8-1
Method for Manufacturing Compound 8a (Compound I)

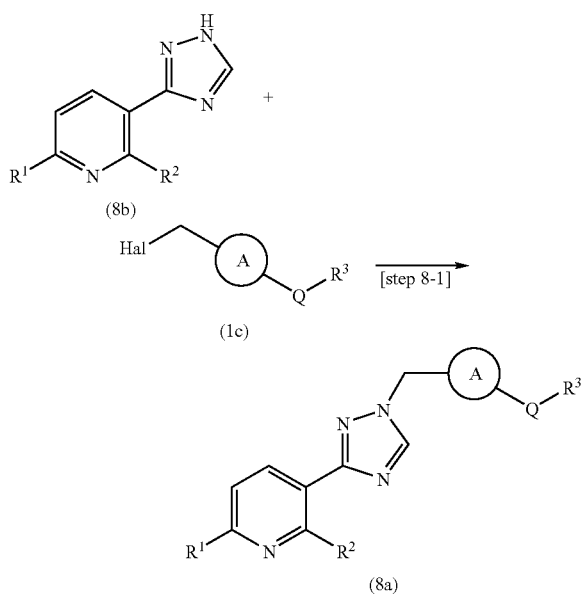

(wherein A, $R^1$, $R^2$, Q, Hal, and $R^3$ are defined the same as above.)

Compound 8b and compound 1c can be manufactured by the known method from the commercially available product, or can be synthesized by the methods described in this Specification.

Step 8-1

In this step compound 8a is obtained by reacting compounds 8b and 1c in the presence of a base. Compound 8a can be obtained by the same method as in step 2-1.

Manufacturing Method 8-2
Method for Manufacturing Compound 8b

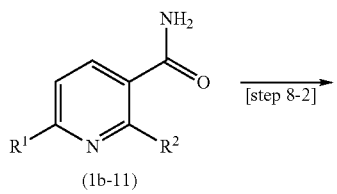

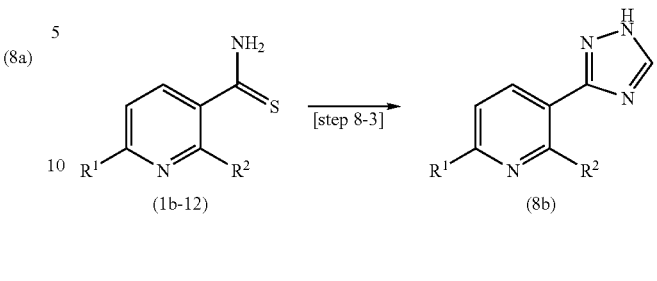

(wherein $R^1$ and $R^2$ are defined the same as above.)

Compound 1b-11 can be manufactured by the known method from a commercially available product, or can be synthesized by the methods described in this Specification.

Step 8-2

In this step compound 1b-12 is obtained by converting compound 1b-11 into a thioamide. Compound 1b-12 can be obtained by reacting compound 1b-11 with 2,4-bis(4-methoxyphenyl)-1,3-dithia-2,4-diphosphetane-2,4-disulfide (Lawesson's reagent). There are no particular restrictions on the solvent used in the reaction as long as it will dissolve the starting raw materials and reagents to a certain extent and will not impede the reaction, but examples of solvents that can be used may include tetrahydrofuran, 1,4-dioxane, and other such ether-based solvents, toluene, xylene, and other such aromatic hydrocarbon-based solvents, dichloroethane and other such halogen-based solvents, and mixtures of these. The Lawesson's reagent is used in an amount of 0.5 to 5 equivalents with respect to compound 1b-11. The reaction temperature is from room temperature to the reflux temperature, and the reaction duration is from 10 minutes to 48 hours.

Compound 1b-12 can also be obtained from compound 1b-11 by the methods described in the following Alternative Methods 1 and 2.

Alternative Method 1:

Compound 1b-12 can be obtained by reacting compound 1b-11 with diphosphorus pentasulfide. There are no particular restrictions on the solvent used in the reaction as long as it will dissolve the starting raw materials and reagents to a certain extent and will not impede the reaction, but examples of solvents that can be used may include tetrahydrofuran, 1,4-dioxane, and other such ether-based solvents, benzene, toluene, xylene, and other such aromatic hydrocarbon-based solvents, dichloromethane and other such halogen-based solvents, and mixtures of these. The diphosphorus pentasulfide is used in an amount of 0.5 to 5 equivalents with respect to compound 1b-11. The reaction temperature is from room temperature to the reflux temperature of the solvent, and the reaction duration is from 10 minutes to 48 hours.

Alternative Method 2:

Compound 1b-12 can be obtained by reacting compound 1b-11 with phosphorus pentasulfide and hexamethyldisiloxane. There are no particular restrictions on the solvent used in the reaction as long as it will dissolve the starting raw materials and reagents to a certain extent and will not impede the reaction, but examples of solvents that can be used may include tetrahydrofuran, 1,4-dioxane, and other such ether-based solvents, benzene, toluene, xylene, and other such aromatic hydrocarbon-based solvents, dichloroethane and other such halogen-based solvents, hexamethylphosphorylamide (HMPA), and mixtures of these. The hexamethyldisiloxane is used in an amount of 0.5 to 3 equivalents with respect to compound 1b-11, and the phosphorus pentasulfide is used in an amount of 1 to 6 equivalents with respect to compound 1b-11. The reaction temperature is from room temperature to the reflux temperature of the solvent, and the reaction duration is from 10 minutes to 48 hours.

Step 8-3

In this step compound 8b is obtained by allowing formic acid hydrazide to act on compound 1b-12. There are no particular restrictions on the solvent used in the reaction as long as it will dissolve the starting raw materials and reagents to a certain extent and will not impede the reaction, but examples of solvents that can be used may include tetrahydrofuran, 1,4-dioxane, and other such ether-based solvents, benzene, toluene, xylene, and other such aromatic hydrocarbon-based solvents, dichloroethane and other such halogen-based solvents, and mixtures of these. The formic acid hydrazide can also be used as the solvent. The formic acid hydrazide is used in an amount of from 3 equivalents to the solvent amount with respect to compound 1b-12. The reaction temperature is from 60° C. to 140° C.

Manufacturing Method 9
Typical Method for Manufacturing Compound 9a (Compound I)

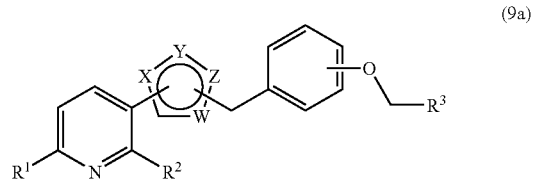

(wherein $R^1$, $R^2$, $R^3$, W, X, Y, and Z are defined the same as above.)

Manufacturing Method 9-1
Method for Manufacturing Compound 9a (Compound I)

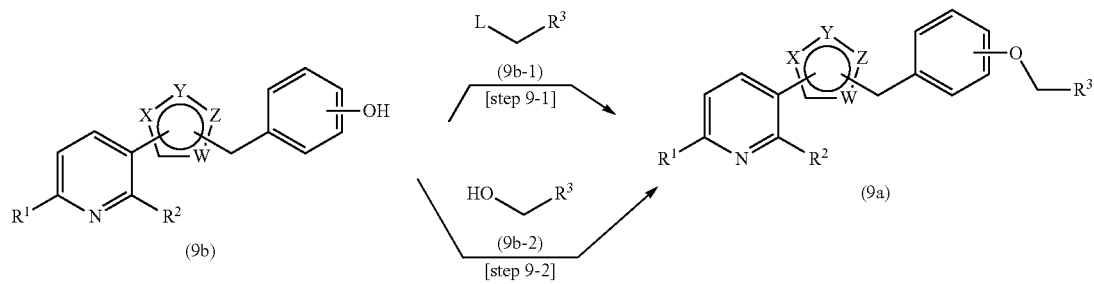

(wherein $R^1$, $R^2$, $R^3$, W, X, Y, and Z are defined the same as above.)

Compound 9b can be synthesized by the methods described in the manufacturing examples in the examples. Compound 9b-1 and compound 9b-2 can be the commercially available product that is used as is, or can be manufactured by the known method from the commercially available product.

Step 9-1

In this step compound 9a is obtained by adding 1 equivalent of a base to compound 9b to convert it into a phenoxide ion, and then reacting compound 9b-1.

Phenoxide ion production: A phenoxide ion can be obtained by adding 1 equivalent of a base to compound 9b in a solvent such as tetrahydrofuran or methanol. Examples of bases that can be used may include potassium hydroxide, sodium hydroxide, potassium carbonate, sodium carbonate, and potassium tert-butoxide, with sodium hydroxide being preferable. The solvent is preferably concentrated for use in the following reaction. The reaction temperature is room temperature, and the reaction duration is from 1 minute to 1 hour.

Reaction of phenoxide ion with compound 9b-1: Compound 9a can be obtained by reacting the phenoxide ion with compound 9b-1. There are no particular restrictions on the solvent used in this reaction as long as it will dissolve the starting materials to a certain extent and will not impede the reaction, but examples of solvents that can be used may include N,N-dimethylformamide, 1-methyl-2-pyrrolidinone, hexamethylphosphoramide, and other such amide-based solvents, dimethyl sulfoxide, and mixtures of these. Compound 9b-1 is used in an amount of 1 to 3 equivalents with respect to compound 9b. The reaction temperature is from room temperature to the reflux temperature, and the reaction duration is from 10 minutes to 48 hours.

Compound 9a can also be obtained from compound 9b by the method described below as Alternative Method 1.

Alternative Method 1: Compound 9a can be obtained by reacting compound 9b with compound 9b-1 in the presence of a base. There are no particular restrictions on the solvent used in the reaction as long as it will dissolve the starting raw materials to a certain extent and will not impede the reaction, but examples of solvents that can be used may include tetrahydrofuran, diethyl ether, and other such ether-based solvents, benzene, toluene and other such aromatic hydrocarbon-based solvents, N,N-dimethylformamide, 1-methyl-2-pyrrolidinone, and other such amide-based solvents, dimethyl sulfoxide, and mixtures of these. Examples of bases that can be used may include sodium hydride, potassium carbonate, sodium carbonate, cesium carbonate, potassium hydroxide, and sodium hydroxide. A catalytic amount of sodium iodide, potassium iodide, or tetrabutylammonium iodide can also be added to obtain better results. The base is used in an amount of 1 to 1.5 equivalents with respect to compound 9b. The reaction temperature is from room temperature to the reflux temperature, and the reaction duration is from 10 minutes to 48 hours.

Step 9-2

In this step compound 9a is obtained by reacting compound 9b with compound 9b-2. Compound 9a can be manufactured by the same method as in step 1-19.

Manufacturing Method 9-2
Method for Manufacturing Compound 9b

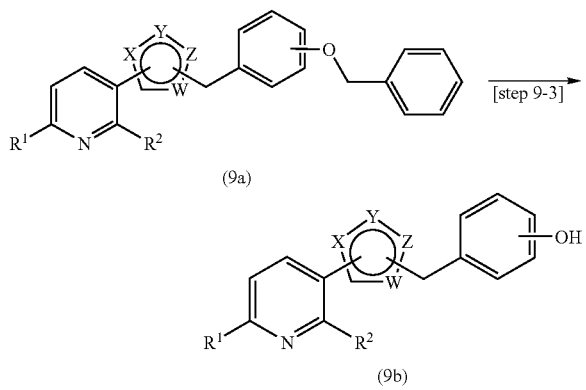

(wherein $R^1$, $R^2$, W, X, Y, and Z are defined the same as above.)

Compound 9c can be manufactured by the methods described in the manufacturing examples in the examples, and by the methods described in Manufacturing Method 1, Manufacturing Method 2, Manufacturing Method 3, Manufacturing Method 4, Manufacturing Method 5, Manufacturing Method 6, Manufacturing Method 7, Manufacturing Method 8, etc.

Step 9-3

In this step compound 9b is obtained by allowing an acid to act on compound 9c. An additive such as thioanisole may be added to the reaction system to obtain better results. There are no particular restrictions on the solvent used in the reaction as long as it will dissolve the starting raw materials to a certain extent and will not impede the reaction, but examples of solvents that can be used may include diethyl ether, tetrahydrofuran, and other such ether-based solvents, methylene chloride, and trifluoroacetic acid. Examples of acids that can be used may include organic acids such as trifluoroacetic acid and methanesulfonic acid, inorganic acids such as sulfuric acid, and Lewis acids such as boron trifluoride diethyl etherate. Examples of additives that can be used may include thioanisole, ethanethiol, and dl-methionine. The acid is used in an amount of from 1 equivalent to the solvent amount with respect to compound 9c. The additive is used in an amount of 1 to 5 equivalents with respect to compound 9c. The reaction temperature is from 0° C. to the reflux temperature, and the reaction duration is from 10 minutes to 72 hours.

Compound 9b can also be obtained from compound 9c by the method described below as Alternative Method 1.

Alternative Method 1: Compound 9b can be obtained by reacting compound 9c with boron tribromide or boron trichloride. There are no particular restrictions on the solvent used in the reaction as long as it will dissolve the starting raw materials to a certain extent and will not impede the reaction, but the use of methylene chloride is preferable. The boron tribromide or boron trichloride is used in an amount of 1 to 10 equivalents with respect to compound 9c. The reaction temperature is from −78° C. to room temperature, and the reaction duration is from 30 minutes to 24 hours.

EXAMPLES

Examples and pharmaceutical test examples according to the present invention will now be given to describe the present invention in further detail, but the present invention is not restricted to or by the following examples, etc. A person skilled in the art will be able to work the present invention by making various modifications to the examples given below, and such modifications are encompassed by the patent claims.

The abbreviations used below are defined as follows.

NMP: 1-methyl-2-pyrrolidinone

THF: tetrahydrofuran

DMSO: dimethyl sulfoxide

DMF: N,N-dimethylformamide

NaH: sodium hydride

WSC: 1-ethyl-3-(3-dimethylaminopropyl)carbodiimide hydrochloride

HOBt: 1-hydroxybenzotriazole

LAH: lithium aluminum hydride

TFA: trifluoroacetic acid

Example 1

3-(1-(4-Benzyloxy-benzyl)-1H-[1,2,3]triazol-4-yl)-pyridin-2-ylamine

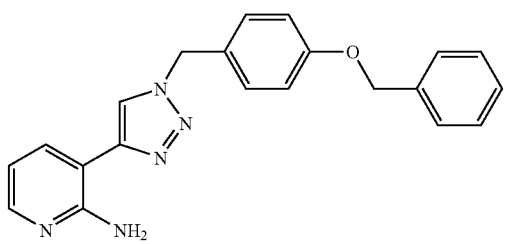

To a solution of a tert-butyl alcohol (500 μL), water (600 μL) and the 3-ethynyl-pyridin-2-ylamine (30 mg) described in Manufacturing Example 1-2 were added 1-benzyloxy-4-chloromethyl-benzene (59 mg), sodium azide (17 mg), copper sulfate (8 mg), and copper (13 mg) at room temperature, which was irradiated for 10 minutes at no higher than 125° C. with 100 W microwaves. Water was added to the reaction mixture, which was filtered through Celite. The filtrate thus obtained was extracted with ethyl acetate, and the organic layer was washed with saturated brine. The organic layer was dried over anhydrous magnesium sulfate and filtered, and then the solvent was evaporated from the filtrate under a reduced pressure. The residue was purified by reverse-phase high performance liquid chromatography (using an acetonitrile-water mobile phase containing 0.1% TFA), which was then further purified by silica gel column chromatography (ethyl acetate:methanol=15:1) to obtain the titled compound (7 mg).

MS m/e (ESI) (MH+) 358.22 (MH+)

$^1$H-NMR spectrum (DMSO-$d_6$) δ (ppm): 5.08 (2H, s), 5.56 (2H, s), 6.60 (1H, dd, J=4.8 Hz, 7.5 Hz), 6.87 (2H, s), 7.01 (2H, d, J=8.8 Hz), 7.30-7.42 (7H, m), 7.81 (1H, dd, J=1.8 Hz, 7.5 Hz), 7.93 (1H, dd, J=1.8 Hz, 4.8 Hz), 8.65 (1H, s).

The starting substance 3-ethynyl-pyridin-2-ylamine was synthesized by the following method.

Manufacturing Example 1-1

3-Trimethylsilanylethynyl-pyridin-2-ylamine

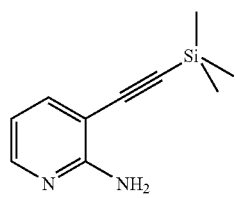

To a NMP (120 mL) solution of 2-amino-3-bromopyridine (5.72 g, 33.1 mmol) were added trimethylsilylacetylene (9.36 mL, 66.2 mmol), tetrakis(triphenylphosphine)palladium(0) (1.91 g, 1.66 mmol), copper(I) iodide (630 mg, 3.31 mmol), and N,N-diisopropylethylamine (11.5 mL, 66.2 mmol) at room temperature, which was stirred for 6 hours at 70° C. under a nitrogen atmosphere. Water was added at 0° C. to the reaction solution, and then extraction was performed with ethyl acetate. The organic layer was washed with water and saturated brine, after which it was dried over anhydrous magnesium sulfate and filtered, and then the filtrate was concentrated under a reduced pressure. The residue was purified by silica gel chromatography (heptane:ethyl acetate=2:1) to obtain the titled compound (5.9 g).

$^1$H-NMR spectrum (DMSO-$d_6$) δ (ppm): 0.225 (9H, s), 6.07 (2H, brs), 6.51 (1H, dd, J=4.9 Hz, 7.5 Hz), 7.49 (1H, dd, J=1.8 Hz, 7.5 Hz), 7.94 (1H, dd, J=1.8 Hz, 4.9 Hz).

Manufacturing Example 1-2

3-Ethynyl-pyridin-2-ylamine

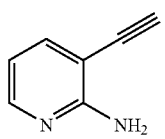

To a THF (120 mL) solution of 3-trimethylsilanylethynyl-pyridin-2-ylamine (5.9 g) described in Manufacturing Example 1-1 was added tetrabutylammonium fluoride (34 mL: 1M THF solution) at 0° C., which was stirred for 25 minutes at room temperature. Water was added at 0° C. to the reaction solution, which was then extracted with ethyl acetate. The organic layer was washed with water and saturated brine, then dried over anhydrous magnesium sulfate, and filtered, after which the filtrate was concentrated under a reduced pressure. The residue was purified by silica gel chromatography (heptane:ethyl acetate=1:1) to obtain the titled compound (2.3 g).

$^1$H-NMR spectrum (CDCl$_3$) δ (ppm): 3.42 (1H, s), 5.12 (2H, brs), 6.62 (1H, dd, J=4.9 Hz, 7.5 Hz), 7.58 (1H, dd, J=1.8 Hz, 7.5 Hz), 8.05 (1H, dd, J=1.7 Hz, 4.9 Hz).

Alternative Method

Method for synthesizing 3-trimethylsilanylethynyl-pyridin-2-ylamine

Manufacturing Example 1-2-1

2,2-Dimethyl-N-pyridin-2-yl-propionamide

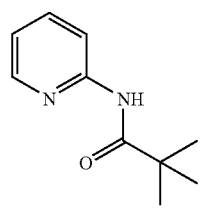

To a methylene chloride (500 mL) solution of 2-aminopyridine (50 g) were added triethylamine (81 mL) and pivaloyl chloride (72 mL) at 0° C., which was stirred for 4 hours and 30 minutes at room temperature. Water was added to the reaction solution, and then extraction was performed with methylene chloride. The organic layer was washed with water and saturated brine, and dried over anhydrous magnesium sulfate and filtered, and then the filtrate was concentrated under a reduced pressure. Potassium carbonate (73 g) was added at 0° C. to a methanol (300 mL) solution of the residue thus obtained, which was stirred for 90 minutes at room temperature. Water was added to the reaction solution, and then extraction was performed with ethyl acetate. The organic layer was washed with saturated brine, then dried over anhydrous magnesium sulfate, and filtered, after which the filtrate was concentrated under a reduced pressure. Heptane (300 mL) was added to the residue, and the precipitated solids were filtered off to obtain the titled compound (80 g). The filtrate was then further concentrated under a reduced pressure, and the residue was purified by silica gel column chromatography (heptane:ethyl acetate=2:1) to obtain the titled compound (12 g).

$^1$H-NMR spectrum (DMSO-$d_6$) δ (ppm): 1.22 (9H, s), 7.06-7.09 (1H, m), 7.72-7.77 (1H, m), 8.01-8.03 (1H, m), 8.29-8.31 (1H, m), 9.71 (1H, s).

Manufacturing Example 1-2-2

N-(3-Iodo-pyridin-2-yl)-2,2-dimethyl-propionamide

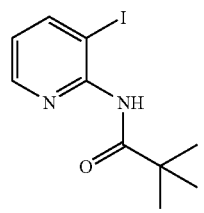

To a mixture of 2,2-dimethyl-N-pyridin-2-yl-propionamide (3.0 g, 17 mmol) described in Manufacturing Example 1-2-1, N,N,N',N'-tetramethylethylenediamine (6.3 mL, 42 mmol)), and THF (60 mL) was added n-butyl lithium (1.6 M n-hexane solution, 30 mL) by drops at −78° C., which was stirred overnight at 0° C. Iodine (6.8 g) was added at −78° C. to the reaction mixture, which was stirred for 1.5 hours at 0° C. Water and a saturated aqueous sodium thiosulfate were added to the reaction mixture, which was then extracted with ethyl acetate. The organic layer was washed with saturated brine, and the solvent was evaporated under a reduced pressure. The residue was purified by silica gel column chromatography (ethyl acetate:heptane=2:1) to obtain the titled compound (2.9 g).

$^1$H-NMR spectrum (CDCl$_3$) δ (ppm): 1.38 (9H, s), 6.85 (1H, dd, J=4.8 Hz, 7.9 Hz), 7.94 (1H, brs), 8.11 (1H, dd, J=1.7 Hz, 7.9 Hz), 8.46 (1H, dd, J=1.7 Hz, 4.6 Hz).

Manufacturing Example 1-2-3

3-Iodo-pyridin-2-ylamine

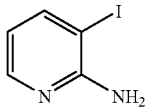

N-(3-Iodo-pyridin-2-yl)-2,2-dimethyl-propionamide (66.2 g, 218 mmol) described in Manufacturing Example 1-2-2, a 5 N aqueous solution (200 mL) of sodium hydroxide, and methanol (200 mL) were stirred under reflux for 1 hour and 20 minutes. The reaction solution was returned to room temperature, and then water was added thereto, which was extracted with ethyl acetate three times. The ethyl acetate layers were combined, which was washed once with saturated brine, and then dried over sodium sulfate. The sodium sulfate was removed by filtration, and the solvent was evaporated under a reduced pressure to obtain the titled compound (41 g).

$^1$H-NMR spectrum (DMSO-d$_6$) δ (ppm): 6.00 (2H, brs), 6.32 (1H, dd, J=4.8 Hz, 7.2 Hz), 7.87 (1H, d, J=7.2 Hz), 7.92 (1H, d, J=4.8 Hz).

Manufacturing Example 1-2-4

3-Trimethylsilanylethynyl-pyridin-2-ylamine

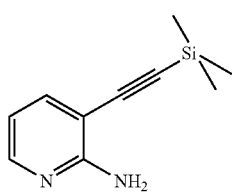

To a mixture of 3-iodo-pyridin-2-ylamine (40 g) described in Manufacturing Example 1-2-3, trimethylsilylacetylene (52 mL), copper(I) iodide (3.5 g), N,N-diisopropylethylamine (64 mL), and NMP (200 mL) was added tetrakis(triphenylphosphine)palladium(0) (10 g), which was stirred for 3 hours and 10 minutes at room temperature under a nitrogen atmosphere. Water was added to the reaction solution, which was then extracted with ethyl acetate 4 times. The solvent was evaporated under a reduced pressure, and the residue was purified by NH silica gel chromatography (heptane:ethyl acetate=4:1). The solution thus obtained was concentrated under a reduced pressure, and the residue was purified by silica gel chromatography (heptane:ethyl acetate=2:1, then 1:1) to obtain the titled compound (28 g).

$^1$H-NMR spectrum (DMSO-d$_6$) δ (ppm): 0.25 (9H, s), 6.09 (2H, brs), 6.51-6.57 (1H, m), 7.50-7.55 (1H, m), 7.95-7.99 (1H, m).

Example 2

5-(1-(4-Benzyloxy-benzyl)-1H-[1,2,3]triazol-4-yl)-2-methyl-pyridine

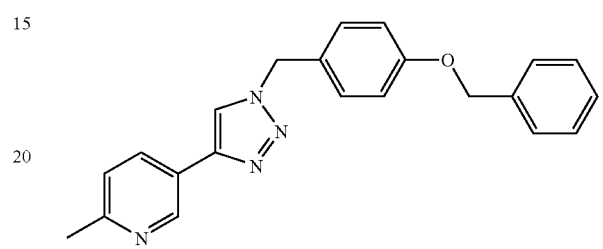

The titled compound (3.5 mg) was obtained from 5-ethynyl-2-methyl-pyridine (16 mg) described in Manufacturing Example 2-1 and 1-benzyloxy-4-chloromethyl-benzene (35 mg) by the same method as in Example 1.

MS m/e (ESI) (MH$^+$) 357.26 (MH$^+$)

The starting substance 5-ethynyl-2-methyl-pyridine was synthesized by the following method.

Manufacturing Example 2-1

5-Ethynyl-2-methyl-pyridine

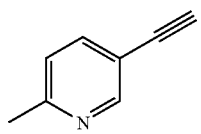

To a NMP solution (20 mL) of 5-bromo-2-methyl-pyridine (1.0 g) were added trimethylsilylacetylene (1.2 mL), tetrakis(triphenylphosphine)palladium(0) (130 mg), copper(I) iodide (44 mg), and N,N-diisopropylethylamine (2.0 mL), which was stirred under a nitrogen atmosphere for 2 hours at 65° C. Water was added at room temperature to the reaction mixture, which was then extracted with ethyl acetate. The organic layer was washed with water and saturated brine, dried over anhydrous magnesium sulfate and filtered, after which the solvent was evaporated from the filtrate under a reduced pressure. The residue was purified by silica gel column chromatography (heptane:ethyl acetate=5:1) to obtain a mixture (810 mg) of 5-bromo-2-methyl-pyridine and 2-methyl-5-trimethylsilanylethynyl-pyridine. Then, to a solution of THF (10 mL) and ethanol (5 mL) of the mixture (810 mg) of 5-bromo-2-methyl-pyridine and 2-methyl-5-trimethylsilanylethynyl-pyridine was added potassium carbonate (1.2 g) at room temperature, which was stirred for 2 hours and 30 minutes at room temperature. Water was added at room temperature to the reaction mixture, which was then extracted with ethyl acetate. The organic layer was washed with water and saturated brine, dried over anhydrous magnesium sulfate, and filtered, after which the solvent was evaporated from the filtrate under a reduced pressure, and the residue was purified by silica gel column chromatography (heptane:ethyl acetate=5:1) to obtain the titled compound (55 mg).

$^1$H-NMR spectrum (DMSO-d$_6$) δ (ppm): 2.26 (3H, s), 4.13 (1H, s), 7.06 (1H, d, J=8.1 Hz), 7.56 (1H, dd, J=2.2 Hz, 8.1 Hz), 8.32 (1H, d, J=1.7 Hz)

Manufacturing Example 3

5-(1-(4-Benzyloxy-benzyl)-1H-[1,2,3]triazol-4-yl)-pyridin-2-ylamine

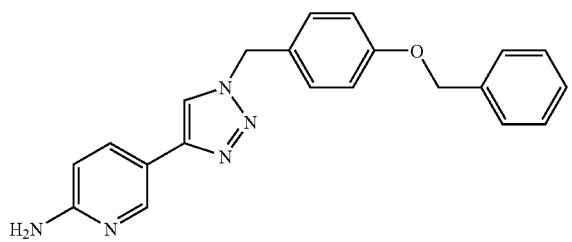

The titled compound (1.8 mg) was obtained from 5-ethynyl-pyridin-2-ylamine (10 mg) described in Manufacturing Example 3-3 and 1-benzyloxy-4-chloromethyl-benzene (22 mg) by the same method as in Example 1.

MS m/e (ESI) (MH$^+$) 358.21 (MH$^+$)

The starting substance 5-ethynyl-pyridin-2-ylamine was synthesized by the following method.

Manufacturing Example 3-1

2-Nitro-5-trimethylsilanylethynyl-pyridine

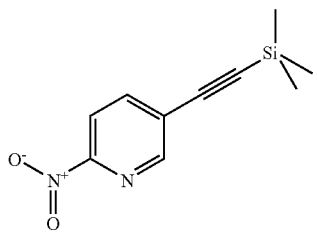

To a NMP solution (20 mL) of 5-bromo-2-nitropyridine (1.00 g, 4.93 mmol) were added trimethylsilyl acetylene (1.4 mL), tetrakis(triphenylphosphine)palladium(0) (110 mg), copper(I) iodide (38 mg), and N,N-diisopropylethylamine (1.7 mL) at room temperature, which was stirred under a nitrogen atmosphere for 4 hours at 65° C. Water was added at 0° C. to the reaction solution, which was then extracted with ethyl acetate. The organic layer was washed with water and saturated brine, dried over anhydrous magnesium sulfate, and filtered, after which the solvent was evaporated from the filtrate under a reduced pressure. The residue was purified by silica gel column chromatography (heptane:ethyl acetate=6:1) to obtain the titled compound (490 mg).

$^1$H-NMR spectrum (CDCl$_3$) δ (ppm): 0.30 (9H, s), 8.03-8.05 (1H, m), 8.22 (1H, J=8.4 Hz), 8.66 (1H, d, J=2.0 Hz).

Manufacturing Example 3-2

5-Trimethylsilanylethynyl-pyridin-2-ylamine

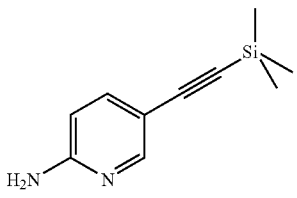

To a solution of THF (10 mL) and water (5 mL) of 2-nitro-5-trimethylsilanylethynyl-pyridine (410 mg) described in Manufacturing Example 3-1 were added iron powder (510 mg) and ammonium chloride (200 mg) at room temperature, which was stirred for 75 minutes at 70° C. The reaction solution was cooled to room temperature, and then filtered through Celite, and the solvent was evaporated from the filtrate under a reduced pressure. The residue was purified by silica gel column chromatography (heptane:ethyl acetate=1:1) to obtain the titled compound (320 mg).

$^1$H-NMR spectrum (CDCl$_3$) δ (ppm): 0.237 (9H, s), 4.73 (2H, brs), 6.44 (1H, d, J=8.6 Hz), 7.51 (1H, dd, J=2.2 Hz, 8.4 Hz), 8.19 (1H, d, J=2.2 Hz).

Manufacturing Example 3-3

5-Ethynyl-pyridin-2-ylamine

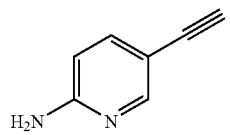

To a solution of THF (1 mL) and methanol (1 mL) of 5-trimethylsilanylethynyl-pyridin-2-ylamine (26 mg) described in Manufacturing Example 3-2 was added potassium carbonate (38 mg) at room temperature, which was stirred for 1 hour at room temperature. Water was added at 0° C. to the reaction solution, which was then extracted with ethyl acetate. The organic layer was washed with saturated brine, dried over anhydrous magnesium sulfate, and filtered, after which the solvent was evaporated from the filtrate under a reduced pressure. The residue was purified by NH silica gel column chromatography (heptane:ethyl acetate=1:1) to obtain the titled compound (16 mg).

$^1$H-NMR spectrum (CDCl$_3$) δ (ppm): 3.07 (1H, s), 4.73 (2H, brs), 6.46 (1H, d, J=8.6 Hz), 7.53 (1H, dd, J=2.2 Hz, 8.6 Hz), 8.21 (1H, s).

Example 4

3-(1-(4-Benzyloxy-benzyl)-1H-[1,2,3]triazol-4-yl)-pyridin-2,6-diamine

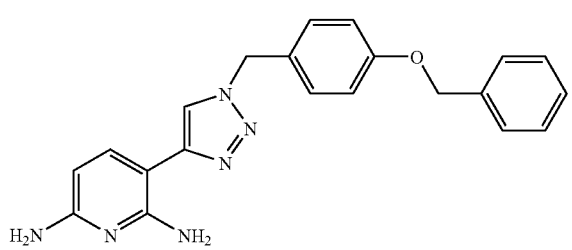

To a solution of NMP (200 μL) and water (200 μL) of 3-ethynyl-pyridin-2,6-diamine (20 mg) described in Manufacturing Example 4-3 were added 1-benzyloxy-4-chloromethyl-benzene (37 mg), sodium azide (15 mg), copper sulfate (4.8 mg), and copper (7.4 mg) at room temperature, and this mixture was irradiated for 30 seconds at no higher than 125° C. with 100 W microwaves. Aqueous sodium bicarbonate was added to the reaction mixture, which was extracted with ethyl acetate. The solvent was evaporated from the organic layer under a reduced pressure. The residue was purified by NH silica gel column chromatography (heptane:ethyl acetate=1:3, then with ethyl acetate) to obtain the titled compound (1.2 mg).

$^1$H-NMR spectrum (DMSO-d$_6$) δ (ppm): 5.09 (2H, s), 5.51 (2H, s), 5.66 (2H, s), 5.75 (1H, d, J=8.0 Hz), 6.47 (2H, s), 7.00-7.05 (2H, m), 7.30-7.48 (8H, m), 8.30 (1H, s).

Manufacturing Example 4-1

3-Iodo-pyridin-2,6-diamine

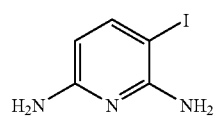

2,6-Diaminopyridine (100 g) was dissolved in DMSO (400 mL), and N-iodosuccinimide (100 g) was added thereto all at once under stirring at room temperature. The reaction solution was stirred for 10 minutes at room temperature, after which water (3.5 L) was added thereto and the precipitated solids were filtered off. The aqueous layer thus obtained was extracted with ethyl acetate (1.3 L) 3 times. The ethyl acetate layers were combined, and which was concentrated under a reduced pressure, and the residue thus obtained was purified by silica gel chromatography (heptane:ethyl acetate=2:3) to obtain the titled compound (24 g).

$^1$H-NMR spectrum (DMSO-d$_6$) δ (ppm): 5.41 (2H, brs), 5.57 (1H, d, J=8.0 Hz), 5.64 (2H, brs), 7.37 (1H, d, J=8.0 Hz).

Manufacturing Example 4-2

3-Trimethylsilanylethynyl-pyridin-2,6-diamine

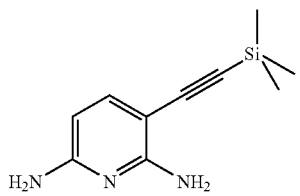

To a mixture of 3-iodo-pyridin-2,6-diamine (20 g) described in Manufacturing Example 4-1, trimethylsilyl acetylene (24 mL), copper(I) iodide (3.3 g), N,N-diisopropylethylamine (19 g), and NMP (290 mL) was added tetrakis(triphenylphosphine)palladium(0) (9.8 g), which was stirred for 30 minutes at room temperature under an argon atmosphere. Water was added to the reaction solution, which was then extracted with ethyl acetate. The ethyl acetate layer thus obtained was washed with water 4 times and dried over sodium sulfate. The sodium sulfate was filtered off, the solvent was evaporated under a reduced pressure, and the residue was purified by NH silica gel chromatography (heptane:ethyl acetate=4:1, then 1:1). The eluate was concentrated under a reduced pressure, and the resulting solids were washed with heptane containing a small amount of ethyl acetate to obtain the titled compound (11 g).

$^1$H-NMR spectrum (DMSO-d$_6$) δ (ppm): 0.20 (9H, s), 5.53 (2H, brs), 5.66 (1H, d, J=8.0 Hz), 5.95 (2H, brs), 7.11 (1H, d, J=8.0 Hz).

Manufacturing Example 4-3

3-Ethynyl-pyridin-2,6-diamine

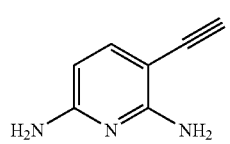

To a solution of THF (100 mL) of 3-trimethylsilanylethynyl-pyridin-2,6-diamine (7.0 g) described in Manufacturing Example 4-2 was added tetrabutylammonium fluoride (1M THF solution, 17 mL) under ice cooling, which was stirred for 10 minutes at room temperature. Water was added to the reaction solution, which was then extracted with ethyl acetate 3 times. The extract was dried over sodium sulfate, then concentrated under a reduced pressure, and the residue was purified by silica gel chromatography (ethyl acetate) to obtain the titled compound (3.4 g).

$^1$H-NMR spectrum (DMSO-d$_6$) δ (ppm): 4.08 (1H, s), 5.57 (2H, brs), 5.68 (1H, d, J=8.0 Hz), 5.89 (2H, brs), 7.14 (1H, d, J=8.0 Hz).

Example 5

3-(2-(4-Benzyloxy-benzyl)-2H-tetrazol-5-yl)-pyridin-2-ylamine

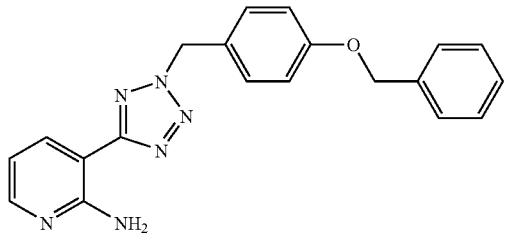

To a solution of 3-(2H-tetrazol-5-yl)-pyridin-2-ylamine (100 mg) described in Manufacturing Example 5-1, 4-benzyloxybenzyl chloride (172 mg), sodium iodide (111 mg), and DMF (3 mL) was added NaH (18 mg), which was stirred for 40 minutes at 60° C. Water was added to the reaction solution, which was then extracted with ethyl acetate. The organic layer was concentrated under a reduced pressure, and the residue was purified by NH silica gel column chromatography (hexane:ethyl acetate=4:1, then 2:1, then 1:1). Ethyl acetate was added to the resulting residue, and the solids were filtered off to obtain the titled compound (38 mg).

$^1$H-NMR spectrum (DMSO-d$_6$) δ (ppm): 5.11 (2H, s), 5.94 (2H, s), 6.71-6.76 (1H, m), 6.90 (2H, s), 7.04 (2H, d, J=8.8 Hz), 7.30-7.46 (7H, m), 8.13-8.16 (1H, m), 8.22-8.8.25 (1H, m).

The starting substance 3-(2H-tetrazol-5-yl)-pyridin-2-ylamine was synthesized by the following method.

Manufacturing Example 5-1

3-(2H-tetrazol-5-yl)-pyridin-2-ylamine

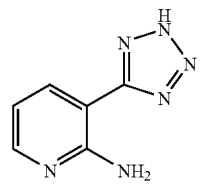

2-Amino-3-cyanopyridine (1.0 g), sodium azide (1.1 g), ammonium chloride (0.89 g), and DMF (15 mL) were stirred for 1.5 hours at 100° C. The reaction solution was directly purified by silica gel chromatography (ethyl acetate, then ethyl acetate:methanol:concentrated aqueous ammonia=6:2:0.5) to obtain the titled compound (0.66 g).

$^1$H-NMR spectrum (DMSO-d$_6$) δ (ppm): 6.70-6.77 (1H, m), 7.50 (2H, brs), 8.01-8.07 (1H, m), 8.20-8.26 (1H, m).

Example 6

3-(2-(4-Benzyloxy-benzyl)-2H-tetrazol-5-yl)-6-methoxymethyl-pyridin-2-ylamine

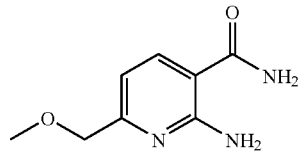

6-Methoxymethyl-3-(2H-tetrazol-5-yl)-pyridin-2-ylamine (50 mg) described in Manufacturing Example 6-3, 4-benzyloxybenzyl chloride (57 mg), sodium iodide (36 mg), NaH (9.7 mg/60% in oil), and DMF (3 mL) were stirred for 15 minutes at 60° C. Water was added to the reaction solution, which was then extracted with ethyl acetate. The organic layer was concentrated and purified by NH silica gel column chromatography (hexane:ethyl acetate=2:1). The residue thus obtained was solidified with ethyl acetate-hexane to obtain the titled compound (12 mg).

$^1$H-NMR spectrum (DMSO-d$_6$) δ (ppm): 3.36 (3H, s), 4.35 (2H, s), 5.10 (2H, s), 5.92 (2H, s), 6.76 (1H, d, J=8.0 Hz), 6.93 (2H, brs), 7.04 (2H, d, J=8.8 Hz), 7.30-7.45 (7H, m), 8.24 (1H, d, J=8.0 Hz).

The starting substance 6-methoxymethyl-3-(2H-tetrazol-5-yl)-pyridin-2-ylamine was synthesized by the following method.

Manufacturing Example 6-1

2-Amino-6-methoxymethyl-nicotinamide

2-Amino-6-methoxymethyl-nicotinic acid (0.50 g), WSC (1.1 g), HOBt (0.74 g), ammonium chloride (0.44 g), diisopropylethylamine (2.6 g), and DMSO (10 mL) were stirred for 29 hours at room temperature. Water was added thereto, and then the reaction solution was extracted with ethyl acetate. The organic layer was concentrated and purified by NH silica gel column chromatography (ethyl acetate). Ethyl acetate was added to the residue thus obtained, and the solids were filtered off to obtain the titled compound (290 mg).

¹H-NMR spectrum (DMSO-d₆) δ (ppm): 3.34 (3H, s), 4.28 (2H, s), 6.57 (1H, d, J=8.0 Hz), 7.22 (2H, brs), 7.25 (1H, brs), 7.89 (1H, brs), 7.94 (1H, d, J=8.0 Hz).

Manufacturing Example 6-2

2-Amino-6-methoxymethyl-nicotinonitrile

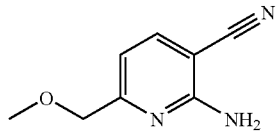

2-Amino-6-methoxymethyl-nicotinamide (90 mg) described in Manufacturing Example 6-1 and phosphorus oxychloride (3.0 g) were stirred for 0.5 hour at 100° C. The reaction solution was added to 0° C. dilute aqueous sodium hydroxide and then extracted with ethyl acetate. The organic layer was concentrated and the residue was purified with silica gel chromatography (ethyl acetate) to obtain the titled compound (40 mg).

¹H-NMR spectrum (DMSO-d₆) δ (ppm): 3.34 (3H, s), 4.31 (2H, s), 6.65 (1H, d, J=8.0 Hz), 6.89 (2H, brs), 7.86 (1H, d, J=8.0 Hz).

Manufacturing Example 6-3

6-Methoxymethyl-3-(2H-tetrazol-5-yl)-pyridin-2-ylamine

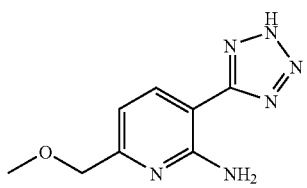

2-Amino-6-methoxymethyl-nicotinonitrile (0.20 g) described in Manufacturing Example 6-2, sodium azide (0.40 g), triethylamine hydrochloride (1.7 g), and NMP (25 mL) were stirred for 2 hours at 160° C. The reaction solution was directly purified by silica gel chromatography (ethyl acetate, then ethyl acetate:methanol:concentrated aqueous ammonia=6:2:1). The organic layer thus obtained was concentrated and purified by silica gel chromatography (ethyl acetate: methanol=4:1) to obtain the titled compound (170 mg).

¹H-NMR spectrum (DMSO-d₆) δ (ppm): 3.38 (3H, s), 4.38 (2H, s), 6.80 (1H, d, J=8.0 Hz), 7.38 (2H, brs), 8.17 (1H, d, J=8.0 Hz).

Example 7

3-(2-(4-Benzyloxy-benzyl)-2H-tetrazol-5-yl)-pyridin-2,6-diamine

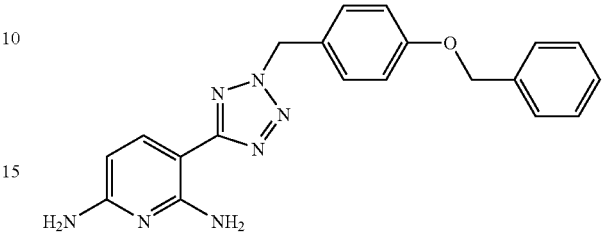

3-(2H-tetrazol-5-yl)-pyridin-2,6-diamine (60 mg) described in Manufacturing Example 7-3, 4-benzyloxybenzyl chloride (79 mg), sodium iodide (51 mg), NaH (14 mg, 60% in oil), and DMF (0.69 mL) were stirred for 10 minutes at 60° C. Water was added to the reaction solution, which was then extracted with ethyl acetate. The organic layer was concentrated and purified by NH silica gel column chromatography (hexane:ethyl acetate=2:1, then ethyl acetate). Ethyl acetate-hexane was added to the residue thus obtained, and the solids were filtered off to obtain the titled compound (26 mg).

¹H-NMR spectrum (DMSO-d₆) δ (ppm): 5.10 (2H, s), 5.83 (2H, s), 5.85 (1H, d, J=8.0 Hz), 6.07 (2H, brs), 6.47 (2H, brs), 7.02 (2H, d, J=8.4 Hz), 7.30-7.46 (7H, m), 7.84 (1H, d, J=8.0 Hz).

The starting substance 3-(2H-tetrazol-5-yl)-pyridin-2,6-diamine was synthesized by the following method.

Manufacturing Example 7-1

2,6-Diamino-nicotinamide

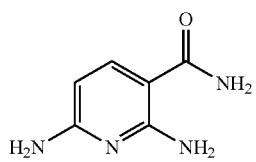

2,6-Diaminonicotinic acid (1.5 g), WSC (2.8 g), HOBt (2.0 g), ammonium chloride (1.6 g), diisopropylethylamine (7.6 g), and DMSO (45 mL) were stirred for 15 hours at room temperature. Water was added to the reaction solution, which was then extracted with ethyl acetate. The organic layer was concentrated and purified by silica gel chromatography (ethyl acetate, then ethyl acetate:methanol=4:1). The organic layer thus obtained was concentrated and purified by NH silica gel column chromatography (ethyl acetate). Ethyl acetate and hexane were added to the residue thus obtained, and the solids were filtered off to obtain the titled compound (1.1 g).

$^1$H-NMR spectrum (DMSO-d$_6$) δ (ppm): 5.64 (1H, d, J=8.0 Hz), 6.06 (2H, brs), 7.01 (2H, brs), 7.60 (1H, d, J=8.0 Hz).

Manufacturing Example 7-2

2,6-Diamino-nicotinonitrile

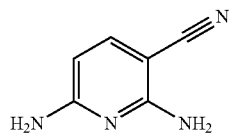

2,6-Diamino-nicotinamide (520 mg) described in Manufacturing Example 7-1 and phosphorus oxychloride (5.0 g) were stirred for 0.5 hour at 100° C. The reaction solution was added to 0° C. dilute aqueous sodium hydroxide, which was then extracted with ethyl acetate. The organic layer was concentrated and the residue was purified with NH silica gel column chromatography (ethyl acetate) to obtain the titled compound (340 mg).

$^1$H-NMR spectrum (DMSO-d$_6$) δ (ppm): 5.73 (1H, d, J=8.0 Hz), 6.20 (2H, brs), 6.48 (2H, brs), 7.32 (1H, d, J=8.0 Hz).

Manufacturing Example 7-3

3-(2H-tetrazol-5-yl)-pyridin-2,6-diamine

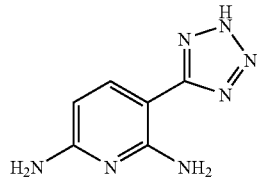

2,6-Diamino-nicotinonitrile (0.50 g) described in Manufacturing Example 7-2, sodium azide (1.2 g), triethylamine hydrochloride (5.1 g), and NMP (45 mL) were stirred for 11 hours at 160° C. The reaction solution was directly purified by silica gel chromatography (ethyl acetate, then ethyl acetate:methanol:concentrated aqueous ammonia=6:2:1). The organic layer thus obtained was concentrated and purified by silica gel chromatography (ethyl acetate, then ethyl acetate:methanol=4:1, then ethyl acetate:methanol:concentrated aqueous ammonia=6:2:1) to obtain the titled compound (270 mg).

$^1$H-NMR spectrum (DMSO-d$_6$) δ (ppm): 5.87 (1H, d, J=8.0 Hz), 6.28 (2H, brs), 6.94 (2H, brs), 7.75 (1H, d, J=8.0 Hz).

Example 8

3-(5-(4-Benzyloxy-benzyl)-[1,3,4]thiadiazol-2-yl))-pyridin-2-ylamine

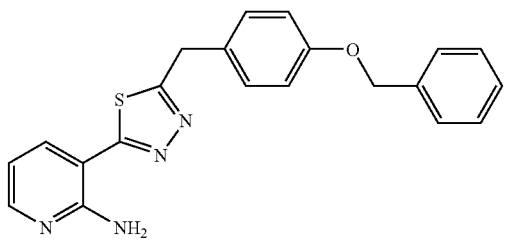

To a mixture of 2-amino-nicotinic acid N'-(2-(4-benzyloxy-phenyl)-acetyl)-hydrazide (30 mg) described in Manufacturing Example 8-2 and toluene (2 mL) was added Lawesson's reagent (65 mg) at room temperature, which was stirred for 90 minutes at 110° C. The reaction mixture was cooled to room temperature, and the solvent was evaporated under a reduced pressure. The residue was purified by NH silica gel column chromatography (heptane:ethyl acetate=1:2) to obtain the titled compound (19 mg).

$^1$H-NMR spectrum (DMSO-d$_6$) δ (ppm): 4.40 (2H, s), 5.07 (2H, s), 6.62-6.65 (1H, m), 6.99 (2H, d, J=8.2 Hz), 7.27-7.43 (7H, m), 7.52 (2H, brs), 7.82 (1H, dd, J=1.1 Hz, 7.7 Hz), 8.09-8.11 (1H, m).

The starting substance 2-amino-nicotinic acid N'-(2-(4-benzyloxy-phenyl)-acetyl)-hydrazide was synthesized by the following method.

Manufacturing Example 8-1

(4-Benzyloxy-phenyl)-acetic acid hydrazide

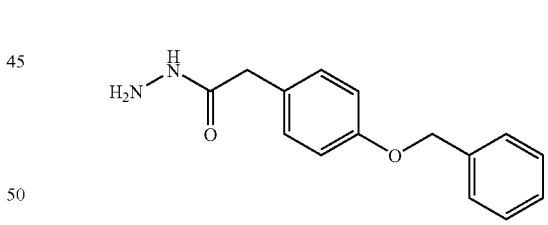

To a mixture of 4-benzyloxyphenylacetyl chloride (1.1 g) and THF (10 mL) were added triethylamine (1.8 mL) and hydrazine hydrate (0.20 mL) at room temperature, which was stirred at the same temperature for 7.5 hours. Water was added to the reaction solution, which was then extracted with ethyl acetate, and the organic layer was washed with saturated brine. The solvent was evaporated under a reduced pressure, after which the residue was purified by silica gel chromatography (methanol:ethyl acetate=1:30) to obtain the titled compound (0.23 g).

$^1$H-NMR spectrum (DMSO-d$_6$) δ (ppm): 3.24 (2H, s), 4.15 (2H, s), 5.05 (2H, s), 6.90 (2H, d, J=8.2 Hz), 7.14 (2H, d, J=8.2 Hz), 7.28-7.31 (1H, m), 7.34-7.42 (4H, m), 9.12 (1H, brs).

Manufacturing Example 8-2

2-Amino-nicotinic acid N'-(2-(4-benzyloxy-phenyl)-acetyl)-hydrazide

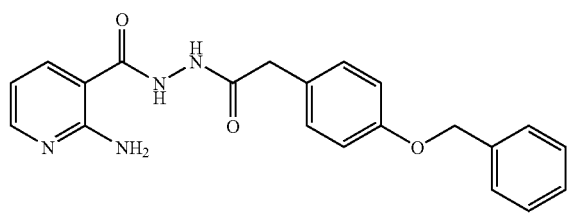

To a solution of DMSO (3 mL) of (4-benzyloxy-phenyl)-acetic acid hydrazide (130 mg) described in Manufacturing Example 8-1 were added triethylamine (0.21 mL), 2-aminonicotinic acid (70 mg), and BOP reagent (benzotriazol-1-yloxytris(dimethylamino)phosphonium hexafluorophosphate) (250 mg), which was stirred for 1 hour at the same temperature. Water was added to the reaction solution, and the solids thus precipitated were filtered off to obtain the titled compound (170 mg).

$^1$H-NMR spectrum (DMSO-$d_6$) δ (ppm): 3.43 (2H, s), 5.07 (2H, s), 6.56 (1H, dd, J=4.9, 7.6 Hz), 6.94 (2H, d, J=8.6 Hz), 7.00 (2H, s), 7.22 (2H, d, J=8.2 Hz), 7.28-7.43 (5H, m), 7.88 (1H, d, J=7.7 Hz), 8.08 (1H, d, J=4.6 Hz), 10.04 (1H, s), 10.21 (1H, brs).

Example 9

3-(5-(4-Benzyloxy-benzyl)-[1,3,4]oxadiazol-2-yl))-pyridin-2-ylamine

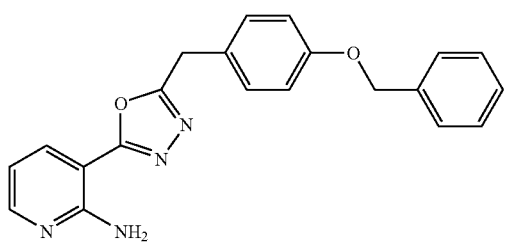

A mixture of 2-amino-nicotinic acid N'-(2-(4-benzyloxy-phenyl)-acetyl)-hydrazide (30 mg) described in Manufacturing Example 8-2, phosphorus pentoxide (68 mg), and toluene (1 mL) was refluxed for 1 hour. The reaction mixture was cooled to 0° C., water was added thereto at the same temperature, and then a 1N aqueous solution of sodium hydroxide was added dropwise thereto at the same temperature to neutralize the reaction mixture. Dichloromethane was added to the reaction mixture for extraction, and the organic layer was washed with saturated brine. The solvent was evaporated under a reduced pressure, after which the residue was purified by silica gel column chromatography (heptane:ethyl acetate=1:2) to obtain the titled compound (2.5 mg).

$^1$H-NMR spectrum (DMSO-$d_6$) δ (ppm): 4.21 (2H, s), 5.06 (2H, s), 6.57 (2H, brs), 6.69 (1H, dd, J=4.9, 7.7 Hz), 6.96 (2H, d, J=8.6 Hz), 7.27 (2H, d, J=8.6 Hz), 7.30-7.43 (5H, m), 7.94 (1H, dd, J=1.7 Hz, 7.8 Hz), 8.19-8.20 (1H, m).

Example 10

3-(5-(4-Benzyloxy-benzyl)-[1,3,4]thiadiazol-2-yl))-pyridin-2,6-diamine

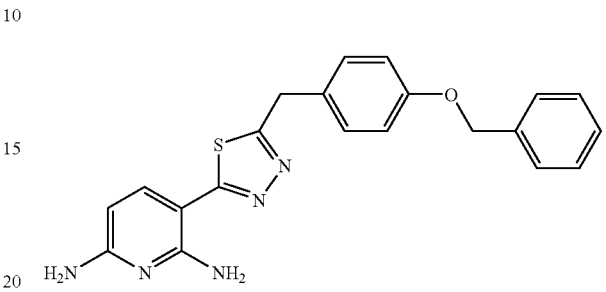

To a mixture of 2,6-diamino-nicotinic acid N'-(2-(4-benzyloxy-phenyl)-acetyl)-hydrazide (21 mg) described in Manufacturing Example 10-1 and toluene (1.6 mL) was added Lawesson's reagent (2,4-bis(4-methoxyphenyl)-1,3-dithia-2,4-diphosphetane-2,4-disulfide) (43 mg) at room temperature, which was stirred for 2 hours at 110° C. The reaction mixture was cooled to 0° C., water was added thereto at the same temperature, and the precipitates were filtered off. These solids were purified by reverse-phase high performance liquid chromatography (using an acetonitrile-water mobile phase containing 0.1% TFA), which was then filtered through an NH silica gel column to obtain the titled compound (1.2 mg).

MS m/e (ESI) (MH$^+$) 390.35 (MH$^+$)

The starting substance 2,6-diamino-nicotinic acid N'-(2-(4-benzyloxy-phenyl)-acetyl)-hydrazide was synthesized by the following method.

Manufacturing Example 10-1

2,6-Diamino-nicotinic acid N'-(2-(4-benzyloxy-phenyl)-acetyl)-hydrazide

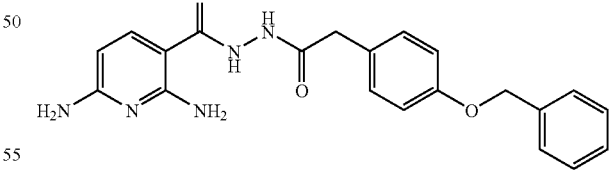

To a solution of DMF (1 mL) of (4-benzyloxy-phenyl)-acetic acid hydrazide (46 mg) described in Manufacturing Example 8-1 were added triethylamine (0.10 mL), 2,6-diamino-nicotinic acid (30 mg) described in Manufacturing Example 10-2-4, HOBt (27 mg), and WSC (41 mg), which was stirred overnight at the same temperature. Water was added to the reaction solution, and the precipitated solids were filtered off to obtain the titled compound (47 mg) as a crude form. This compound was used directly as a crude form in the subsequent reaction.

The starting substance 2,6-diamino-nicotinic acid was synthesized by the following method.

Manufacturing Example 10-2-1

4-Cyano-2-diaminomethylene-butyric acid ethyl ester

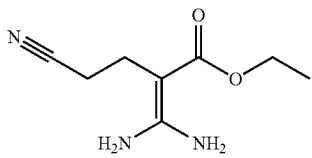

In an ammonia-ethanol solution (300 mL; prepared by saturating ammonia gas in ethanol at room temperature) was suspended (1-Ethoxyformimidoyl) 1-acetic acid ethyl ester hydrochloride (50 g), which was stirred for 4 hours at room temperature. The precipitated solids were filtered off, and the filtrate was concentrated under a reduced pressure until a quantity of the filtrate became approximately one-third. Hydrochloric acid-methanol (130 mL; containing 7.5% hydrochloric acid) was added to this reaction mixture, and the solvent was evaporated under a reduced pressure to obtain 3,3-diamino-acrylic acid ethyl ester hydrochloride (40 g).

To a mixture of the resulting 3,3-diamino-acrylic acid ethyl ester hydrochloride (2.2 g) and THF (40 mL) were added triethylamine (2.0 mL) and acrylonitrile (1.2 mL) at room temperature, which was refluxed for 6 hours. The reaction mixture was cooled to room temperature, the triethylamine hydrochloride thus produced was filtered off, and the filtrate was evaporated under a reduced pressure to obtain the titled compound (0.60 g).

$^1$H-NMR spectrum (CDCl$_3$) δ (ppm): 1.26 (3H, t, J=7.2 Hz), 2.42-2.49 (2H, m), 2.50-2.57 (2H, m), 4.12 (2H, q, J=7.2 Hz), 4.22 (2H, brs), 6.45 (2H, brs).

Manufacturing Example 10-2-2

2,6-Diamino-4,5-dihydro-pyridin-3-carboxylic acid ethyl ester

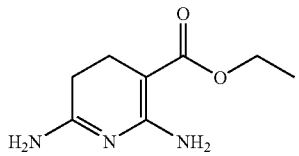

To a suspension of THF (7 mL) and NaH (210 mg/60% in oil) was added dropwise a solution of THF (7 mL) and 4-cyano-2-diaminomethylene-butyric acid ethyl ester (0.55 g) described in Manufacturing Example 10-2-1, which was refluxed for 19 hours and 20 minutes. The reaction solution was poured into ice water and then extracted with ethyl acetate. The organic layer was dried over anhydrous magnesium sulfate, after which the solvent was evaporated under a reduced pressure to obtain the crude titled compound (0.19 g).

$^1$H-NMR spectrum (CDCl$_3$) δ (ppm): 1.27 (3H, t, J=7.2 Hz), 2.28-2.34 (2H, m), 2.46-2.52 (2H, m), 4.14 (2H, q, J=7.2 Hz).

Manufacturing Example 10-2-3

2,6-Diamino-nicotinic acid ethyl ester

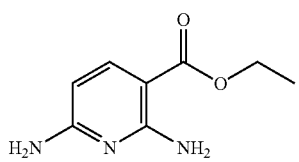

To a solution of THF (300 mL) and 2,6-diamino-4,5-dihydro-pyridin-3-carboxylic acid ethyl ester (4.5 g) described in Manufacturing Example 10-2-2 was added 2,3-dichloro-5,6-dicyano-1,4-benzoquinone (5.6 g), which was stirred for 40 minutes at room temperature. The solvent was evaporated under a reduced pressure, and the residue was purified by NH silica gel column chromatography (ethyl acetate), after which it was washed with hexane to obtain the titled compound (3.1 g).

$^1$H-NMR spectrum (CDCl$_3$) δ (ppm): 1.35 (3H, t, J=7.2 Hz), 4.27 (2H, q, J=7.2 Hz), 4.60 (2H, brs), 5.82 (1H, d, J=8.4 Hz), 7.90 (1H, d, J=8.4 Hz).

Manufacturing Example 10-2-4

2,6-Diamino-nicotinic acid

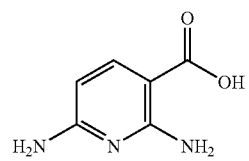

2,6-Diamino-nicotinic acid ethyl ester (2.0 g) described in Manufacturing Example 10-2-3 was dissolved in ethanol (15 mL), and a 1N aqueous solution of sodium hydroxide (15 mL) was added thereto, after which the solution was refluxed for 2 hours. The reaction mixture was cooled to room temperature, and the ethanol solvent was evaporated under a reduced pressure. The reaction mixture was neutralized with 1N hydrochloric acid at 0° C. The precipitated solids were filtered off to obtain the titled compound (1.7 g).

$^1$H-NMR spectrum (DMSO-d$_6$) δ (ppm): 5.70 (1H, d, J=8.4 Hz), 6.31 (2H, brs), 6.58-7.12 (1H, brs), 7.62 (1H, d, J=8.4 Hz).

Example 11

3-(5-(4-Benzyloxy-benzyl)-[1,3,4]oxadiazol-2-yl))-6-methoxymethyl-pyridin-2-ylamine

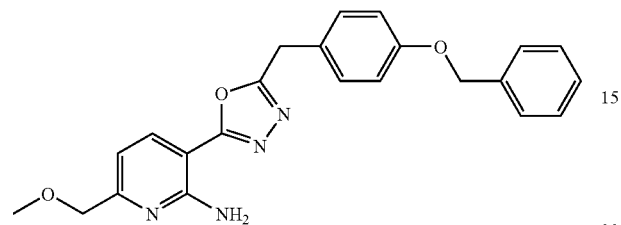

A mixture of 2-amino-6-methoxymethyl-nicotinic acid N'-(2-(4-benzyloxy-phenyl)-acetyl)-hydrazide (30 mg) described in Manufacturing Example 11-5, phosphorus pentoxide (68 mg), and toluene (1 mL) was stirred for 1 hour at 90° C., and then stirred for another 3 hours at 100° C. The reaction mixture was cooled to 0° C., water, ethyl acetate, and THF were added at the same temperature, and the mixture was filtered. The organic layer of the filtrate was washed with saturated brine. The solvent was evaporated under a reduced pressure, after which the residue was purified by reverse-phase high performance liquid chromatography (using an acetonitrile-water mobile phase containing 0.1% TFA) to obtain TFA salt (0.57 mg) of the titled compound.

MS m/e (ESI) (MH$^+$) 403.29 (MH$^+$)

The starting substance 2-amino-6-methoxymethyl-nicotinic acid N'-(2-(4-benzyloxy-phenyl)-acetyl)-hydrazide was synthesized by the following method.

Manufacturing Example 11-1

2-Amino-6-chloro-nicotinic acid

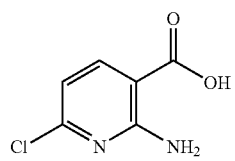

To a mixture of 2,6-dichloronicotinic acid (36 g), acetamide (80 g), potassium carbonate (78 g), copper(I) chloride (0.93 g), and xylene (80 mL) was added tris(2-(2-methoxyethoxy)ethyl)amine (3.0 mL), which was stirred overnight at 145° C. The reaction mixture was cooled to room temperature, after which copper(I) chloride (0.46 g) was added to the reaction mixture at the same temperature, and then stirred overnight at 145° C. The reaction mixture was cooled to 105° C., after which water (100 mL) was added at the same temperature, and then stirred for 1 hour at the same temperature. The reaction mixture was cooled to room temperature, 5N hydrochloric acid (150 mL) was added thereto at the same temperature, and then the reaction mixture was neutralized with an aqueous citric acid solution. Ethyl acetate was added to the reaction mixture, which was filtered through Celite. The organic layer was washed with saturated brine, after which the solvent was evaporated under a reduced pressure. The residue was purified by silica gel column chromatography (ethyl acetate), after which recrystallization was performed from an ethyl acetate-hexane system to obtain the titled compound (1.4 g).

$^1$H-NMR spectrum (DMSO-d$_6$) δ (ppm): 6.61 (1H, d, J=8.1 Hz), 7.53 (2H, brs), 8.01 (1H, d, J=8.1 Hz).

Manufacturing Example 11-2

2-Amino-6-chloro-nicotinic acid methyl ester

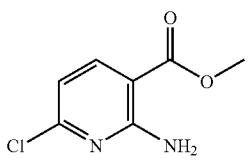

To methanol (50 mL) were added concentrated sulfuric acid (25 mL) and 2-amino-6-chloro-nicotinic acid (4.3 g) described in Manufacturing Example 11-1 under ice cooling, which was stirred for 5 hours at 70° C. The reaction mixture was cooled to room temperature and then neutralized by adding an aqueous solution of sodium hydrogencarbonate (90 g) at the same temperature. The solids thus produced were filtered off to obtain the titled compound (3.2 g).

$^1$H-NMR spectrum (CDCl$_3$) δ (ppm): 3.88 (3H, s), 6.62 (1H, d, J=8.2 Hz), 8.05 (1H, d, J=8.1 Hz).

Manufacturing Example 11-3

2-Amino-6-methoxymethyl-nicotinic acid methyl ester

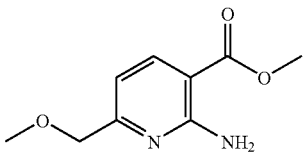

A mixture of 2-amino-6-chloro-nicotinic acid methyl ester (1.4 g) described in Manufacturing Example 11-2, tributyl-methoxymethyl-tin (3.1 g) described in Manufacturing Example 11-3-1, tetrakis(triphenylphosphine)palladium(0) (440 mg), and NMP (20 mL) was stirred for 3.5 hours at 130° C. The reaction solution was allowed to cool, an aqueous potassium fluoride solution and ethyl acetate were added thereto under ice cooling, after which the reaction mixture was filtered through Celite. The organic layer was washed with saturated brine, after which the solvent was evaporated under a reduced pressure. The residue was purified by silica gel column chromatography (heptane:ethyl acetate=2:1) to obtain the titled compound (0.93 g).

¹H-NMR spectrum (CDCl₃) δ (ppm): 3.47 (3H, s), 3.88 (3H, s), 4.41 (2H, s), 6.74 (1H, d, J=7.9 Hz), 8.14 (1H, d, J=7.9 Hz).

Manufacturing Example 11-3-1

Tributyl-methoxymethyl-tin

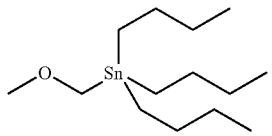

To a mixture of diisopropylamine (9.4 mL) and THF (150 mL) was added n-butyl lithium (2.4M n-hexane solution, 25 mL) by drops at −78° C., which was stirred for 30 minutes at the same temperature. Tributyltin hydride (16 mL) was added dropwise to the reaction mixture at the same temperature, after which the reaction mixture was stirred for 30 minutes under ice cooling. The reaction solution was cooled to −78° C., then chloromethyl methyl ether (4.6 mL) was added dropwise thereto, and then which was gradually warmed to room temperature. Water (100 mL) and diethyl ether (300 mL) were added to the reaction solution, and the organic layer was washed with saturated brine, after which the solvent was evaporated under a reduced pressure. The residue was purified by silica gel column chromatography (heptane:ethyl acetate=30:1) to obtain the titled compound (18 g).

¹H-NMR spectrum (CDCl₃) δ (ppm): 0.88-0.93 (15H, m), 1.26-1.35 (6H, m), 1.47-1.55 (6H, m), 3.30 (3H, s), 3.71 (2H, t, J=6.8 Hz).

Manufacturing Example 11-4

2-Amino-6-methoxymethyl-nicotinic acid

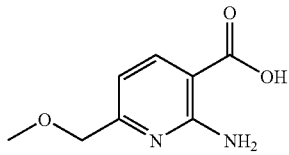

To a mixture of 2-amino-6-methoxymethyl-nicotinic acid methyl ester (2.9 g) described in Manufacturing Example 11-3, THF (30 mL), methanol (7.5 mL), and water (7.5 mL) was added lithium hydroxide monohydrate (1.2 g), which was stirred overnight at room temperature. Acetic acid (1.7 mL of) was added to the reaction mixture at the same temperature, and the solvent was evaporated under a reduced pressure. The residue was filtered through silica gel (methanol:ethyl acetate=1:3) and the solvent was evaporated under a reduced pressure, after which the residue was washed with water to obtain the titled compound (2.1 g).

¹H-NMR spectrum (DMSO-d₆) δ (ppm): 3.32 (3H, s), 4.29 (2H, s), 6.61 (1H, d, J=7.9 Hz), 7.16 (2H, brs), 8.02 (1H, d, J=7.9 Hz).

Manufacturing Example 11-5

2-Amino-6-methoxymethyl-nicotinic acid N'-(2-(4-benzyloxy-phenyl)-acetyl)-hydrazide

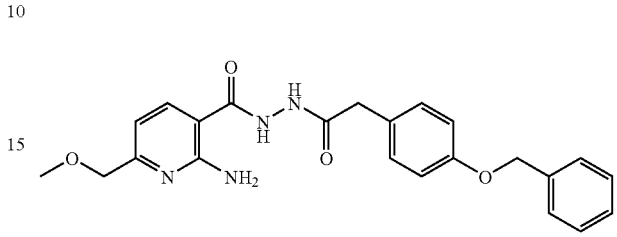

The titled compound (57 mg) was obtained from 2-amino-6-methoxymethyl-nicotinic acid (33 mg) described in Manufacturing Example 11-4 and (4-benzyloxy-phenyl)-acetic acid hydrazide (46 mg) described in Manufacturing Example 8-1, by the same method as in Manufacturing Example 8-2.

¹H-NMR spectrum (DMSO-d₆) δ (ppm): 3.32 (3H, s), 3.43 (2H, s), 4.28 (2H, s), 5.07 (2H, s), 6.59 (1H, d, J=7.9 Hz), 6.94 (2H, d, J=8.6 Hz), 7.06 (2H, brs), 7.22 (2H, d, J=8.4 Hz), 7.28-7.32 (1H, m), 7.35-7.43 (4H, m), 7.92 (1H, d, J=7.9 Hz), 10.03 (1H, brs), 10.19 (1H, brs).

Example 12

3-(4-(4-Benzyloxy-benzyl)-[1,2,3]triazol-1-yl)-pyridin-2-ylamine

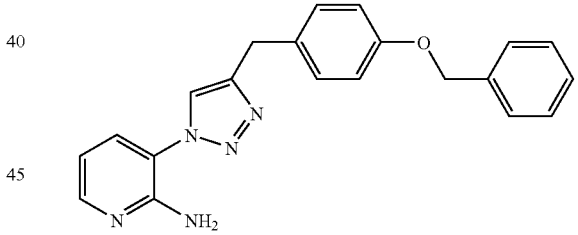

To a solution of DMSO (5.0 mL), water (1.0 mL) and 1-benzyloxy-4-prop-2-ynyl-benzene (50 mg) described in Manufacturing Example 12-2 were added sodium azide (16 mg), 3-iodopyridin-2-ylamine (50 mg) described in Manufacturing Example 1-2, copper(I) iodide (4.3 mg), (1S,2S)—N,N'-dimethylcyclohexane-1,2-diamine (CAS No. 87583-89-9; 4.8 mg), and sodium ascorbate (4.5 mg), which was stirred for 3 hours at 60° C., and then, which was stirred for 2 days at room temperature. Water and ethyl acetate were added to the reaction mixture, and the organic layer was extracted. The organic layer was washed with water and saturated brine, dried over anhydrous magnesium sulfate and filtered, and then the filtrate was evaporated under a reduced pressure. The residue was purified by NH silica gel column chromatography (ethyl acetate:heptane=2:1) to obtain the titled compound (6.7 mg).

¹H-NMR spectrum (DMSO-d₆) δ (ppm): 4.01 (2H, s), 5.08 (2H, s), 6.30 (2H, s), 6.70-6.74 (1H, m), 6.94-6.96 (2H, m), 7.23-7.25 (2H, m), 7.32-7.45 (5H, m), 7.64-7.66 (1H, m), 8.09-8.10 (1H, m), 8.23 (1H, s).

The starting substance 1-benzyloxy-4-prop-2-ynyl-benzene was synthesized by the following method.

Manufacturing Example 12-1

(3-(4-Benzyloxy-phenyl)-prop-1-ynyl)-trimethyl-silane

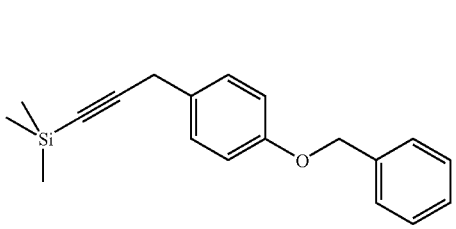

To a solution of THF (20 mL) and trimethylsilylacetylene (850 μL) was added ethyl magnesium bromide (3M diethyl ether solution, 1.9 mL) at room temperature under a nitrogen atmosphere, which was stirred for 40 minutes at 65° C. The reaction solution was cooled to room temperature, after which copper(I) bromide (310 mg) and 4-benzyloxybenzyl chloride (81.0 g) were added to the reaction solution, which was stirred for 8 hours and 45 minutes at 65° C. A saturated aqueous ammonia chloride solution was added at room temperature to the reaction solution, which was then extracted with ethyl acetate. The organic layer was washed with saturated brine and dried over anhydrous magnesium sulfate, and then the solvent was evaporated under a reduced pressure. The residue was purified by NH silica gel column chromatography (heptane:ethyl acetate=30:1) to obtain the titled compound (910 mg).

$^1$H-NMR spectrum (CDCl$_3$) δ (ppm): 0.18 (9H, s), 3.59 (2H, s), 5.06 (2H, s), 6.92-6.95 (2H, m), 7.23-7.26 (2H, m), 7.30-7.34 (1H, m), 7.36-7.40 (2H, m), 7.42-7.44 (2H, m).

Manufacturing Example 12-2

1-Benzyloxy-4-prop-2-ynyl-benzene

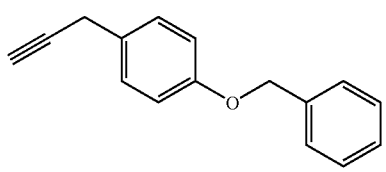

To a solution of methanol (20 mL) of (3-(4-benzyloxy-phenyl)-prop-1-ynyl)-trimethyl-silane (910 mg) described in Manufacturing Example 12-1 was added potassium carbonate (850 mg) at room temperature, which was stirred for 4 hours and 10 minutes at room temperature. Water was added to the reaction solution, which was then extracted with ethyl acetate. The organic layer was washed with saturated brine and dried over anhydrous magnesium sulfate, and then the solvent was evaporated under a reduced pressure. The residue was purified by silica gel column chromatography (heptane:ethyl acetate=20:1) to obtain the titled compound (620 mg).

$^1$H-NMR spectrum (CDCl$_3$) δ (ppm): 2.16 (1H, t, J=2.4 Hz), 3.54 (2H, d, J=2.4 Hz), 5.05 (2H, s), 6.91-6.94 (2H, m), 7.24-7.26 (2H, m), 7.29-7.43 (5H, m).

Example 13

3-(5-(4-Benzyloxy-benzyl)-[1,2,4]-oxadiazol-3-yl)-pyridin-2-ylamine

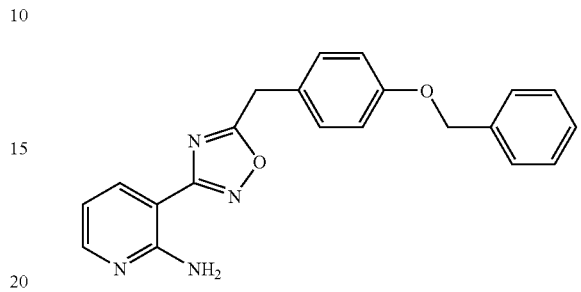

To a solution of dichloromethane (5 mL) of (4-benzyloxy-phenyl)-acetic acid (220 mg) was added N,N'-dicyclohexyl-carbodiimide (95 mg) at 0° C., which was stirred for 2 hours and 20 minutes at 0° C. The reaction mixture was filtered through Celite, and the solvent was evaporated from the filtrate under a reduced pressure. Pyridine (5 mL) and 2-amino-N-hydroxy-nicotinamidine (70 mg) described in Manufacturing Example 13-1 were added to the residue, which was stirred for 4 hours and 10 minutes under heating and reflux. The reaction mixture was cooled to room temperature, after which the solvent was evaporated under a reduced pressure. Water was added to the residue, which was extracted with ethyl acetate, and then the organic layer was washed with water and saturated brine. The organic layer was dried over anhydrous magnesium sulfate and filtered, after which the filtrate was evaporated under a reduced pressure. The residue was purified by NH silica gel column chromatography (heptane:ethyl acetate=1:1) to obtain the titled compound (85 mg).

$^1$H-NMR spectrum (DMSO-d$_6$) δ (ppm): 4.35 (2H, s), 5.08 (2H, s), 6.70-6.73 (1H, m), 6.84 (2H, s), 6.99 (2H, d, J=8.1 Hz), 7.29-7.31 (3H, m), 7.35-7.39 (2H, m), 7.41-7.43 (2H, m), 8.14-8.16 (2H, m).

The starting substance 2-amino-N-hydroxy-nicotinamidine was synthesized by the following method.

Manufacturing Example 13-1

2-Amino-N-hydroxy-nicotinamidine

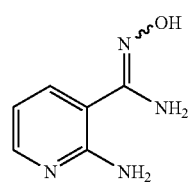

To a solution of ethanol (10 mL) and 2-amino-nicotinonitrile (590 mg) were added hydroxylamine hydrochloride (510 mg) and potassium carbonate (1.4 g) at room temperature, which was stirred for 7 hours and 30 minutes under reflux. After this, the reaction mixture was stirred for 13 hours and 30 minutes at room temperature, then water was added to the reaction mixture, which was extracted with ethyl acetate. The organic layer was dried over anhydrous magnesium sulfate and filtered, after which the filtrate was evaporated under a reduced pressure. The residue was purified by silica gel column chromatography (ethyl acetate:methanol=10:1) to obtain the titled compound (520 mg) as a cis-trans mixture. The titled compound was used in the subsequent reaction without further purification.

Example 14

3-(1-(4-Benzyloxy-benzyl)-1H-[1,2,4]triazol-3-yl)-pyridin-2-ylamine

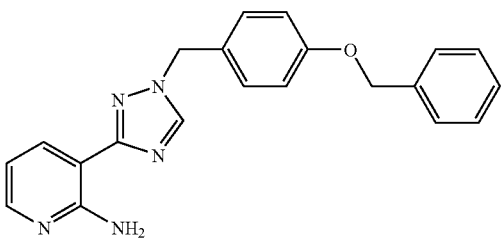

3-(1H-[1,2,4]triazol-3-yl)-pyridin-2-ylamine (20 mg) described in Manufacturing Example 14-3, 4-benzyloxybenzyl chloride (32 mg), potassium carbonate (86 mg, and DMF (3.0 mL) were stirred for 0.5 hour at 60° C. Water was added to the reaction solution, which was extracted with ethyl acetate. The organic layer was concentrated and purified by NH silica gel column chromatography (heptane:ethyl acetate=2:1, then 1:1) to obtain the titled compound (27 mg).

$^1$H-NMR spectrum (DMSO-d$_6$) δ (ppm): 5.09 (2H, s), 5.40 (2H, s), 6.64 (1H, dd, J=4.8 Hz, 8.0 Hz), 6.99 (2H, brs), 7.01 (2H, dd, J=2.0 Hz, 6.4 Hz), 7.30-7.46 (7H, m), 8.01 (1H, dd, J=2.0 Hz, 4.8 Hz), 8.18 (1H, dd, J=2.0 Hz, 8.0 Hz), 8.75 (1H, s).

The starting substance 3-(1H-[1,2,4]triazol-3-yl)-pyridin-2-ylamine was synthesized by the following method.

Manufacturing Example 14-1

2-Amino-nicotinamide

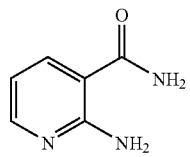

2-Aminonicotinic acid (5.0 g), WSC (10 g), HOBt (7.3 g), ammonium chloride (5.8 g), diisopropylethylamine (28 g), and DMSO (100 mL) were stirred for 16 hours at room temperature. Water was added and then extraction was performed with ethyl acetate and THF. The organic layer was concentrated and purified by silica gel chromatography (ethyl acetate) to obtain the titled compound (2.6 g).

$^1$H-NMR spectrum (DMSO-d$_6$) δ (ppm): 6.53-6.58 (1H, m), 7.17 (2H, brs), 7.29 (1H, brs), 7.92 (1H, brs), 7.92 (1H, dd, J=2.0 Hz, 8.0 Hz), 8.06 (1H, dd, J=2.0 Hz, 4.8 Hz).

Manufacturing Example 14-2

2-Amino-thionicotinamide

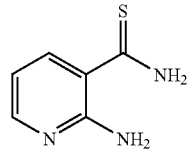

2-Amino-nicotinamide (1.6 g) described in Manufacturing Example 14-1, hexamethyldisiloxane (3.2 g), phosphorus pentasulfide (950 mg), and hexamethylphosphoramide (13 mL) were stirred for 18 hours at 110° C. The reaction solution was passed through a glass filter (eluted with ethyl acetate) lined with NH-silica gel and silica gel in a 1:1 ratio. The eluate was purified by NH silica gel column chromatography (heptane:ethyl acetate=1:1) to obtain the titled compound (290 mg).

$^1$H-NMR spectrum (DMSO-d$_6$) δ (ppm): 6.62-6.66 (1H, m), 6.86 (2H, brs), 7.85 (1H, dd, J=2.0 Hz, 8.0 Hz), 8.20 (1H, dd, J=2.0 Hz, 4.8 Hz).

Manufacturing Example 14-3

3-(1H-[1,2,4]triazol-3-yl)-pyridin-2-ylamine

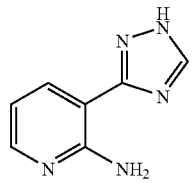

2-Amino-thionicotinamide (240 mg) described in Manufacturing Example 14-2 and formic acid hydrazide (2.0 g) were stirred for 3 hours at 150° C. Water was added and then extraction was performed with ethyl acetate. The organic layer was concentrated and purified by silica gel chromatography (ethyl acetate, then ethyl acetate:methanol=20:1) to obtain the titled compound (100 mg).

$^1$H-NMR spectrum (DMSO-d$_6$) δ (ppm): 6.68 (1H, dd, J=4.8 Hz, 8.0 Hz), 8.05 (1H, dd, J=2.0 Hz, 4.8 Hz), 8.20 (1H, d, J=8.0 Hz), 8.56 (2H, brs).

Example 15

3-(5-(4-Benzyloxy-benzyl)-4H-[1,2,4]triazol-3-yl)-pyridin-2-ylamine

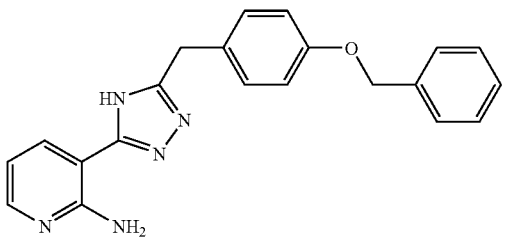

To a methanol (10 mL) solution of 4-benzyloxy-phenylacetic acid hydrazide (200 mg) described in Manufacturing Example 15-1 were added 2-amino-3-cyanopyridine (92 mg) and 28% sodium methoxide-methanol solution (30 mg), which was stirred for 14 hours under heating and reflux. Water and ethyl acetate were added to the reaction solution, and then the organic layer was extracted. The organic layer was washed with water and saturated brine, then dried over anhydrous magnesium sulfate and filtered, after which the filtrate was evaporated under a reduced pressure. The residue was purified by silica gel column chromatography (ethyl acetate:heptane=1:5) to obtain the titled compound (3 mg).

MS m/e (ESI) (MH$^+$) 358.22 (MH$^+$)

$^1$H-NMR spectrum (DMSO-d$_6$) δ (ppm): 4.05 (2H, s), 5.07 (2H, s), 6.15-6.65 (1H, m), 6.96 (2H, d, J=8.0 Hz), 7.11 (2H, brs), 7.23 (2H, d, J=8.4 Hz), 7.31-7.44 (5H, m), 8.00-8.01 (1H, m), 8.13-8.1 (1H, m).

The starting substance 4-benzyloxy-phenylacetic acid hydrazide was synthesized by the following method.

Manufacturing Example 15-1

4-Benzyloxy-phenylacetic acid hydrazide

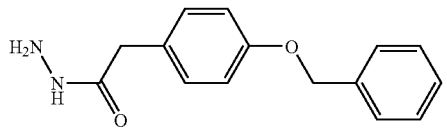

To a solution of THF (50 mL) of 4-benzyloxy-phenylacetic acid (7.0 g) were added hydrazine monohydrate (4.3 g), WSC (6.7 g), HOBt (4.7 g), and triethylamine (3.5 g), which was stirred for 15 hours at room temperature. Water was added to the reaction mixture, and the precipitated solids were filtered off to obtain the titled compound (1.2 g).

$^1$H-NMR spectrum (DMSO-d$_6$) δ (ppm): 3.26 (2H, s), 4.20 (2H, s), 5.06 (2H, s), 6.91-6.94 (2H, m), 7.12-7.20 (2H, m), 7.30-7.42 (5H, m), 9.15 (1H, s).

Example 16

3-(1-(4-(5-Chloro-furan-2-ylmethyl)-benzene)-1H-[1,2,3]triazol-4-yl)-pyridin-2-ylamine

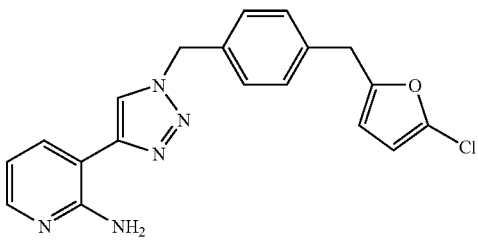

The titled compound (30 mg) was obtained from 3-ethynyl-pyridin-2-ylamine (30 mg) described in Manufacturing Example 1-2 and 2-chloro-5-(4-chloromethyl-benzyl)-furan (67 mg) described in Manufacturing Example 16-4, by the same method as in Example 1.

$^1$H-NMR spectrum (DMSO-d$_6$) δ (ppm): 3.95 (2H, s), 5.64 (2H, s), 6.24 (1H, d, J=3.2 Hz), 6.34 (1H, d, J=3.2 Hz), 6.62 (1H, dd, J=4.8 Hz, 7.5 Hz), 6.88 (2H, s), 7.25 (2H, d, J=8.1 Hz), 7.32 (2H, d, J=8.1 Hz), 7.83 (1H, dd, J=1.8 Hz, 7.5 Hz), 7.95 (1H, dd, J=1.8 Hz, 4.8 Hz), 8.70 (1H, s).

The starting substance 2-chloro-5-(4-chloromethyl-benzyl)-furan was synthesized by the following method.

Manufacturing Example 16-1

4-((5-Chloro-furan-2-yl)-hydroxy-methyl)-benzonitrile

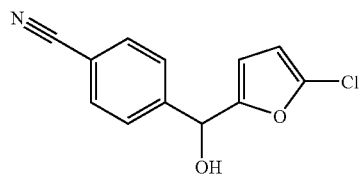

To a solution of THF (40 mL) and 4-iodobenzonitrile (2.0 g) was added isopropylmagnesium chloride (2M, 6.1 mL) dropwise at −78° C. under a nitrogen atmosphere, which was stirred for 1 hour and 10 minutes at 0° C. After cooling to 78° C., 5-chloro-2-furaldehyde (1.4 g) was added dropwise thereto, which was stirred for 15 minutes at room temperature. A saturated aqueous ammonium chloride solution was added at room temperature, and then extraction was performed with ethyl acetate. The organic layer was washed with saturated brine, dried over anhydrous magnesium sulfate, and filtered, after which the filtrate was evaporated under a reduced pressure. The residue was purified by silica gel column chromatography (heptane:ethyl acetate=1:1) to obtain the titled compound (2.4 g).

$^1$H-NMR spectrum (DMSO-d$_6$) δ (ppm): 5.78 (1H, d, J=4.9 Hz), 6.28 (1H, d, J=3.3 Hz), 6.37 (1H, d, J=4.9 Hz), 6.39 (1H, d, J=3.3 Hz), 7.59 (2H, d, J=8.4 Hz), 7.84 (2H, d, J=8.4 Hz).

Manufacturing Example 16-2

4-(5-Chloro-furan-2-ylmethyl)-benzylamine

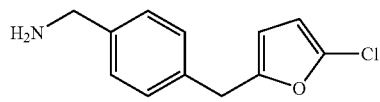

To a suspension of THF (40 mL) and LAH (2.4 g) was added aluminum chloride (9.7 g) at 0° C., which was stirred until the aluminum chloride dissolved. 4-((5-Chloro-furan-2-yl)-hydroxy-methyl)-benzonitrile (2.4 g) described in Manufacturing Example 16-1 was then added thereto at 0° C., which was stirred for 4 hours and 30 minutes at room temperature. An aqueous ammonia solution was added at 0° C. to the reaction suspension, which was filtered through Celite, and the solvent was evaporated from the filtrate under a reduced pressure. The residue was purified by NH silica gel column chromatography (heptane:ethyl acetate=1:2) to obtain the titled compound (1.6 g).

$^1$H-NMR spectrum (DMSO-$d_6$) δ (ppm): 1.80 (2H, brs), 3.66 (2H, s), 3.90 (2H, s), 6.20 (1H, d, J=3.2 Hz), 6.33 (1H, d, J=3.2 Hz), 7.14 (2H, d, J=7.6 Hz), 7.25 (2H, d, J=8.0 Hz).

Manufacturing Example 16-3

4-(5-Chloro-furan-2-ylmethyl)-phenyl)-methanol

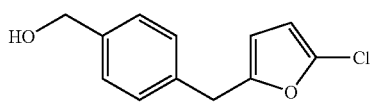

To a solution of acetic acid (10 mL), water (10 mL) and 4-(5-chloro-furan-2-ylmethyl)-benzylamine (1.5 g) described in Manufacturing Example 16-2 was added sodium nitrite (4.6 g) at 0° C., which was stirred for 35 minutes at room temperature. A 5N aqueous sodium hydroxide solution was added at room temperature to the reaction mixture, which was extracted with ethyl acetate. The organic layer was washed with saturated brine, then dried over anhydrous magnesium sulfate and filtered, after which the filtrate was evaporated under a reduced pressure. Next, a 5N aqueous sodium hydroxide solution (5 mL) was added to a solution of ethanol (10 mL), THF (10 mL) and the residue at 0° C., which was stirred for 20 minutes at room temperature. The reaction mixture was extracted with ethyl acetate, then the organic layer was washed with saturated brine. The organic layer was dried over anhydrous magnesium sulfate and filtered, after which the filtrate was evaporated under a reduced pressure. The residue was purified by NH silica gel column chromatography (heptane:ethyl acetate=2:1) to obtain the titled compound (1.2 g).

$^1$H-NMR spectrum (DMSO-$d_6$) δ (ppm): 3.91 (2H, s), 4.44 (2H, d, J=5.7 Hz), 5.11 (H, t, J=5.7 Hz), 6.20 (1H, d, J=3.3 Hz), 6.33 (1H, d, J=3.1 Hz), 7.16 (2H, d, J=8.1 Hz), 7.24 (2H, d, J=7.9 Hz).

Manufacturing Example 16-4

2-Chloro-5-(4-chloromethyl-benzyl)-furan

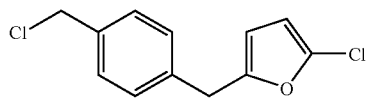

To a solution of carbon tetrachloride (10 mL) and 4-(5-chloro-furan-2-ylmethyl)-phenyl)-methanol (500 mg) described in Manufacturing Example 16-3 was added triphenylphosphine (767 mg) at room temperature, which was stirred for 19 hours and 25 minutes under reflux. The solvent was evaporated from the reaction mixture under a reduced pressure, and the residue was purified by silica gel column chromatography (heptane:ethyl acetate=5:1) to obtain the titled compound (396 mg).

$^1$H-NMR spectrum (CDCl$_3$) δ (ppm): 3.92 (2H, s), 4.58 (2H, s), 5.99 (1H, dt, J=0.92 Hz, 3.3 Hz), 6.05 (1H, d, J=3.3 Hz), 7.22 (2H, d, J=8.2 Hz), 7.34 (2H, d, J=8.2 Hz).

Example 17

5-(1-(4-(5-Chloro-furan-2-ylmethyl)-benzyl)-1H-[1,2,3]triazol-4-yl)-2-methyl-pyridine

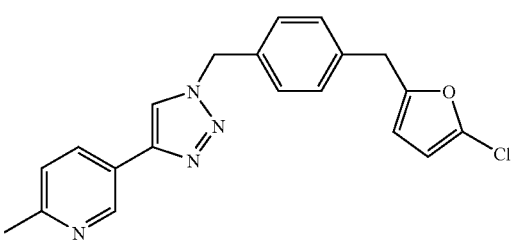

The titled compound (17 mg) was obtained from 5-ethynyl-2-methyl-pyridine (10 mg) described in Manufacturing Example 2-1 and 2-chloro-5-(4-chloromethyl-benzyl)-furan (21 mg) described in Manufacturing Example 16-4, by the same method as in Example 1.

$^1$H-NMR spectrum (DMSO-$d_6$) δ (ppm): 2.47 (3H, s), 3.93 (2H, s), 5.61 (2H, s), 6.22 (1H, d, J=3.1 Hz), 6.32 (1H, d, J=3.3 Hz), 7.24 (2H, d, J=8.2 Hz), 7.29-7.31 (3H, m), 8.07 (1H, dd, J=2.4 Hz, 8.1 Hz), 8.67 (1H, s), 8.88 (1H, d, J=2.2 Hz).

Example 18

5-(1-(4-(5-Chloro-furan-2-ylmethyl)-benzyl)-1H-[1,2,3]triazol-4-yl)-pyridin-2-ylamine

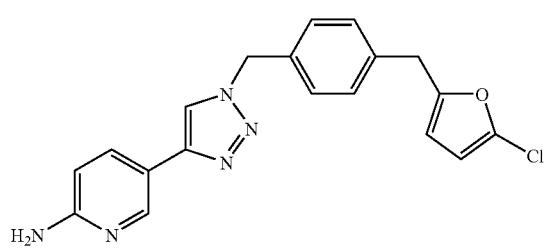

The titled compound (11 mg) was obtained from 5-ethynyl-pyridin-2-ylamine (10 mg) described in Manufacturing Example 3-3 and 2-chloro-5-(4-chloromethyl-benzyl)-furan (23 mg) described in Manufacturing Example 16-4, by the same method as in Example 1.

$^1$H-NMR spectrum (DMSO-$d_6$) δ (ppm): 3.94 (2H, s), 5.57 (2H, s), 6.08 (2H, s), 6.23 (1H, d, J=3.3 Hz), 6.34 (1H, d, J=3.1 Hz), 6.48 (1H, d, J=8.6 Hz), 7.24 (2H, d, J=8.1 Hz), 7.29 (2H, d, J=8.1 Hz), 7.78 (1H, dd, J=2.4 Hz, 8.6 Hz), 8.36 (1H, d, J=2.2 Hz), 8.40 (1H, s).

Example 19

3-(1-(4-(5-Chloro-furan-2-ylmethyl)-benzyl)-1H-[1,2,3]triazol-4-yl)-6-methoxymethyl-pyridin-2-ylamine

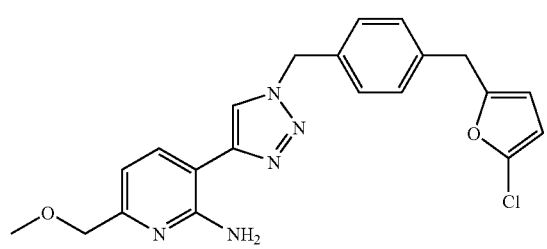

TFA salt (3.7 mg) of the titled compound was obtained from 3-ethynyl-6-methoxymethyl-pyridin-2-ylamine (15 mg) described in Manufacturing Example 19-3 and 2-chloro-5-(4-chloromethyl-benzyl)-furan (25 mg) described in Manufacturing Example 16-4, by the same method as in Example 1.

MS m/e (ESI) (MH$^+$) 410.10 (MH$^+$)

The starting substance 3-ethynyl-6-methoxymethyl-pyridin-2-ylamine was synthesized by the following method.

Manufacturing Example 19-1

(2-Amino-6-methoxymethyl-pyridin-3-yl)methanol

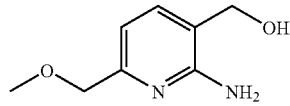

To a mixture of LAH (80%, 220 mg) and THF (5 mL) was added 2-amino-6-methoxymethyl-nicotinic acid methyl ester (300 mg) described in Manufacturing Example 11-3 at 0° C., which was stirred for 20 minutes at the same temperature. A 28% aqueous ammonia solution was added dropwise to the reaction mixture at the same temperature until the LAH was inactivated. The reaction mixture was warmed to room temperature and filtered. The filtrate was evaporated under a reduced pressure to obtain the titled compound (260 mg).

$^1$H-NMR spectrum (CDCl$_3$) δ (ppm): 3.45 (3H, s), 4.39 (2H, s), 4.62 (2H, s), 5.03 (2H, brs), 6.70 (1H, d, J=7.3 Hz), 7.31 (1H, d, J=7.5 Hz).

Manufacturing Example 19-2

2-Amino-6-methoxymethyl-pyridin-3-carbaldehyde

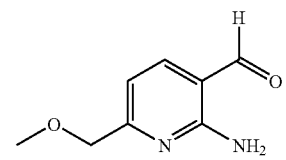

To a mixture of (2-amino-6-methoxymethyl-pyridin-3-yl)methanol (260 mg) described in Manufacturing Example 19-1 and dichloromethane (15 mL) was added manganese dioxide (1.3 g), which was stirred overnight at room temperature. The reaction mixture was filtered through Celite, and the filtrate was evaporated under a reduced pressure. The residue was purified by silica gel column chromatography (ethyl acetate:heptane=3:2) to obtain the titled compound (210 mg).

$^1$H-NMR spectrum (CDCl$_3$) δ (ppm): 3.48 (3H, s), 4.44 (2H, s), 6.87 (1H, d, J=7.9 Hz), 7.82 (1H, d, J=7.7 Hz), 9.84 (1H, s).

Manufacturing Example 19-3

3-Ethynyl-6-methoxymethyl-pyridin-2-ylamine

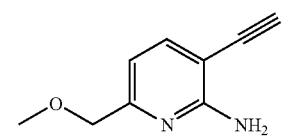

To a mixture of diisopropylamine (0.15 mL) and THF (2 mL) was added n-butyl lithium (1.6M n-hexane solution, 0.68 mL) by drops at −78° C., which was stirred for 30 minutes at the same temperature. Trimethylsilyldiazomethane (2M n-hexane solution, 0.50 mL) was added to the reaction mixture at −78° C., which was stirred for 30 minutes at the same temperature. 2-Amino-6-methoxymethyl-pyridin-3-carbaldehyde (150 mg) described in Manufacturing Example 19-2 and THF (1.5 mL) were added by drops to the reaction mixture at −78° C., which was stirred for 30 minutes at 0° C. The reaction mixture was cooled to −78° C., after which a mixture of acetic acid (0.10 mL) and THF (1 mL) was added by drops thereto. The reaction mixture was gradually raised to 0° C., and was extracted using water and ethyl acetate. The organic layer was washed with saturated brine and the solvent was evaporated under a reduced pressure. The residue was purified by silica gel column chromatography (ethyl acetate:heptane=2:3) to obtain the titled compound (73 mg).

$^1$H-NMR spectrum (CDCl$_3$) δ (ppm): 3.40 (1H, s), 3.45 (3H, s), 4.39 (2H, s), 5.07 (2H, brs), 6.72 (1H, d, J=7.7 Hz), 7.58 (1H, d, J=7.5 Hz).

Example 20

3-(1-(4-(5-Chloro-furan-2-ylmethyl)-benzyl)-1H-[1,2,3]triazol-4-yl)-pyridin-2,6-diamine

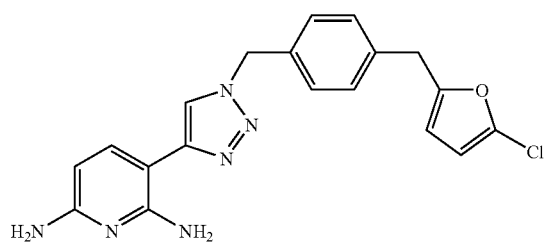

The titled compound (3.6 mg) was obtained from 3-ethynyl-pyridin-2,6-diamine (50 mg) described in Manufacturing Example 4-3 and 2-chloro-5-(4-chloromethyl-benzyl)-furan (100 mg) described in Manufacturing Example 16-4, by the same method as in Example 1.

$^1$H-NMR spectrum (DMSO-d$_6$) δ (ppm): 3.94 (2H, s), 5.57 (2H, s), 5.66 (2H, s), 5.76 (1H, d, J=8.4 Hz), 6.23 (1H, d, J=3.2 Hz), 6.34 (1H, d, J=3.2 Hz), 6.48 (2H, s), 7.24 (2H, d, J=8.4 Hz), 7.29 (2H, d, J=8.4 Hz), 7.46 (1H, d, J=8.4 Hz), 8.34 (1H, s).

Example 21

3-(2-(4-(5-Chloro-furan-2-ylmethyl)-benzyl)-2H-tetrazol-5-yl)-pyridin-2-ylamine

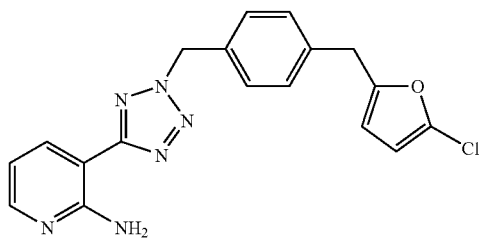

The titled compound (16 mg) was obtained in the same manner as in Example 5 using the 2-chloro-5-(4-chloromethyl-benzyl)-furan described in Manufacturing Example 16-4 and the 3-(2H-tetrazol-5-yl)-pyridin-2-ylamine described in Manufacturing Example 5-1.

$^1$H-NMR spectrum (DMSO-d$_6$) δ (ppm): 3.96 (2H, s), 6.00 (2H, s), 6.24 (1H, d, J=3.2 Hz), 6.34 (1H, d, J=3.2 Hz), 6.72 (1H, dd, J=4.8 Hz, 8.0 Hz), 6.89 (2H, brs), 7.27 (2H, d, J=8.0 Hz), 7.39 (2H, d, J=8.0 Hz), 8.14 (1H, dd, J=2.0 Hz, 4.8 Hz), 8.23 (1H, dd, J=2.0 Hz, 8.0 Hz).

Example 22

3-(2-(4-(5-Chloro-furan-2-ylmethyl)-benzyl)-2H-tetrazol-5-yl)-pyridin-2,6-diamine

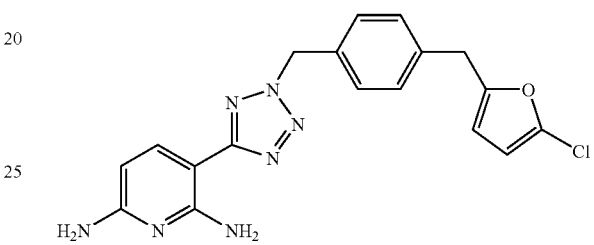

The titled compound (3.9 mg) was obtained in the same manner as in Example 5 using the 2-chloro-5-(4-chloromethyl-benzyl)-furan described in Manufacturing Example 16-4 and the 3-(2H-tetrazol-5-yl)-pyridin-2,6-diamine described in Manufacturing Example 7-3.

$^1$H-NMR spectrum (DMSO-d$_6$) δ (ppm): 3.96 (2H, s), 5.95 (2H, s), 6.13 (1H, d, J=8.8 Hz), 6.24 (1H, d, J=3.2 Hz), 6.35 (1H, d, J=3.2 Hz), 7.26 (2H, d, J=8.0 Hz), 7.37 (2H, d, J=8.0 Hz), 8.19 (1H, d, J=8.8 Hz).

Example 23

3-(5-(4-Pyridin-2-ylmethoxy)-benzyl)-[1,2,4]oxadiazol-3-yl)-pyridin-2-ylamine

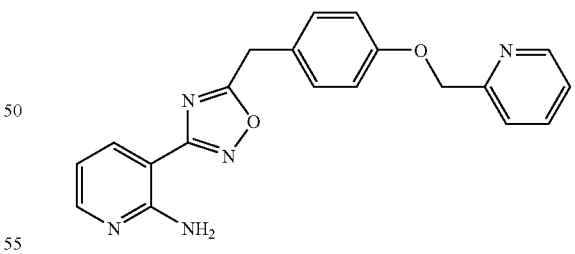

To a solution of THF (2 mL) of 4-(3-(2-amino-pyridin-3-yl)-[1,2,4]oxadiazol-5-ylmethyl)-phenol (22 mg) described in Manufacturing Example 23-1 was added a 5N aqueous sodium hydroxide solution (16 μL) at room temperature, which was stirred for several minutes, and then the solvent was evaporated from the reaction mixture under a reduced pressure. To a solution of DMSO (3.3 mL) of the residue was added at room temperature a separately prepared THF solution of 2-chloromethyl-pyridine (a 5N aqueous sodium hydroxide solution (45 μL) was added to a solution of THF (2 mL) and water (2 mL) of 2-chloromethyl-pyridine hydrochloride (40 mg), which was stirred for several seconds, and then the organic layer was separated), which was stirred for 14 hours and 30 minutes at room temperature. Water was added to the reaction solution, which was then extracted with ethyl acetate. The organic layer was washed with water and saturated brine, then dried over anhydrous magnesium sulfate and filtered, after which the solvent was evaporated from the filtrate under a reduced pressure. The residue was purified by NH silica gel column chromatography (heptane:ethyl acetate=1:1), and then purified by reverse-phase high performance liquid chromatography (using an acetonitrile-water mobile phase (containing 0.1% TFA)) to obtain the titled compound (4.2 mg).

MS m/e (ESI) (MH$^+$) 360.02 (MH$^+$)

$^1$H-NMR spectrum (CDCl$_3$) δ (ppm): 4.24 (2H, s), 5.20 (2H, s), 6.28 (2H, s), 6.75 (1H, dd, J=4.9 Hz, 7.7 Hz), 6.97-7.00 (2H, m), 7.21-7.24 (1H, m), 7.27-7.30 (2H, m), 7.50 (1H, d, J=7.9 Hz), 7.69-7.73 (1H, m), 8.18 (1H, dd, J=1.8 Hz, 4.9 Hz), 8.33 (1H, dd, J=1.8 Hz, 7.7 Hz), 8.59-8.61 (1H, m).

The starting substance 4-(3-(2-amino-pyridin-3-yl)-[1,2,4]oxadiazol-5-ylmethyl)-phenol was synthesized by the following method.

Manufacturing Example 23-1

4-(3-(2-Amino-pyridin-3-yl)-[1,2,4]oxadiazol-5-ylmethyl)-phenol

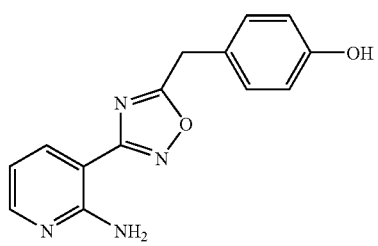

To a solution of TFA (2 mL) of 3-(5-(4-benzyloxy-benzyl)-[1,2,4]-oxadiazol-3-yl)-pyridin-2-ylamine (52 mg) described in Example 13 was added thioanisole (68 μL) at 0° C., which was stirred for 2 hours and 40 minutes at room temperature. Sodium hydrogencarbonate and water were added at 0° C. to the reaction mixture, which was extracted with ethyl acetate. The organic layer was washed with saturated brine, then dried over anhydrous magnesium sulfate, and filtered, after which the solvent was evaporated from the filtrate under a reduced pressure. The residue was purified by silica gel column chromatography (ethyl acetate:methanol=20:1) to obtain the titled compound (40 mg).

$^1$H-NMR spectrum (DMSO-d$_6$) δ (ppm): 4.30 (2H, s), 6.73 (2H, d, J=8.4 Hz), 6.77-6.80 (1H, m), 7.10 (2H, s), 7.17 (2H, d, J=8.2 Hz), 8.17-8.18 (1H, m), 8.24-8.26 (1H, m), 9.42 (1H, s).

Example 24

3-(5-(4-Pyridin-2-ylmethoxy)-benzyl)-[1,3,4]oxadiazol-2-yl)-pyridin-2-ylamine

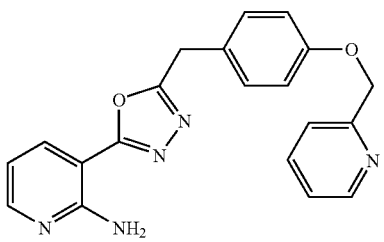

TFA salt (3.7 mg) of the titled compound was obtained from 4-(5-(2-amino-pyridin-3-yl)-[1,3,4]oxadiazol-2-ylmethyl)-phenol (11 mg) described in Manufacturing Example 24-1 and 2-picolyl chloride hydrochloride (13 mg), by the same method as in Example 23.

MS m/e (ESI) (MH$^+$) 360.14 (MH$^+$)

The starting substance 4-(5-(2-amino-pyridin-3-yl)-[1,3,4]oxadiazol-2-ylmethyl)-phenol was synthesized by the following method.

Manufacturing Example 24-1

4-(5-(2-Amino-pyridin-3-yl)-[1,3,4]oxadiazol-2-ylmethyl)-phenol

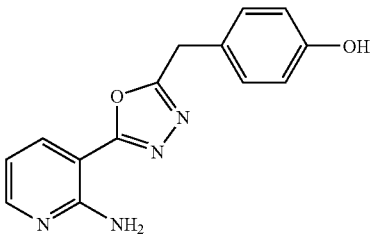

The titled compound (31 mg) was obtained from 3-(5-(4-benzyloxy-benzyl)-[1,3,4]oxadiazol-2-yl))-pyridin-2-ylamine (93 mg) described in Manufacturing Example 9, by the same method as in Manufacturing Example 23-1.

$^1$H-NMR spectrum (DMSO-d$_6$) δ (ppm): 4.20 (2H, s), 6.70-6.74 (2H, m), 6.76 (1H, dd, J=5.0 Hz, 7.8 Hz), 7.13-7.16 (2H, m), 7.45 (2H, brs), 8.02 (1H, dd, J=1.7 Hz, 7.7 Hz), 8.18 (1H, dd, J=1.8 Hz, 4.9 Hz), 9.39 (1H, brs).

Example 25

3-(2-(4-Pyridin-2-ylmethoxy)-benzyl)-2H-tetrazol-5-yl)-pyridin-2-ylamine

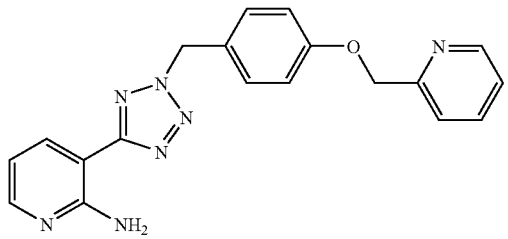

To a solution of THF (10 mL) of (4-(pyridin-2-ylmethoxy)-phenyl)-methanol (130 mg) described in Manufacturing Example 25-2, 3-(2H-tetrazol-5-yl)-pyridin-2-ylamine (100 mg) described in Manufacturing Example 5-1, and triphenylphosphine (210 mg) was added diisopropyl azodicarboxylate (160 mg) at 0° C. The reaction solution was stirred for 10 minutes at room temperature, after which the organic layer was concentrated and purified by NH silica gel chromatography (heptane:ethyl acetate=2:1, then 1:1). The organic layer thus obtained was concentrated and purified by silica gel chromatography (ethyl acetate, then ethyl acetate:methanol=10:1) to obtain the titled compound (72 mg).

$^1$H-NMR spectrum (DMSO-$d_6$) δ (ppm): 5.18 (2H, s), 5.94 (2H, s), 6.73 (1H, dd, J=4.8 Hz, 8.0 Hz), 6.90 (2H, brs), 7.06 (2H, d, J=8.8 Hz), 7.32-7.36 (1H, m), 7.41 (2H, d, J=8.8 Hz), 7.49 (1H, d, J=8.0 Hz), 7.82 (1H, ddd, J=2.0 Hz, 8.0 Hz, 8.0 Hz), 8.14 (1H, dd, J=2.0 Hz, 4.8 Hz), 8.23 (1H, dd, J=2.0 Hz, 8.0 Hz), 8.55-8.59 (1H, m).

The starting substance (4-(pyridin-2-ylmethoxy)-phenyl)-methanol was synthesized by the following method.

Manufacturing Example 25-1

4-(Pyridin-2-ylmethoxy)-benzoic acid methyl ester

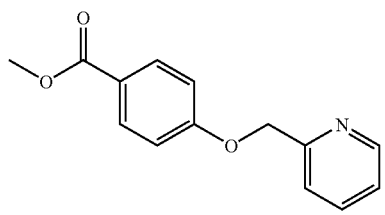

To a solution of THF (50 mL) of 2-(hydroxymethyl)pyridine (1.5 g), methyl p-hydroxybenzoate (2.1 g), and triphenylphosphine (5.0 g) was added diisopropyl azodicarboxylate (3.9 g) at 0° C., which was stirred for 20 minutes at room temperature. Water was added to the reaction solution, which was extracted with ethyl acetate. The solvent was evaporated from the organic layer under a reduced pressure, and the residue was purified by NH silica gel chromatography (heptane:ethyl acetate=2:1), then purified by silica gel chromatography (heptane:ethyl acetate=1:1) to obtain the titled compound (4.9 g).

$^1$H-NMR spectrum (DMSO-$d_6$) δ (ppm): 3.79 (3H, s), 5.25 (2H, s), 7.12 (2H, d, J=8.8 Hz), 7.32-7.36 (1H, m), 7.50 (1H, d, J=8.0 Hz), 7.82 (1H, ddd, J=2.0 Hz, 8.0 Hz, 8.0 Hz), 7.90 (2H, d, J=8.8 Hz), 8.56-8.59 (1H, m).

Manufacturing Example 25-2

(4-(Pyridin-2-ylmethoxy)-phenyl)-methanol

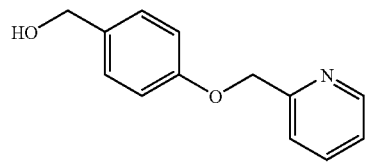

To a solution of THF (50 mL) of 4-(pyridin-2-ylmethoxy)-benzoic acid methyl ester (4.9 g) described in Manufacturing Example 25-1 was added LAH (1.0 g) at 0° C., which was stirred for 20 minutes at room temperature. Water was added to the reaction solution, which was extracted with ethyl acetate. The organic layer was concentrated and purified by silica gel chromatography (heptane:ethyl acetate=1:1, then ethyl acetate) to obtain the titled compound (1.6 g).

$^1$H-NMR spectrum (DMSO-$d_6$) δ (ppm): 4.41 (2H, d, J=6.0 Hz), 5.05 (1H, d, J=6.0 Hz), 5.16 (2H, s), 6.98 (2H, d, J=8.8 Hz), 7.23 (2H, d, J=8.8 Hz), 7.32-7.37 (1H, m), 7.50 (1H, d, J=8.0 Hz), 7.82 (1H, ddd, J=2.0 Hz, 8.0 Hz, 8.0 Hz), 8.56-8.59 (1H, m).

Example 26

3-(1-(4-(Pyridin-2-yloxymethyl)-benzyl)-1H-[1,2,3]triazol-4-yl)-pyridin-2-ylamine

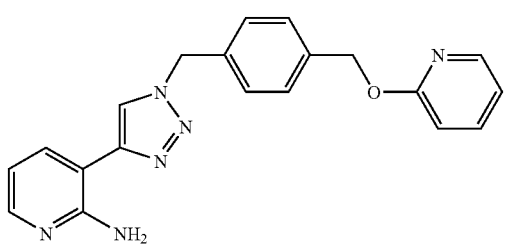

The titled compound (38 mg) was obtained from 3-ethynyl-pyridin-2-ylamine (28 mg) described in Manufacturing Example 1-2 and 2-(4-chloromethyl-benzyloxy)pyridine (55 mg) described in Manufacturing Example 26-2, by the same method as in Example 1.

$^1$H-NMR spectrum (DMSO-$d_6$) δ (ppm): 5.32 (2H, s), 5.65 (2H, s), 6.60 (1H, dd, J=4.9 Hz, 7.7 Hz), 6.84 (1H, d, J=8.2 Hz), 6.86 (2H, s), 6.95-6.98 (1H, m), 7.35 (2H, d, J=8.1 Hz), 7.44 (2H, d, J=8.1 Hz), 7.67-7.71 (1H, m), 7.81 (1H, dd, J=1.7 Hz, 7.5 Hz), 7.93 (1H, dd, J=1.7 Hz, 4.8 Hz), 8.14 (1H, dd, J=1.7 Hz, 5.5 Hz), 8.69 (1H, s).

The starting substance 2-(4-chloromethyl-benzyloxy)pyridine was synthesized by the following method.

Manufacturing Example 26-1

(4-(Pyridin-2-yloxymethyl)-phenyl)-methanol

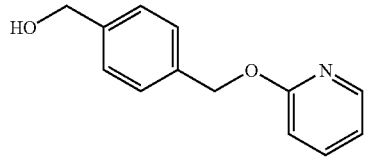

To a solution of 1,4-benzenedimethanol (5.5 g) and DMF (15 mL) of 2-fluoropyridine (1.3 g) was added NaH (1.4 g/66% in oil) at 0° C., which was stirred for 1 hour at 70° C. The reaction mixture was cooled to room temperature and extracted with ethyl acetate. The organic layer was washed with saturated brine, and the solvent was evaporated under a reduced pressure. The residue was purified by NH silica gel column chromatography (ethyl acetate:heptane=1:1) to obtain the titled compound (1.9 g).

$^1$H-NMR spectrum (CDCl$_3$) δ (ppm): 4.71 (2H, s), 5.38 (2H, s), 6.81 (1H, td, J=0.9 Hz, 8.4 Hz), 6.89 (1H, ddd, J=0.9 Hz, 5.1 Hz, 7.1 Hz), 7.37-7.47 (4H, m), 7.59 (1H, ddd, J=2.0 Hz, 7.1 Hz, 8.3 Hz), 8.17 (1H, ddd, J=0.7 Hz, 2.0 Hz, 5.1 Hz).

Manufacturing Example 26-2

2-(4-Chloromethyl-benzyloxy)-pyridine

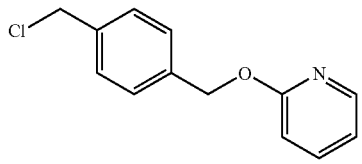

(4-(Pyridin-2-yloxymethyl)-phenyl)methanol (540 mg, 2.51 mmol) described in Manufacturing Example 26-1, triphenylphosphine (856 mg, 3.27 mmol), and carbon tetrachloride (10.8 g, 10.2 mmol) were stirred for 2 hours and 10 minutes under heating and reflux. The reaction solution was cooled to room temperature, and the solvent was evaporated under a reduced pressure. The residue was purified by silica gel column chromatography (heptane:ethyl acetate=8:1) to obtain the titled compound (300 mg).

$^1$H-NMR spectrum (DMSO-d$_6$) δ (ppm): 4.76 (2H, s), 5.35 (2H, s), 6.86-6.90 (1H, m), 6.97-7.20 (1H, m), 7.44 (4H, s), 7.70-7.76 (1H, m), 8.15-8.18 (1H m).

Example 27

3-(2-(4-(Pyridin-2-ylmethoxy)-benzyl)-2H-tetrazol-5-yl)-pyridin-2,6-diamine

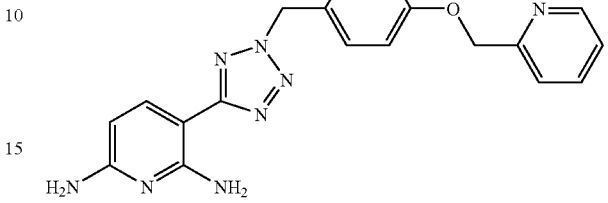

The titled compound (85 mg) was obtained in the same manner as in Example 5, using 2-(4-chloromethyl-benzyloxy)pyridine (120 mg) described in Manufacturing Example 26-2 and 3-(2H-tetrazol-5-yl)-pyridin-2,6-diamine (80 mg) described in Manufacturing Example 7-3.

$^1$H-NMR spectrum (DMSO-d$_6$) δ (ppm): 5.34 (2H, s), 5.85 (1H, d, J=8.0 Hz), 5.93 (2H, s), 6.08 (2H, brs), 6.47 (2H, brs), 6.85-6.89 (1H, m), 6.98 (1H, ddd, J=2.0 Hz, 8.0 Hz, 8.0 Hz), 7.39 (2H, d, J=8.0 Hz), 7.46 (2H, d, J=8.0 Hz), 7.70-7.76 (1H, m), 7.85 (1H, d, J=8.0 Hz), 8.14-8.18 (1H, m).

Example 28

3-(1-(3-Phenoxy-benzyl)-1H-[1,2,3]triazol-4-yl)-pyridin-2-ylamine

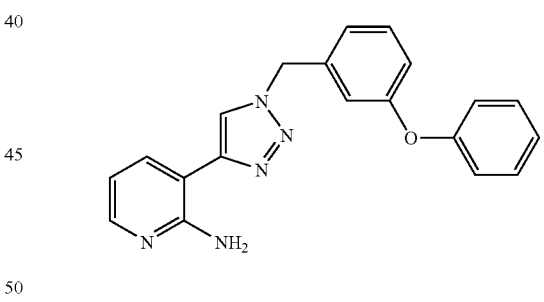

The titled compound (8.4 mg) was obtained from 3-ethynyl-pyridin-2-ylamine (10 mg) described in Manufacturing Example 1-2 and 1-chloromethyl-3-phenoxy-benzene (20 mg) described in Manufacturing Example 28-1, by the same method as in Example 1.

MS m/e (ESI) (MH$^+$) 344.30 (MH$^+$)

$^1$H-NMR spectrum (DMSO-d$_6$) δ (ppm): 5.67 (2H, s), 6.63 (1H, dd, J=4.8 Hz, 7.5 Hz), 6.88 (2H, s), 6.96 (1H, dd, J=2.0 Hz, 7.9 Hz), 7.01-7.05 (3H, m), 7.10 (1H, d, J=8.1 Hz), 7.15 (1H, t, J=7.5 Hz), 7.37-7.42 (3H, m), 7.83 (1H, dd, J=1.8 Hz, 7.5 Hz), 7.96 (1H, dd, J=1.8 Hz, 4.8 Hz), 8.71 (1H, s).

The starting substance 1-chloromethyl-3-phenoxy-benzene was synthesized by the following method.

Manufacturing Example 28-1

1-Chloromethyl-3-phenoxy-benzene

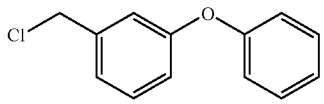

To a solution of carbon tetrachloride (40 mL) of (3-phenoxy-phenyl)-methanol (2.0 g) was added triphenylphosphine (3.2 g) at room temperature, which was heated to reflux under a nitrogen atmosphere for 5 hours and 40 minutes. The reaction mixture was cooled to room temperature and the solvent was evaporated under a reduced pressure. The residue was purified by silica gel column chromatography (heptane:ethyl acetate=10:1) to obtain the titled compound (2.1 g).

$^1$H-NMR spectrum (DMSO-$d_6$) δ (ppm): 4.37 (2H, s), 6.94-6.97 (1H, m), 7.00-7.03 (2H, m), 7.05-7.06 (1H, m), 7.13-7.20 (3H, m), 7.37-7.41 (2H, m).

Example 29

5-(1-(3-Phenoxy-benzyl)-1H-[1,2,3]triazol-4-yl)-pyridin-2-ylamine

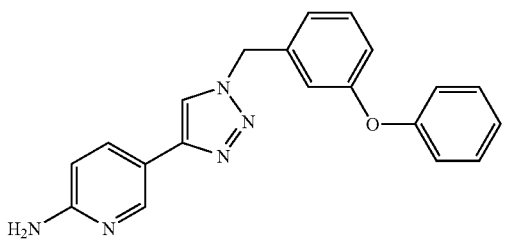

The titled compound (11 mg) was obtained from 5-ethynyl-pyridin-2-ylamine (10 mg) described in Manufacturing Example 3-3 and 1-chloromethyl-3-phenoxy-benzene (20 mg) described in Manufacturing Example 28-1, by the same method as in Example 1.

$^1$H-NMR spectrum (DMSO-$d_6$) δ (ppm): 5.60 (2H, s), 6.09 (2H, s), 6.49 (1H, d, J=8.8 Hz), 6.93-6.96 (1H, m), 7.01-7.03 (3H, m), 7.07 (1H, d, J=8.1 Hz), 7.15 (1H, t, J=7.5 Hz), 7.37-7.41 (3H, m), 7.78 (1H, dd, J=2.4 Hz, 8.8 Hz), 8.37 (1H, d, J=2.4 Hz), 8.43 (1H, s).

Example 30

3-(1-(3-Phenoxy-benzyl)-1H-[1,2,3]triazol-4-yl)-pyridin-2,6-diamine

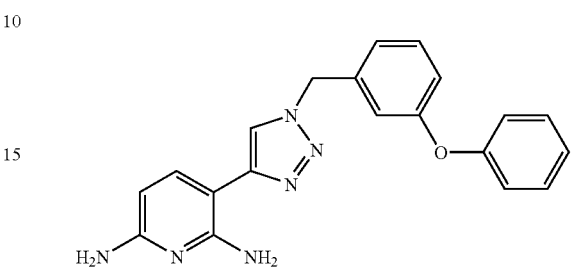

The titled compound (6.7 mg) was obtained from 3-ethynyl-pyridin-2,6-diamine (70 mg) described in Manufacturing Example 4-3 and 1-chloromethyl-3-phenoxy-benzene (140 mg) described in Manufacturing Example 28-1, by the same method as in Example 1.

MS m/e (ESI) (MH$^+$) 359.32 (MH$^+$)

Example 31

3-(2-(3-Phenoxy-benzyl)-2H-tetrazol-5-yl)-pyridin-2-ylamine

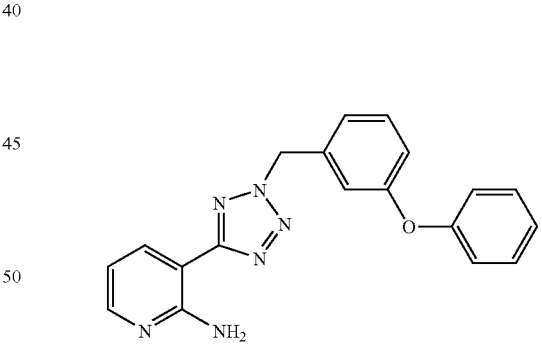

The titled compound (37 mg) was obtained from 3-phenoxybenzyl alcohol (61 mg) and 3-(2H-tetrazol-5-yl)-pyridin-2-ylamine (150 mg) described in Manufacturing Example 5-1, by the same method as in Example 25.

$^1$H-NMR spectrum (DMSO-$d_6$) δ (ppm): 6.03 (2H, s), 6.74 (1H, dd, J=4.8 Hz, 8.0 Hz), 6.89 (2H, brs), 6.98-7.06 (3H, m), 7.09 (1H, s), 7.14-7.19 (2H, m), 7.37-7.45 (3H, m), 8.16 (1H, dd, J=2.0 Hz, 4.8 Hz), 8.22 (1H, dd, J=2.0 Hz, 8.0 Hz).

Example 32

3-(1-(4-Phenoxy-benzyl)-1H-[1,2,3]triazol-4-yl)-pyridin-2-ylamine

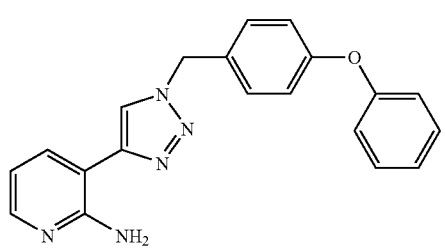

The titled compound (7.3 mg) was obtained from 3-ethynyl-pyridin-2-ylamine (10 mg) described in Manufacturing Example 1-2 and 1-chloromethyl-4-phenoxy-benzene (20 mg) described in Manufacturing Example 32-1, by the same method as in Example 1.

MS m/e (ESI) (MH$^+$) 344.30 (MH$^+$)

$^1$H-NMR spectrum (DMSO-d$_6$) δ (ppm): 5.65 (2H, s), 6.62 (1H, dd, J=4.9 Hz, 7.5 Hz), 6.90 (2H, s), 7.00-7.04 (4H, m), 7.15 (1H, t, J=7.3 Hz), 7.37-7.42 (4H, m), 7.84 (1H, dd, J=1.8 Hz, 7.5 Hz), 7.96 (1H, dd, J=1.8 Hz, 4.9 Hz), 8.71 (1H, s).

The starting substance 1-chloromethyl-4-phenoxy-benzene was synthesized by the following method.

Manufacturing Example 32-1

1-Chloromethyl-4-phenoxy-benzene

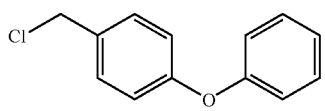

To a solution of carbon tetrachloride (8.2 mL) of (4-phenoxy-phenyl)-methanol (410 mg) was added triphenylphosphine (640 mg) at room temperature, which was heated to reflux for 7 hours and 40 minutes under a nitrogen atmosphere. The reaction mixture was cooled to room temperature and the solvent was evaporated under a reduced pressure. The residue was purified by silica gel column chromatography (heptane:ethyl acetate=10:1) to obtain the titled compound (410 mg).

$^1$H-NMR spectrum (DMSO-d$_6$) δ (ppm): 4.76 (2H, s), 6.98-7.05 (4H, m), 7.15-7.19 (1H, m), 7.39-7.46 (4H, m).

Example 33

5-(1-(4-Phenoxy-benzyl)-1H-[1,2,3]triazol-4-yl)-pyridin-2-ylamine

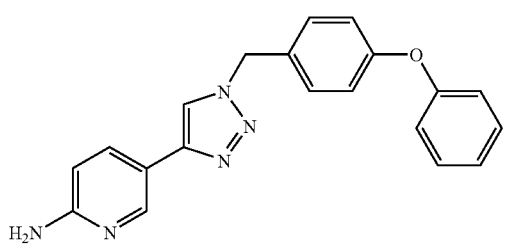

The titled compound (9.0 mg) was obtained from 5-ethynyl-pyridin-2-ylamine (10 mg) described in Manufacturing Example 3-3 and 1-chloromethyl-4-phenoxy-benzene (20 mg) described in Manufacturing Example 32-1, by the same method as in Example 1.

$^1$H-NMR spectrum (DMSO-d$_6$) δ (ppm): 5.58 (2H, s), 6.09 (2H, s), 6.49 (1H, dd, J=0.73 Hz, 8.6 Hz), 7.00-7.03 (4H, m), 7.15 (1H, t, J=7.5 Hz), 7.36-7.41 (4H, m), 7.79 (1H, dd, J=2.4 Hz, 8.6 Hz), 8.37 (1H, d, J=2.4 Hz), 8.42 (1H, s).

Example 34

3-(1-(4-Phenoxy-benzyl)-1H-[1,2,3]triazol-4-yl)-pyridin-2,6-diamine

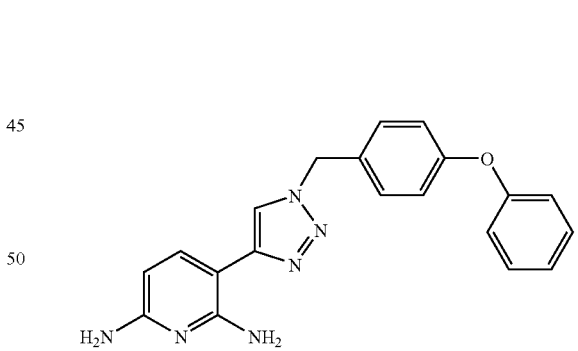

The titled compound (1.5 mg) was obtained from 3-ethynyl-pyridin-2,6-diamine (70 mg) described in Manufacturing Example 4-3 and 1-chloromethyl-3-phenoxy-benzene (130 mg) described in Manufacturing Example 32-1, by the same method as in Example 1.

$^1$H-NMR spectrum (DMSO-d$_6$) δ (ppm): 5.57 (2H, s), 5.67 (2H, s), 5.67 (1H, d, J=8.4 Hz), 6.48 (2H, s), 7.00-7.02 (4H, m), 7.13-7.17 (1H, m), 7.37-7.41 (4H, m), 7.47 (1H, d, J=8.4 Hz), 8.36 (1H, s).

Example 35

3-(2-(4-Phenoxy-benzyl)-2H-tetrazol-5-yl)-pyridin-2-ylaine

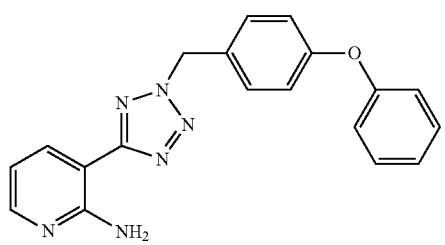

The titled compound (20 mg) was obtained from 4-phenoxybenzyl alcohol (93 mg) and 3-(2H-tetrazol-5-yl)-pyridin-2-ylamine (50 mg) described in Manufacturing Example 5-1, by the same method as in Example 25.

$^1$H-NMR spectrum (DMSO-$d_6$) δ (ppm): 6.00 (2H, s), 6.73 (1H, dd, J=4.8 Hz, 8.0 Hz), 6.90 (2H, brs), 7.00-7.06 (4H, m), 7.14-7.20 (1H, m), 7.37-7.44 (2H, m), 7.48 (2H, d, J=8.0 Hz), 8.14-8.17 (1H, m), 8.22-8.26 (1H, m).

Example 36

3-(1-(5-Phenoxymethyl-pyridin-2-ylmethyl)-1H-[1,2,3]triazol-4-yl)-pyridin-2,6-diamine

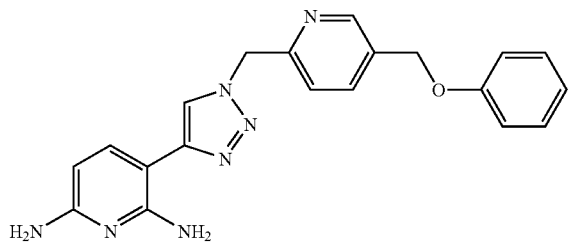

The titled compound (1.8 mg) was obtained from 3-ethynyl-pyridin-2,6-diamine (70 mg) described in Manufacturing Example 4-3 and 1-chloromethyl-5-phenoxymethyl-pyridine (140 mg) described in Manufacturing Example 37-1, by the same method as in Example 1.

$^1$H-NMR spectrum (DMSO-$d_6$) δ (ppm): 5.15 (2H, s), 5.68 (2H, s), 5.73 (2H, s), 5.77 (1H, d, J=8.0 Hz), 6.49 (2H, s), 6.93-6.97 (1H, m), 7.00-7.03 (2H, m), 7.28-7.35 (3H, m), 7.49 (1H, d, J=8.0 Hz), 7.90-7.92 (1H, m), 8.38 (1H, s), 8.64 (1H, m).

Example 37

3-(1-(5-Phenoxymethyl-pyridin-2-ylmethyl)-1H-[1,2,3]triazol-4-yl)-pyridin-2-ylamine

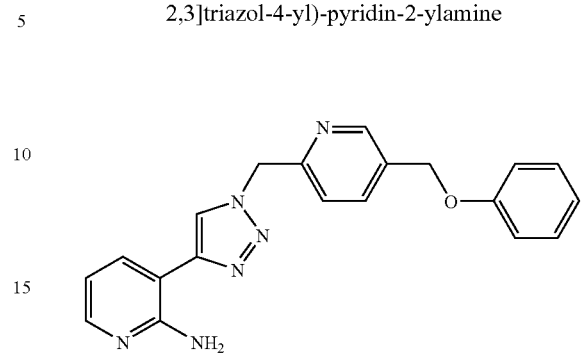

The titled compound (13 mg) was obtained from 3-ethynyl-pyridin-2-ylamine (10 mg) described in Manufacturing Example 1-2 and 2-chloromethyl-5-phenoxymethyl-pyridine (22 mg) described in Manufacturing Example 37-1, by the same method as in Example 1.

$^1$H-NMR spectrum (DMSO-$d_6$) δ (ppm): 4.93 (2H, s), 5.59 (2H, s), 6.41 (1H, dd, J=2.7 Hz, 7.5 Hz), 6.68 (2H, s), 6.73 (1H, t, J=7.3 Hz), 6.79 (2H, d, J=7.9 Hz), 7.08 (2H, dd, J=7.3 Hz, 8.8 Hz), 7.18 (1H, d, J=7.7 Hz), 7.64 (1H, dd, J=1.8 Hz, 7.5 Hz), 7.70 (1H, dd, J=2.0 Hz, 7.9 Hz), 7.74 (1H, dd, J=1.8 Hz, 4.8 Hz), 8.42 (1H, d, J=2.0 Hz), 8.52 (1H, s).

The starting substance 2-chloromethyl-5-phenoxymethyl-pyridine was synthesized by the following method.

Manufacturing Example 37-1

2-Chloromethyl-5-phenoxymethyl-pyridine

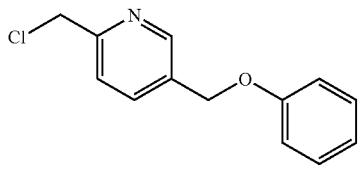

To a solution of carbon tetrachloride (20 mL) of a known compound (5-phenoxymethyl-pyridin-2-yl)-methanol (1.4 g) was added triphenylphosphine (2.1 g) at room temperature, which was heated to reflux for 6 hours and 15 minutes under a nitrogen atmosphere. The reaction mixture was cooled to room temperature, after which the solvent was evaporated under a reduced pressure. The residue was purified by silica gel column chromatography (heptane:ethyl acetate=2:1) to obtain the titled compound (1.3 g).

$^1$H-NMR spectrum (DMSO-$d_6$) δ (ppm): 4.79 (2H, s), 5.17 (2H, s), 6.96 (1H, t, J=7.3 Hz), 7.03 (2H, d, J=8.1 Hz), 7.29-7.33 (2H, m), 7.58 (1H, d, J=8.1 Hz), 7.92 (1H, dd, J=2.0 Hz, 8.1 Hz), 8.65 (1H, d, J=2.0 Hz).

Example 38

3-(1-(5-Benzyloxy-pyridin-2-ylmethyl)-1H-[1,2,3]triazol-4-yl)-pyridin-2-ylamine

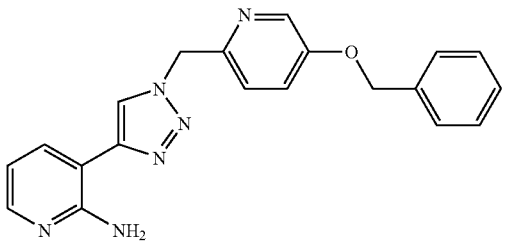

The titled compound (38 mg) was obtained from 3-ethynyl-pyridin-2-ylamine (30 mg) described in Manufacturing Example 1-2 and 5-benzyloxy-2-chloromethyl-pyridine (65 mg) described in Manufacturing Example 38-1, by the same method as in Example 1.

$^1$H-NMR spectrum (DMSO-d$_6$) δ (ppm): 5.19 (2H, s), 5.70 (2H, s), 6.62 (1H, dd, J=4.8 Hz, 7.5 Hz), 6.89 (2H, s), 7.34-7.46 (6H, m), 7.51 (1H, dd, J=2.9 Hz, 8.6 Hz), 7.85 (1H, dd, J=1.8 Hz, 7.5 Hz), 7.95 (1H, dd, J=1.8 Hz, 4.8 Hz), 8.33 (1H, d, J=2.9 Hz), 8.68 (1H, s).

The starting substance 5-benzyloxy-2-chloromethyl-pyridine was synthesized by the following method.

Manufacturing Example 38-1

5-Benzyloxy-2-chloromethyl-pyridine

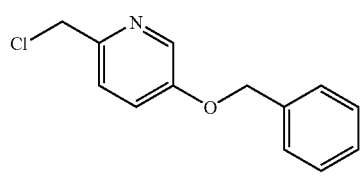

To a solution of carbon tetrachloride (10 mL) of a known compound (5-benzyloxy-pyridin-2-yl)-methanol (500 mg) was added triphenylphosphine (791 mg) at room temperature, which was heated to reflux for 19 hours and 35 minutes under a nitrogen atmosphere. The reaction mixture was cooled to room temperature, after which the solvent was evaporated under a reduced pressure. The residue was purified by silica gel column chromatography (heptane:ethyl acetate=3:1) to obtain the titled compound (386 mg).

$^1$H-NMR spectrum (CDCl$_3$) δ (ppm): 4.64 (2H, s), 5.12 (2H, s), 7.25-7.28 (1H, m), 7.35-7.44 (6H, m), 8.34 (1H, d, J=2.7 Hz).

Example 39

3-(2-(5-Benzyloxy-pyridin-2-ylmethyl)-2H-tetrazol-5-yl)-pyridin-2-ylamine

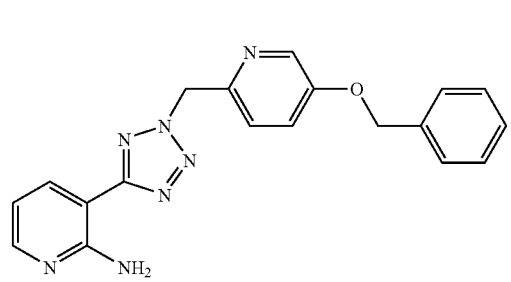

The titled compound (7.0 mg) was obtained from a known compound (5-benzyloxy-pyridin-2-yl)-methanol (130 mg) and 3-(2H-tetrazol-5-yl)-pyridin-2-ylamine (100 mg) described in Manufacturing Example 5-1, by the same method as in Example 25.

$^1$H-NMR spectrum (DMSO-d$_6$) δ (ppm): 5.19 (2H, s), 6.05 (2H, s), 6.73 (1H, dd, J=4.8 Hz, 8.0 Hz), 6.88 (2H, brs), 7.30-7.55 (7H, m), 8.14 (1H, dd, J=2.0 Hz, 4.8 Hz), 8.22 (1H, dd, J=2.0 Hz, 8.0 Hz), 8.30 (1H, d, J=2.0 Hz).

Example 40

3-(2-(5-Benzyloxy-pyridin-2-ylmethyl)-2H-tetrazol-5-yl)-pyridin-2,6-diamine

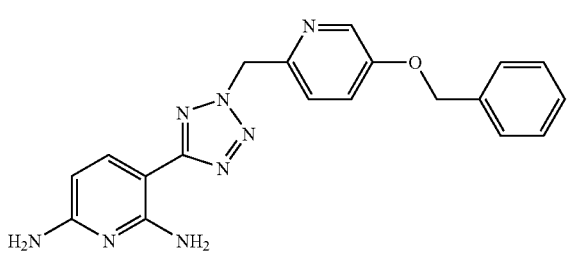

The titled compound (44 mg) was obtained from a known compound (5-benzyloxy-pyridin-2-yl)-methanol (73 mg) and 3-(2H-tetrazol-5-yl)-pyridin-2,6-diamine (100 mg) described in Manufacturing Example 7-3, by the same method as in Example 25.

$^1$H-NMR spectrum (DMSO-d$_6$) δ (ppm): 5.18 (2H, s), 5.85 (1H, d, J=8.0 Hz), 5.94 (2H, s), 6.07 (2H, brs), 6.46 (2H, brs), 7.30-7.48 (6H, m), 7.52 (1H, dd, J=2.0 Hz, 8.0 Hz), 7.84 (1H, d, J=8.0 Hz), 8.30 (1H, d, J=2.0 Hz).

Example 41

3-[1-(4-Butoxymethyl-benzyl)-1H-[1,2,3]triazol-4-yl]-6-methoxymethyl-pyridin-2-ylamine

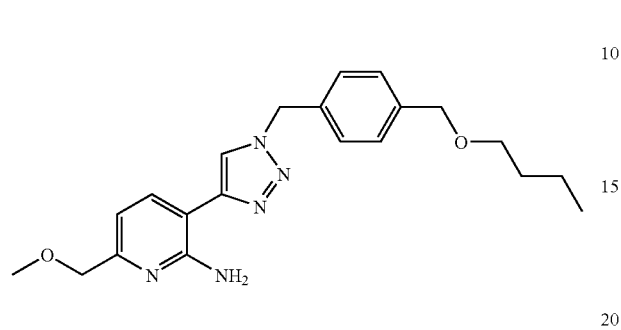

TFA salt (1.4 mg) of the titled compound was obtained from 3-ethynyl-6-methoxymethyl-pyridin-2-ylamine (15 mg) described in Manufacturing Example 19-3 and 1-butoxymethyl-4-chloromethyl-benzene (22 mg) described in Manufacturing Example 43-4, by the same method as in Example 1.

MS m/e (ESI) (MH$^+$) 382.10 (MH$^+$)

Example 42

3-(1-(4-Butoxymethyl-benzyl)-1H-[1,2,3]triazol-4-yl)-pyridin-2,6-diamine

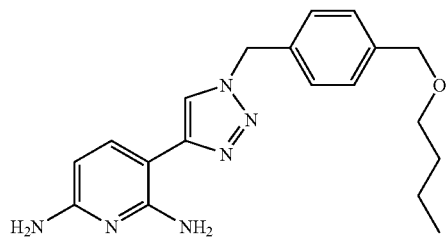

The titled compound (6.2 mg) was obtained from 3-ethynyl-pyridin-2,6-diamine (100 mg) described in Manufacturing Example 4-3 and 1-butoxymethyl-4-chloromethyl-benzene (190 mg) described in Manufacturing Example 43-4, by the same method as in Example 1.

$^1$H-NMR spectrum (DMSO-d$_6$) δ (ppm): 0.86 (3H, t, J=7.6 Hz), 1.29-1.35 (2H, m), 1.47-1.52 (2H, m), 3.40 (2H, t, J=6.4 Hz), 4.43 (2H, s), 5.59 (2H, s), 5.67 (2H, m), 5.76 (1H, d, J=8.4 Hz), 6.48 (2H, s), 7.32 (4H, s), 7.46 (1H, d, J=8.4 Hz), 8.34 (1H, s).

Example 43

3-(1-(4-Butoxymethyl-benzyl)-1H-[1,2,3]triazol-4-yl)-pyridin-2-ylamine

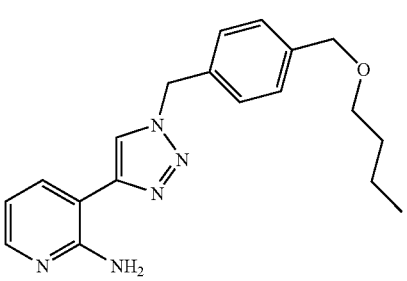

The titled compound (15 mg) was obtained from 3-ethynyl-pyridin-2-ylamine (20 mg) described in Manufacturing Example 1-2 and 1-butoxymethyl-4-chloromethyl-benzene (40 mg) described in Manufacturing Example 43-4, by the same method as in Example 1, the product of which was purified by silica gel chromatography (heptane:ethyl acetate=2:1), and then purified by reverse-phase high performance liquid chromatography (using an acetonitrile-water mobile phase containing 0.1% TFA).

MS m/e (ESI) (MH$^+$) 338.30 (MH$^+$)

The starting substance 1-butoxymethyl-4-chloromethyl-benzene was synthesized by the following method.

Manufacturing Example 43-1

4-Butoxymethyl-benzonitrile

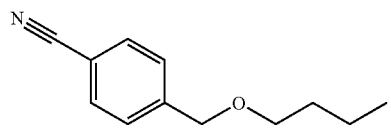

To a mixture of NaH (270 mg/66% in oil) and THF (20 mL) was added n-butanol (1.1 mL) at 0° C., which was stirred for 45 minutes at room temperature. The reaction mixture was cooled to 0° C., and a mixture of 4-cyanobenzyl bromide (1.5 g) and THF (10 mL) was added by drops thereto at the same temperature. The reaction mixture was stirred for 3 hours at room temperature, after which DMF (10 mL) was added to the reaction mixture, which was stirred for 4.5 hours at the same temperature. Water was added to the reaction mixture, which was then extracted with diethyl ether. The organic layer was washed with saturated brine, after which the solvent was evaporated from the organic layer under a reduced pressure. The residue was purified by NH silica gel column chromatography (ethyl acetate:heptane=1:6) to obtain the titled compound (1.2 g).

¹H-NMR spectrum (CDCl₃) δ (ppm): 0.93 (3H, t, J=7.3 Hz), 1.37-1.46 (2H, m), 1.59-1.66 (2H, m), 3.50 (2H, t, J=6.6 Hz), 4.55 (2H, s), 7.43-7.46 (2H, m), 7.62-7.65 (2H, m).

Manufacturing Example 43-2

4-Butoxymethyl-benzylamine

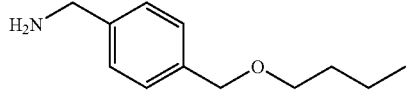

To a mixture of LAH (80%, 600 mg) and THF (10 mL) were added 4-butoxymethyl-benzonitrile (600 mg) described in Manufacturing Example 43-1 and THF (10 mL) at 0° C., which was stirred for 4 hours at room temperature. A 28% aqueous ammonia solution was added by drops to the reaction mixture at 0° C., and the excess LAH was quenched. The temperature was raised to room temperature, and then filtration was performed. The solvent was evaporated from the filtrate under a reduced pressure to obtain of the titled compound (620 mg).

¹H-NMR spectrum (CDCl₃) δ (ppm): 0.92 (3H, t, J=7.3 Hz), 1.37-1.44 (2H, m), 1.56-1.63 (2H, m), 3.47 (2H, t, J=6.6 Hz), 3.86 (2H, s), 4.49 (2H, s), 7.27-7.32 (4H, m).

Manufacturing Example 43-3

(4-Butoxymethyl-phenyl)-methanol

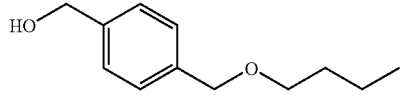

To a mixture of 4-butoxymethyl-benzylamine (250 mg) described in Manufacturing Example 43-2, acetic acid (2 mL), and water (2 mL) was added sodium nitrite (1.1 g) at 0° C., which was stirred for 40 minutes at room temperature. The reaction mixture was added to a mixture of ethyl acetate and water, and then extracted. The organic layer was washed with a saturated aqueous solution of sodium hydrogen carbonate and then with saturated brine. The solvent was evaporated from the organic layer under a reduced pressure. Methanol (2 mL) and potassium carbonate (360 mg) were added to the residue, and the reaction mixture was stirred for 1.5 hours at room temperature. The solvent was evaporated from the reaction mixture under a reduced pressure. The residue was purified by neutral silica gel column chromatography (ethyl acetate:heptane=1:1) to obtain the titled compound (200 mg).

¹H-NMR spectrum (CDCl₃) δ (ppm): 0.92 (3H, t, J=7.3 Hz), 1.35-1.44 (2H, m), 1.57-1.64 (2H, m), 3.47 (2H, t, J=6.6 Hz), 4.50 (2H, s), 4.69 (2H, s), 7.34 (4H, s).

Manufacturing Example 43-4

1-Butoxymethyl-4-chloromethyl-enzene

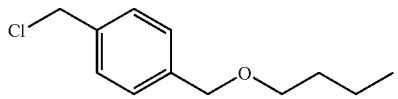

A mixture of (4-butoxymethyl-phenyl)-methanol (190 mg) described in Manufacturing Example 43-3, triphenylphosphine (310 mg), and carbon tetrachloride (3 mL) was heated to reflux for 7 hours. The reaction mixture was cooled to room temperature, and then the solvent was evaporated under a reduced pressure. The residue was purified by neutral silica gel column chromatography (ethyl acetate:heptane=1:15) to obtain the titled compound (180 mg).

¹H-NMR spectrum (CDCl₃) δ (ppm): 0.92 (3H, t, J=7.3 Hz), 1.35-1.45 (2H, m), 1.57-1.64 (2H, m), 3.47 (2H, t, J=6.6 Hz), 4.50 (2H, s), 4.59 (2H, s), 7.32-7.38 (4H, m).

Example 44

5-(1-(4-Butoxymethyl-benzyl)-1H-[1,2,3]triazol-4-yl)-pyridin-2-ylamine

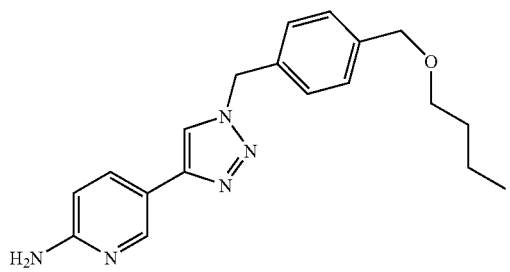

The titled compound (11 mg) was obtained from 3-ethynyl-pyridin-2-ylamine (20 mg) described in Manufacturing Example 3-3 and 1-butoxymethyl-4-chloromethyl-benzene (40 mg) described in Manufacturing Example 43-4, by the same method as in Example 1, the product of which was purified by silica gel chromatography (ethyl acetate), and then purified by reverse-phase high performance liquid chromatography (using an acetonitrile-water mobile phase containing 0.1% TFA).

MS m/e (ESI) (MH⁺) 338.11 (MH⁺)

Example 45

3-(5-(4-Butoxy-benzyl)-[1,3,4]oxadiazol-2-yl)-pyridin-2-ylamine

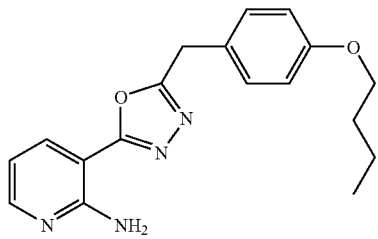

TFA salt (3.1 mg) of the titled compound was obtained from 4-(5-(2-amino-pyridin-3-yl)-[1,3,4]oxadiazol-2-ylmethyl)-phenol (7.0 mg) described in Manufacturing Example 24-1 and 1-iodobutane (8.9 mg), by the same method as in Example 23.

MS m/e (ESI) (MH$^+$) 325.27 (MH$^+$)

Example 46

3-(2-(5-Phenoxy-thiophen-2-ylmethyl)-2H-tetrazol-5-yl)-pyridin-2-ylamine

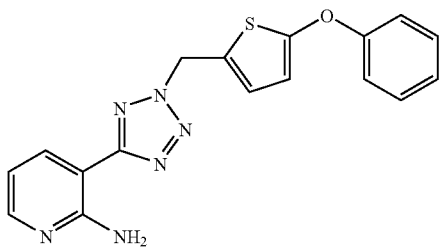

To a solution of THF (5 mL) and (5-phenoxy-thiophen-2-yl)-methanol (100 mg) described in Manufacturing Example 46-1, 3-(2H-tetrazol-5-yl)-pyridin-2-ylamine (79 mg) described in Manufacturing Example 5-1, and triphenylphosphine (250 mg) was added diethyl azodicarboxylate (170 mg, 40% toluene solution) at room temperature, which was stirred for 20 minutes. Water was added to the reaction solution, which was then extracted with ethyl acetate. The solvent was evaporated from the organic layer under a reduced pressure and purified by silica gel chromatography (hexane:ethyl acetate=2:1, then 1:1), after which was purified by NH silica gel column chromatography (heptane:ethyl acetate=2:1). The solvent was evaporated under a reduced pressure from the organic layer thus obtained, methanol and 2N aqueous sodium hydroxide were added to the residue, which was stirred for 20 minutes at 80° C. Water was added to the reaction solution, which was extracted with ethyl acetate, and the organic layer was washed three times with water. The solvent was evaporated under a reduced pressure and the organic layer was purified by NH silica gel chromatography (ethyl acetate) to obtain the titled compound (20 mg).

$^1$H-NMR spectrum (DMSO-d$_6$) δ (ppm): 6.17 (2H, s), 6.59 (1H, d, J=4.0 Hz), 6.73-6.77 (1H, m), 6.91 (2H, brs), 7.10-7.21 (4H, m), 7.41 (2H, dd, J=8.0 Hz, 8.0 Hz), 8.14-8.18 (1H, m), 8.23-8.28 (1H, m).

The starting substance (5-phenoxy-thiophen-2-yl)-methanol was synthesized by the following method.

Manufacturing Example 46-1

(5-Phenoxy-thiophen-2-yl)-methanol

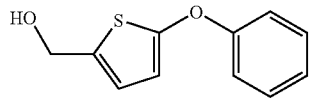

To a solution of THF (60 mL) and 5-phenoxy-thiophene-2-carbaldehyde (2.8 g) was added LAH (390 mg) at 0° C., which was stirred for 10 minutes at room temperature. Water was added to the reaction solution, which was then extracted with ethyl acetate. The solvent was evaporated under a reduced pressure and the organic layer was purified by NH silica gel chromatography (ethyl acetate), and then purified by silica gel chromatography (hexane:ethyl acetate=4:1, then 2:1) to obtain the titled compound (2.0 g).

$^1$H-NMR spectrum (DMSO-d$_6$) δ (ppm): 4.52 (2H, d, J=6.0 Hz), 5.43 (1H, t, J=6.0 Hz), 6.52 (1H, d, J=4.0 Hz), 6.71-6.75 (1H, m), 7.07-7.18 (3H, m), 7.36-7.42 (2H, m).

Example 47

5-(2-(5-Phenoxy-thiophen-2-ylmethyl)-2H-tetrazol-5-yl)-pyridin-2-ylamine

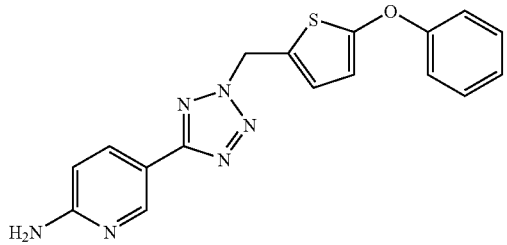

The titled compound (14 mg) was obtained from 5-(2H-tetrazol-5-yl)-pyridin-2-ylamine (79 mg) described in Manufacturing Example 47-1 and (5-phenoxy-thiophen-2-yl)-methanol (100 mg) described in Manufacturing Example 46-1, by the same method as in Example 46.

$^1$H-NMR spectrum (DMSO-d$_6$) δ (ppm): 6.07 (2H, s), 6.51 (2H, brs), 6.54-6.60 (2H, m), 7.08-7.21 (4H, m), 7.40 (2H, dd, J=8.0 Hz, 8.0 Hz), 7.93 (1H, dd, J=2.0 Hz, 8.0 Hz), 8.58 (1H, s).

The starting substance 5-(2H-tetrazol-5-yl)-pyridin-2-ylamine was synthesized by the following method.

Manufacturing Example 47-1

5-(2H-tetrazol-5-yl)-pyridin-2-ylamine

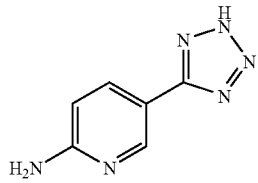

2-Amino-5-cyanopyridine (1.0 g), sodium azide (1.1 g), ammonium chloride (890 mg), and DMF (15 mL) were stirred for 2 hours and 15 minutes at 100° C. The reaction solution was directly purified by silica gel chromatography (ethyl acetate, then ethyl acetate:methanol:concentrated aqueous ammonia=6:2:1) to obtain the titled compound (860 mg).

$^1$H-NMR spectrum (DMSO-d$_6$) δ (ppm): 6.58 (1H, d, J=8.8 Hz), 6.65 (2H, brs), 7.98 (1H, dd, J=2.0 Hz, 8.8 Hz), 8.60 (1H, d, J=2.0 Hz).

Example 48

3-(2-(5-Benzyloxy-thiophen-2-ylmethyl)-2H-tetrazol-5-yl)-pyridin-2-ylamine

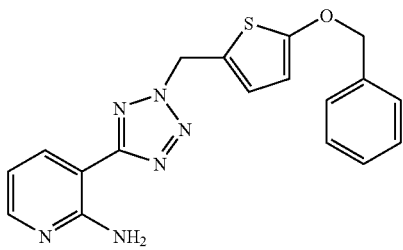

The titled compound (48 mg) was obtained from (5-benzyloxy-thiophen-2-yl)-methanol (140 mg) described in Manufacturing Example 48-1 and 3-(2H-tetrazol-5-yl)-pyridin-2-ylamine (100 mg) described in Manufacturing Example 5-1, by the same method as in Example 25.

$^1$H-NMR spectrum (DMSO-d$_6$) δ (ppm): 5.12 (2H, s), 6.08 (2H, s), 6.32 (1H, d, J=4.0 Hz), 6.74 (1H, dd, J=4.8 Hz, 8.0 Hz), 6.91 (2H, brs), 7.01 (1H, d, J=4.0 Hz), 7.32-7.45 (5H, m), 8.15 (1H, dd, J=2.0 Hz, 4.8 Hz), 8.24 (1H, dd, J=2.0 Hz, 8.0 Hz).

The starting substance (5-benzyloxy-thiophen-2-yl)-methanol was synthesized by the following method.

Manufacturing Example 48-1

(5-Benzyloxy-thiophen-2-yl)-methanol

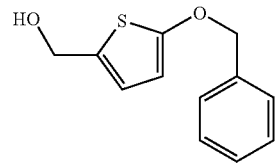

The titled compound (1.4 g) was obtained from 5-benzyloxy-thiophen-2-carbaldehyde (1.5 g) by the same method as in Manufacturing Example 46-1.

$^1$H-NMR spectrum (DMSO-d$_6$) δ (ppm): 4.22 (2H, d, J=6.0 Hz), 5.10 (2H, s), 5.28 (1H, t, J=6.0 Hz), 6.19 (1H, d, J=4.0 Hz), 6.54-6.58 (1H, m), 7.31-7.46 (5H, m).

Example 49

3-(2-Benzyl-2H-tetrazol-5-yl)-pyridin-2-ylamine

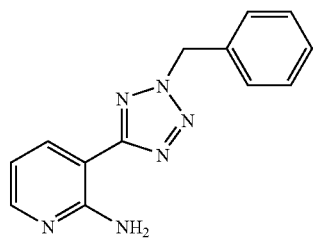

The titled compound (80 mg) was obtained from benzyl bromide (110 mg) and 3-(2H-tetrazol-5-yl)-pyridin-2-ylamine (100 mg) described in Manufacturing Example 5-1, by the same method as in Example 5.

$^1$H-NMR spectrum (DMSO-d$_6$) δ (ppm): 6.04 (2H, s), 6.74 (1H, dd, J=4.8 Hz, 8.0 Hz), 6.91 (2H, brs), 7.36-7.47 (5H, m), 8.15 (1H, dd, J=2.0 Hz, 4.8 Hz), 8.24 (1H, dd, J=2.0 Hz, 8.0 Hz).

Example 50

3-(2-(4-Ethoxy-benzyl)-2H-tetrazol-5-yl)-pyridin-2-ylamine

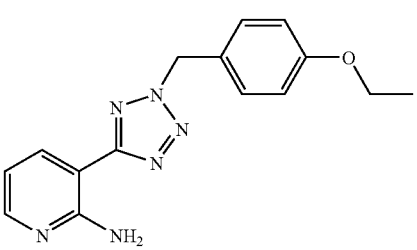

The titled compound (36 mg) was obtained from 4-ethoxy-benzyl alcohol (46 mg) and 3-(2H-tetrazol-5-yl)-pyridin-2-ylamine (150 mg) described in Manufacturing Example 5-1, by the same method as in Example 46.

$^1$H-NMR spectrum (DMSO-$d_6$) δ (ppm): 1.31 (3H, t, J=7.2 Hz), 4.01 (2H, q, J=7.2 Hz), 5.93 (2H, s), 6.71-6.76 (1H, m), 6.90 (2H, brs), 6.94 (2H, d, J=8.0 Hz), 7.39 (2H, d, J=8.0 Hz), 8.12-8.16 (1H, m), 8.20-8.25 (1H, m).

Example 51

3-(2-(5-(4-Fluoro-phenoxy)-furan-2-ylmethyl)-2H-tetrazol-5-yl)-pyridin-2-ylamine

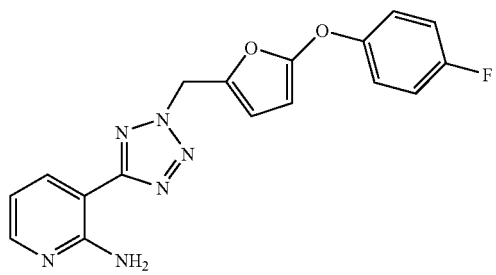

The titled compound (18 mg) was obtained from (5-(4-fluoro-phenoxy)-furan-2-yl)-methanol (120 mg) described in Manufacturing Example 51-1 and 3-(2H-tetrazol-5-yl)-pyridin-2-ylamine (100 mg) described in Manufacturing Example 5-1, by the same method as in Example 46.

$^1$H-NMR spectrum (DMSO-$d_6$) δ (ppm): 5.75 (1H, d, J=3.2 Hz), 6.03 (2H, s), 6.72-6.77 (2H, m), 6.90 (2H, brs), 7.10-7.18 (2H, m), 7.19-7.26 (2H, m), 8.16 (1H, dd, J=2.0 Hz, 4.8 Hz), 8.23 (1H, dd, J=2.0 Hz, 8.0 Hz).

The starting substance (5-(4-fluoro-phenoxy)-furan-2-yl)-methanol was synthesized by the following method.

Manufacturing Example 51-1

(5-(4-Fluoro-phenoxy)-furan-2-yl)-methanol

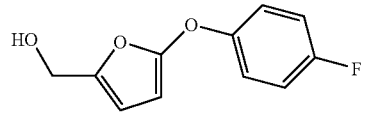

To a solution of DMSO (50 mL) of p-fluorophenol (3.6 g) was added NaH (1.3 g/60% in oil) at room temperature, which was stirred for 15 minutes at room temperature. 5-Nitro-furan-2-carbaldehyde (5.0 g) was then added thereto, which was stirred for 40 minutes at room temperature. Water was added to the reaction solution, which was then extracted with ethyl acetate. The solvent was evaporated from the organic layer under a reduced pressure, and the residue was purified by silica gel chromatography (heptane:ethyl acetate=2:1) to obtain 5-(4-fluoro-phenoxy)-furan-2-carbaldehyde (1.6 g).

Then, the titled compound (860 mg) was obtained from 5-(4-fluoro-phenoxy)-furan-2-carbaldehyde (850 mg), by the same method as in Manufacturing Example 46-1.

$^1$H-NMR spectrum (DMSO-$d_6$) δ (ppm): 4.29 (2H, d, J=6.0 Hz), 5.18 (1H, t, J=6.0 Hz), 5.67 (1H, d, J=3.2 Hz), 6.28 (1H, d, J=3.2 Hz), 7.10-7.15 (2H, m), 7.20-7.28 (2H, m).

Example 52

3-(2-(3-(5-Methyl-thiophen-2-ylmethyl)-benzyl)-2H-tetrazol-5-yl)-pyridin-2-ylamine

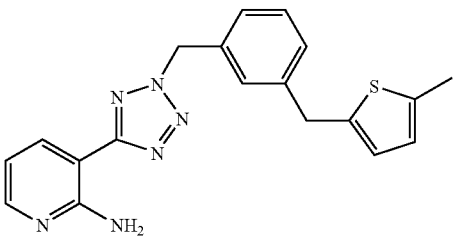

The titled compound (16 mg) was obtained from (3-(5-methyl-thiophen-2-ylmethyl)-phenyl)-methanol (40 mg) described in Manufacturing Example 52-3, 3-(2H-tetrazol-5-yl)-pyridin-2-ylamine (100 mg) described in Manufacturing Example 5-1, and azodicarboxylic acid dimethyl ester (130 mg), by the same method as in Example 46.

$^1$H-NMR spectrum (DMSO-$d_6$) δ (ppm): 2.31 (3H, s), 4.05 (2H, s), 6.00 (2H, s), 6.57-6.59 (1H, m), 6.64 (1H, d, J=3.2 Hz), 6.73 (1H, dd, J=4.8 Hz, 8.0 Hz), 6.90 (2H, brs), 7.23-7.30 (3H, m), 7.34 (1H, dd, J=8.0 Hz, 8.0 Hz), 8.15 (1H, dd, J=2.0 Hz, 4.8 Hz), 8.23 (1H, dd, J=2.0 Hz, 8.0 Hz).

The starting substance (3-(5-methyl-thiophen-2-ylmethyl)-phenyl)-methanol was synthesized by the following method.

Manufacturing Example 52-1

(3-[1,3]Dioxolan-2-yl-phenyl)-(5-methyl-thiophen-2-yl)-methanol

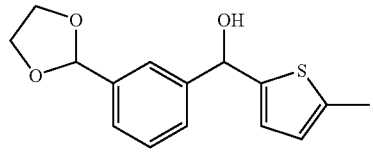

To a solution of THF (20 mL), 2-(3-bromophenyl)-1,3-dioxolane (2.7 g) and 1,2-dibromoethane (150 mg) was added magnesium (270 mg), which was heated to reflux for 10 minutes. The reaction mixture was cooled to 0° C., and a solution of 5-methyl-2-thiophencarbaldehyde (1.0 g) and THF (5 mL) was added thereto under stirring. The reaction solution was returned to room temperature and stirred for 10 minutes. Water was added to the reaction solution, which was then extracted with ethyl acetate. The solvent was evaporated from the organic layer under a reduced pressure, and the residue was purified by silica gel chromatography (heptane:ethyl acetate=2:1) to obtain the titled compound (1.1 g).

$^1$H-NMR spectrum (DMSO-$d_6$) δ (ppm): 2.36 (3H, s), 3.90-3.98 (2H, m), 4.00-4.16 (2H, m), 5.70 (1H, s), 5.85 (1H, d, J=3.6 Hz), 6.13 (1H, d, J=3.6 Hz), 6.56-6.59 (1H, m), 6.64 (1H, d, J=3.6 Hz), 7.28-7.41 (3H, m), 7.47 (1H, s).

Manufacturing Example 52-2

3-(5-Methyl-thiophen-2-ylmethyl)-benzaldehyde

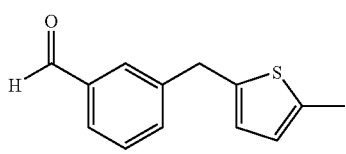

To a solution of acetonitrile (20 mL) and sodium iodide (2.9 g) was added trimethylsilyl chloride (2.1 g) at room temperature under stirring. The reaction solution thus obtained was cooled to −20° C., and (3-[1,3]dioxolan-2-yl-phenyl)-(5-methyl-thiophen-2-yl)-methanol (1.1 g) described in Manufacturing Example 52-1 and acetonitrile (5 mL) were added thereto under stirring. The reaction solution was returned to room temperature and stirred for 10 minutes. Water was added to the reaction solution, which was then extracted with ethyl acetate. The solvent was evaporated from the organic layer under a reduced pressure, and the residue was purified by silica gel chromatography (heptane:ethyl acetate=2:1) to obtain the titled compound (360 mg).

$^1$H-NMR spectrum (DMSO-$d_6$) δ (ppm): 2.36 (3H, s), 4.17 (2H, s), 6.62 (1H, d, J=3.2 Hz), 6.71 (1H, d, J=3.2 Hz), 7.52-7.62 (2H, m), 7.76-7.80 (2H, m), 9.99 (1H, s).

Manufacturing Example 52-3

(3-(5-Methyl-thiophen-2-ylmethyl)-phenyl)-methanol

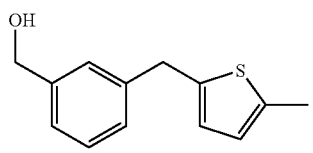

To a solution of ethanol (5.0 mL) and 3-(5-methyl-thiophen-2-ylmethyl)-benzaldehyde (350 mg) described in Manufacturing Example 52-2 was added sodium borohydride (120 mg), which was stirred for 10 minutes at room temperature. Water was added to the reaction solution, which was then extracted with ethyl acetate. The solvent was evaporated from the organic layer under a reduced pressure, and the residue was purified by silica gel chromatography (heptane:ethyl acetate=2:1) to obtain the titled compound (300 mg).

$^1$H-NMR spectrum (DMSO-$d_6$) δ (ppm): 2.35 (3H, s), 4.03 (2H, s), 4.46 (2H, d, J=6.0 Hz), 5.15 (1H, t, J=6.0 Hz), 6.58-6.61 (1H, m), 6.65 (1H, d, J=3.6 Hz), 7.09 (1H, d, J=7.6 Hz), 7.14 (1H, d, J=7.6 Hz), 7.19 (1H, s), 7.24 (1H, dd, J=7.6 Hz, 7.6 Hz).

Example 53

3-(2-(4-(5-Methyl-furan-2-ylmethyl)-benzyl)-2H-tetrazol-5-yl)-pyridin-2-ylamine

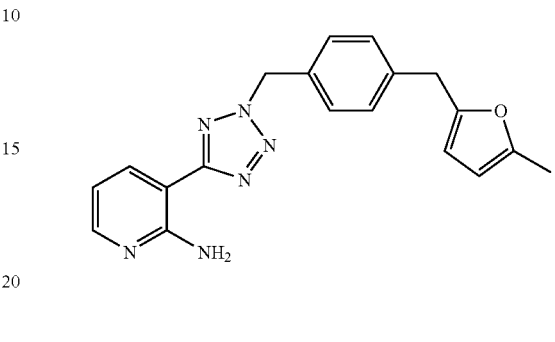

The titled compound (7.0 mg) was obtained from (4-(5-methyl-furan-2-ylmethyl)-phenyl)-methanol (22 mg) described in Manufacturing Example 53-3, 3-(2H-tetrazol-5-yl)-pyridin-2-ylamine (21 mg) described in Manufacturing Example 5-1, and azodicarboxylic acid dimethyl ester (32 mg/40% toluene solution), by the same method as in Example 46.

$^1$H-NMR spectrum (DMSO-$d_6$) δ (ppm): 2.17 (3H, s), 3.89 (2H, s), 5.92-5.95 (1H, m), 5.95-6.01 (3H, m), 6.72 (1H, dd, J=4.8 Hz, 8.0 Hz), 6.89 (2H, brs), 7.25 (2H, d, J=8.4 Hz), 7.37 (2H, d, J=8.4 Hz), 8.14 (1H, dd, J=2.0 Hz, 4.8 Hz), 8.23 (1H, dd, J=2.0 Hz, 8.0 Hz).

The starting substance (4-(5-methyl-furan-2-ylmethyl)-phenyl)-methanol was synthesized by the following method.

Manufacturing Example 53-1

(4-Dimethoxymethyl-phenyl)-(5-methyl-furan-2-yl)-methanol

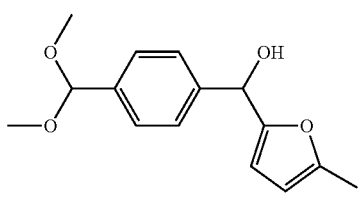

The titled compound (2.7 g) was obtained from 4-bromobenzaldehyde dimethyl acetal (4.0 g) and 5-methylfurfural (1.3 g), by the same method as in Manufacturing Example 52-1.

$^1$H-NMR spectrum (DMSO-$d_6$) δ (ppm): 2.17 (3H, s), 3.22 (6H, s), 5.34 (1H, s), 5.59 (1H, d, J=4.8 Hz), 5.88 (1H, d, J=4.8 Hz), 5.94 (2H, s), 7.32 (2H, d, J=8.0 Hz), 7.36 (2H, d, J=8.0 Hz).

Manufacturing Example 53-2

(4-(5-Methyl-furan-2-ylmethyl)-benzaldehyde

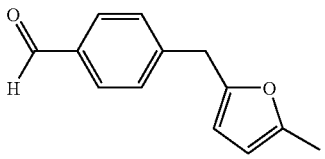

The titled compound (20 mg) was obtained from (4-dimethoxymethyl-phenyl)-(5-methyl-furan-2-yl)-methanol (1.0 g) described in Manufacturing Example 53-1, by the same method as in Manufacturing Example 52-2.

$^1$H-NMR spectrum (DMSO-$d_6$) δ (ppm): 2.19 (3H, s), 4.02 (2H, s), 5.96-5.99 (1H, m), 6.04 (1H, d, J=0.4 Hz), 7.44 (2H, d, J=8.0 Hz), 7.86 (2H, dd, J=1.6 Hz, 8.0 Hz), 9.97 (1H, s).

Manufacturing Example 53-3

(4-(5-Methyl-furan-2-ylmethyl)-phenyl)-methanol

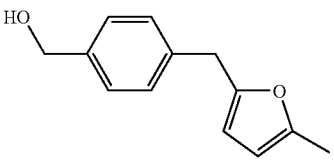

The titled compound (22 mg) was obtained from (4-(5-methyl-furan-2-ylmethyl)-benzaldehyde (20 mg) described in Manufacturing Example 53-2, by the same method as in Manufacturing Example 52-3.

$^1$H-NMR spectrum (DMSO-$d_6$) δ (ppm): 2.18 (3H, s), 3.86 (2H, s), 4.45 (2H, d, J=6.0 Hz), 5.12 (1H, t, J=6.0 Hz), 5.92-5.98 (2H, m), 7.16 (2H, d, J=8.0 Hz), 7.23 (2H, dd, J=1.2 Hz, 8.0 Hz).

Example 54

3-(2-(4-(5-Bromo-thiophen-2-ylmethyl)-benzyl)-2H-tetrazol-5-yl)-pyridin-2-ylamine

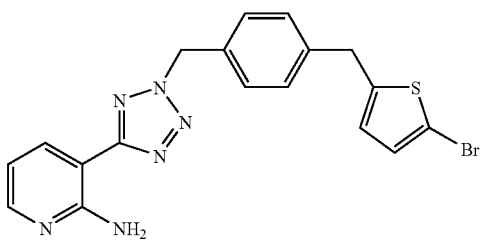

The titled compound (28 mg) was obtained from (4-(5-bromo-thiophen-2-ylmethyl)-phenyl)-methanol (120 mg) described in Manufacturing Example 54-3, 3-(2H-tetrazol-5-yl)-pyridin-2-ylamine (69 mg) described in Manufacturing Example 5-1, and azodicarboxylic acid dimethyl ester (310 mg/40% toluene solution), by the same method as in Example 46.

$^1$H-NMR spectrum (DMSO-$d_6$) δ (ppm): 4.11 (2H, s), 5.99 (2H, s), 6.70-6.76 (2H, m), 6.89 (2H, brs), 7.03 (1H, d, J=3.6 Hz), 7.29 (2H, d, J=8.0 Hz), 7.38 (2H, d, J=8.0 Hz), 8.14 (1H, dd, J=2.0 Hz, 4.8 Hz), 8.23 (1H, dd, J=2.0 Hz, 8.0 Hz).

The starting substance (4-(5-bromo-thiophen-2-ylmethyl)-phenyl)-methanol was synthesized by the following method.

Manufacturing Example 54-1

(5-Bromo-thiophen-2-yl)-(4-dimethoxymethyl-phenyl)-methanol

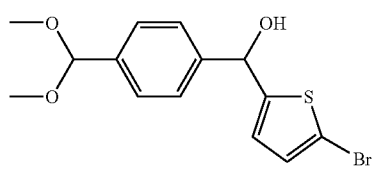

The titled compound (3.3 g) was obtained from 4-bromobenzaldehyde dimethyl acetal (5.0 g) and 5-bromo-2-thiophenecarboxyaldehyde (2.9 g), by the same method as in Manufacturing Example 52-1.

$^1$H-NMR spectrum (DMSO-$d_6$) δ (ppm): 3.21 (6H, s), 5.34 (1H, s), 5.87 (1H, d, J=4.4 Hz), 6.37 (1H, d, J=4.4 Hz), 6.66 (1H, d, J=4.0 Hz), 6.99 (1H, d, J=4.0 Hz), 7.33 (2H, d, J=8.0 Hz), 7.39 (2H, d, J=8.0 Hz).

Manufacturing Example 54-2

4-(5-Bromo-thiophen-2-ylmethyl)-benzaldehyde

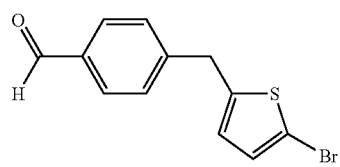

The titled compound (1.9 g) was obtained from the (5-bromo-thiophen-2-yl)-(4-dimethoxymethyl-phenyl)-methanol (3.3 g) described in Manufacturing Example 54-1, by the same method as in Manufacturing Example 52-2.

$^1$H-NMR spectrum (DMSO-$d_6$) δ (ppm): 4.22 (2H, s), 6.79 (1H, d, J=3.6 Hz), 7.05 (1H, d, J=3.6 Hz), 7.47 (2H, d, J=8.0 Hz), 7.85 (2H, d, J=8.0 Hz), 9.96 (1H, s).

Manufacturing Example 54-3

(4-(5-Bromo-thiophen-2-ylmethyl)-phenyl)-methanol

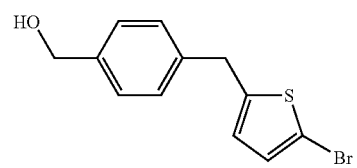

The titled compound (810 mg) was obtained from 4-(5-bromo-thiophen-2-ylmethyl)-benzaldehyde (1.9 g) described in Manufacturing Example 54-2, by the same method as in Manufacturing Example 52-3.

$^1$H-NMR spectrum (DMSO-d$_6$) δ (ppm): 4.08 (2H, s), 4.45 (2H, d, J=5.6 Hz), 5.13 (1H, t, J=5.6 Hz), 6.74 (1H, d, J=3.6 Hz), 7.03 (1H, d, J=3.6 Hz), 7.20 (2H, d, J=8.0 Hz), 7.25 (2H, d, J=8.0 Hz).

Example 55

3-(2-(1-Benzyl-1H-pyrrol-3-ylmethyl)-2H-tetrazol-5-yl)-pyridin-2-ylamine

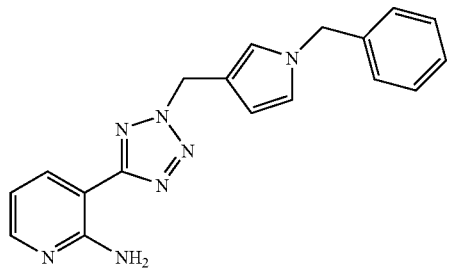

The titled compound (5.9 mg) was obtained from (1-benzyl-1H-pyrrol-3-yl)-methanol (50 mg) described in Manufacturing Example 55-1, 3-(2H-tetrazol-5-yl)-pyridin-2-ylamine (43 mg) described in Manufacturing Example 5-1, and azodicarboxylic acid dimethyl ester (59 mg/40% toluene solution), by the same method as in Example 46.

$^1$H-NMR spectrum (DMSO-d$_6$) δ (ppm): 5.07 (2H, s), 5.76 (2H, s), 6.12 (1H, dd, J=2.0 Hz, 2.0 Hz), 6.73 (1H, dd, J=4.8 Hz, 8.0 Hz), 6.81 (1H, dd, J=2.0 Hz, 2.0 Hz), 6.90 (2H, brs), 7.04 (1H, dd, J=2.0 Hz, 2.0 Hz), 7.20 (2H, d, J=8.0 Hz), 7.24-7.60 (1H, m), 7.60-7.78 (2H, m), 8.14 (1H, dd, J=2.0 Hz, 4.8 Hz), 8.22 (1H, dd, J=2.0 Hz, 8.0 Hz).

The starting substance (1-benzyl-1H-pyrrol-3-yl)-methanol was synthesized by the following method.

Manufacturing Example 55-1

(1-Benzyl-1H-pyrrol-3-yl)-methanol

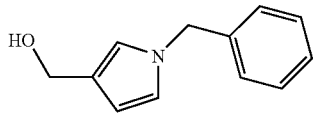

The titled compound (210 mg) was obtained from 1-benzyl-1H-pyrrole-3-carbaldehyde (260 mg), by the same method as in Manufacturing Example 46-1.

$^1$H-NMR spectrum (DMSO-d$_6$) δ (ppm): 4.27 (2H, d, J=6.0 Hz), 4.54 (1H, t, J=6.0 Hz), 5.02 (2H, s), 5.96 (1H, dd, J=2.0 Hz, 2.0 Hz), 6.69 (1H, dd, J=2.0 Hz, 2.0 Hz), 6.73 (1H, dd, J=2.0 Hz, 2.0 Hz), 7.19 (2H, d, J=6.8 Hz), 7.23-7.29 (1H, m), 7.30-7.35 (2H, m).

The compounds I of the present invention and salts thereof exhibit excellent inhibitory activity on the GPI-anchored protein transport process, anti-Candida activity, and anti-Aspergillus activity, and are also superior in terms of their physical properties, safety, and metabolic stability, making them extremely useful as an agent for preventing or treating fungal infections.

Pharmacological Test Examples

In order to demonstrate the usefulness of the compounds I of the present invention, the antifungal activity of the compounds I of the present invention was evaluated by measuring 1) anti-*Candida* and anti-*Aspergillus* activity and 2) activity in an experimental systemic candidal infection model in mice.

1. Anti-*Candida* Activity and Anti-*Aspergillus* Activity (1) Preparation of Fungal Sample For the *C. albicans* CAF2-1 strain, a fungal suspension from a standing culture for 48 hours at 30° C. in a Sabouraud dextrose liquid culture medium (SDB) was diluted with RPMI 1640 medium to adjust a fungal suspension of 1.2×10$^3$ cells/mL. For the *A. fumigatus* Tsukuba strain, −80° C. stored strain was diluted with RPMI 1640 medium to adjust to a fungal suspension of 4.5×10$^3$ cells/mL.

(2) Preparation of an Agent Dilution Plate

Using a U-bottomed 96-well plate, 8 samples/plate (A to H) of sample dilution solutions were prepared. On the 2$^{nd}$ to 12$^{th}$ rows were dispensed 10 μL of dimethyl sulfoxide solution. Weighed sample was dissolved in dimethyl sulfoxide to prepare a 2.5 mg/mL solution, 20 μL of this solution was added to the first row of the prepared plate, and 12 steps of two-fold step dilutions (10 μL of solution+10 μL of dimethyl sulfoxide solution) were performed on the plate. This sample dilution solution was dispensed in an amount of 1 μL into a flat-bottomed 96-well plate for MIC measurement to prepare a sample dilution plate.

(3) Inoculation of Fungal Suspension and Culture

The fungal suspension prepared in (1) was used in an amount of 99 μL/well to inoculate the flat-bottomed 96-well plate containing 1 μL/well of the test compound dilution prepared in (2), and standing culture was performed aerobically for 42 to 48 hours at 35° C.

(4) MIC Measurement

The minimum concentration that clearly inhibited fungal growth as compared to the control by visual inspection was determined as the minimum inhibitory concentration (MIC).

The following representative compounds prepared in the examples were measured for anti-*Candida* activity and anti-*Aspergillus* activity by measurement method in (1). As a result, as shown in Tables 1 and 2, it was found that the compounds according to the present invention clearly had anti-*Candida* and anti-*Aspergillus* activity.

TABLE 1

| Working Ex. Nos. | Anti-*Candida* Activity (μg/mL) |
|---|---|
| 1 | 0.05 |
| 2 | 3.13 |
| 3 | 1.56 |
| 4 | 0.39 |
| 5 | 0.78 |
| 6 | 1.56 |
| 7 | 0.39 |
| 8 | 0.78 |
| 9 | 0.39 |
| 10 | 3.13 |
| 11 | 6.25 |
| 12 | 0.2 |
| 13 | 1.56 |
| 14 | 6.25 |
| 15 | 6.25 |
| 16 | 0.05 |

TABLE 1-continued

| Working Ex. Nos. | Anti-Candida Activity (µg/mL) |
|---|---|
| 17 | 3.13 |
| 19 | 0.39 |
| 21 | 0.39 |
| 22 | 0.39 |
| 23 | 1.56 |
| 24 | 1.56 |
| 26 | 0.05 |
| 27 | 0.2 |
| 28 | 0.1 |
| 29 | 0.39 |
| 31 | 0.39 |
| 32 | 0.1 |
| 35 | 1.56 |
| 37 | 0.2 |
| 40 | 1.56 |
| 41 | 0.39 |
| 42 | 0.2 |
| 45 | 6.25 |
| 46 | 0.39 |
| 48 | 0.39 |
| 49 | 1.56 |
| 50 | 6.25 |
| 51 | 6.25 |
| 52 | 1.56 |
| 53 | 0.39 |
| 55 | 0.1 |

TABLE 2

| Working Ex. Nos. | Anti-Aspergillus Activity (µg/mL) |
|---|---|
| 1 | 0.2 |
| 2 | 1.56 |
| 3 | 0.78 |
| 4 | 0.78 |
| 5 | 1.56 |
| 6 | 1.56 |
| 7 | 1.56 |
| 8 | 1.56 |
| 9 | 0.78 |
| 10 | 25 |
| 11 | 3.13 |
| 12 | 0.2 |
| 13 | 1.56 |
| 14 | >25 |
| 15 | 3.13 |
| 16 | 0.78 |
| 17 | 0.78 |
| 19 | 3.13 |
| 21 | 0.39 |
| 22 | 1.56 |
| 23 | 6.25 |
| 24 | 6.25 |
| 26 | 0.39 |
| 27 | 0.78 |
| 28 | 1.56 |
| 29 | 1.56 |
| 31 | 0.78 |
| 32 | 0.39 |
| 35 | 0.78 |
| 37 | 1.56 |
| 40 | >25 |
| 41 | 1.56 |
| 42 | 0.78 |
| 45 | 12.5 |
| 46 | 1.56 |
| 48 | 1.56 |
| 49 | 12.5 |
| 50 | >25 |
| 51 | 3.13 |

TABLE 2-continued

| Working Ex. Nos. | Anti-Aspergillus Activity (µg/mL) |
|---|---|
| 52 | 3.13 |
| 53 | 0.78 |
| 55 | 0.78 |

2. Experimental Systemic Candidal Infection Model in Mice (1) Preparation of Fungal Inoculant A standing culture of *C. albicans* E81022 strain was carried out for 48 hours at 30° C. in Sabouraud dextrose agar medium (SDA), and the recovered fungal cells were suspended in sterilized physiological saline. By counting the fungal number on cytometry plate, the suspension was diluted to $2\times10^7$ cells/mL with sterilized physiological saline to serve fungal inoculum.

(2) Infection

The fungal inoculum was used in amounts of 0.2 mL to inoculate 4.5 to 5.5 week-old female ICR mice in the tail vein ($4\times10^6$ cells/mouse).

(3) Treatment

From 0.5 to 1 hour after fungal inoculation, 0.2 mL of agent solution (dissolved or suspended in sterilized physiological saline containing 6.5% dimethyl sulfoxide and 3.5% Tween 80) was administered into the stomach using a peroral probe, 3 times every 4 hours. The agent concentration was 2.5 or 10 mg/kg, and the number of animal in one group was five animals.

(4) Determination of Effects

The protective effect was determined by observing life/death until 14 days after infection and calculating the mean survival days.

As a result, as shown in Table 3, mice administered with the compounds of the present invention survived for a long time as compared to the untreated group, and it was clear that the compounds of the present invention exhibit anti-*Candida* activity in vivo.

TABLE 3

Mean Survival Day (MSD)

| Example Nos. | Non-Administered group | Dose (mg/kg) 2.5 | Dose (mg/kg) 10 |
|---|---|---|---|
| 5 | 4.0 | — | 11.8 |
| 9 | 5.0 | 7.8 | 10.8 |
| 27 | 5.0 | 5.6 | 12 |
| 41 | 3.2 | 6.2 | 11.2 |
| 42 | 3.2 | — | 13.6 |
| 53 | 5.0 | 7.6 | 13.8 |

We claim:

1. A compound represented by the following Formula I or a salt thereof:

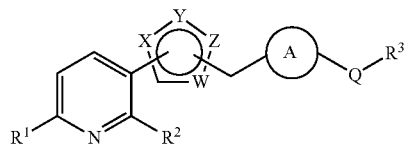

(I)

wherein R¹ is a hydrogen atom, a halogen atom, an amino group, a $C_{1-6}$ alkyl group, a $C_{1-6}$ alkoxy group, or a $C_{1-6}$-alkoxy-$C_{1-6}$-alkyl group;
R² is a hydrogen atom or an amino group;
X is —CH—;
Y, Z, and W are each independently a nitrogen atom;
the ring A is a benzene ring;
Q is a methylene group, an oxygen atom, —CH₂O—, —OCH₂—, —NH—, —NHCH₂—, or —CH₂NH—;
R³ is a $C_{1-6}$ alkyl group, a $C_{3-8}$ cycloalkyl group, or a $C_{6-10}$ aryl group, each of which may have one or two substituent(s) selected from among a substituent group α;
Substituent Group α:
a halogen atom, a $C_{1-6}$ alkyl group, a $C_{1-6}$ alkoxy group, a $C_{3-8}$ cycloalkyl group, a $C_{2-6}$ alkenyl group, and a $C_{2-6}$ alkynyl group.

2. The compound or salt thereof according to claim 1, wherein the partial structure represented by the following Formula II:

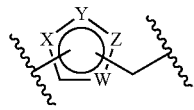

(II)

of the compound represented by the following Formula I:

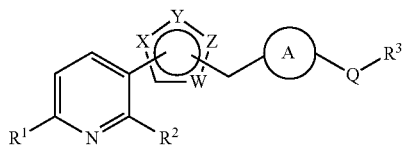

(I)

is a partial structure represented by the following Formula III:

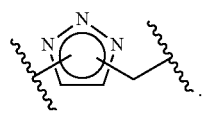

(III)

3. The compound or salt thereof according to claim 2, wherein the partial structure represented by the following Formula II:

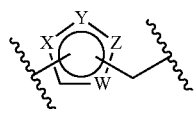

(II)

of the compound represented by the following Formula I:

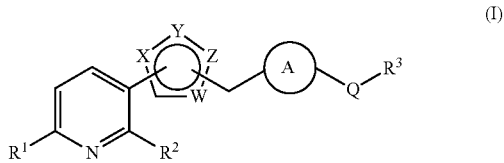

(I)

is a partial structure of:

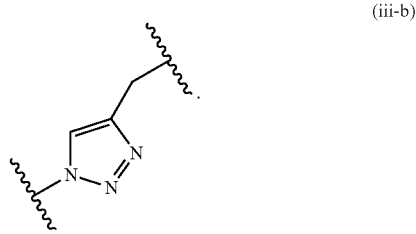

(iii-b)

4. The compound or salt thereof according to claim 1, wherein R² is an amino group.

5. The compound or salt thereof according to claim 4, wherein R¹ is a hydrogen atom, an amino group, or a $C_{1-6}$-alkoxy-$C_{1-6}$-alkyl group.

6. The compound or salt thereof according to claim 1, wherein R¹ is an amino group, and R² is a hydrogen atom.

7. The compound or salt thereof according to claim 1, wherein Q is an oxygen atom, —CH₂O—, or —OCH₂—.

8. A pharmaceutical composition comprising:
the compound or salt thereof according to claim 1; and
a pharmaceutically acceptable carrier.

9. A method for treating fungal infection by administering a pharmaceutically effective amount of the compound or the salt thereof according to any one of claims 1, 2, 3, 4-6, and 7.

10. The compound or salt thereof according to claim 1, wherein Q is the oxygen atom.

11. The compound or salt thereof according to claim 1, wherein R¹ is the hydrogen atom and R² is the amino group.

12. The compound or salt thereof according to claim 1, wherein the compound is 3-(1-(3-phenoxy-benzyl)-1H-[1,2,3]triazol-4-yl)-pyridin-2-ylamine represented by:

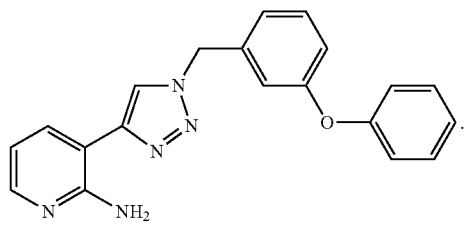

* * * * *